US012594302B2

(12) United States Patent (10) Patent No.: US 12,594,302 B2
Moutel et al. (45) Date of Patent: Apr. 7, 2026

(54) SINGLE DOMAIN ANTIBODIES AND THEIR USE IN CANCER THERAPIES

(71) Applicants: Institut Curie, Paris (FR); Centre National de la Recherche Scientifique, Paris (FR); The University of Zurich, Zurich (CH); Honing Biosciences, Paris (FR)

(72) Inventors: Sandrine Moutel, Paris (FR); Franck Perez, Paris (FR); Michele Bernasconi, Zollikon (CH); Nagjie Laila Alijaj, Zurich (CH); Zélia Gouveia, Orly (FR)

(73) Assignees: Institut Curie, Paris (FR); Honing Biosciences, Paris (FR); Centre National de la Recherche Scientifique, Paris (FR); The University of Zurich, Zurich (CH)

( * ) Notice: Subject to any disclaimer, the term of this patent is extended or adjusted under 35 U.S.C. 154(b) by 706 days.

(21) Appl. No.: 17/925,411

(22) PCT Filed: May 20, 2021

(86) PCT No.: PCT/EP2021/063518
§ 371 (c)(1),
(2) Date: Nov. 15, 2022

(87) PCT Pub. No.: WO2021/234110
PCT Pub. Date: Nov. 25, 2021

(65) Prior Publication Data
US 2023/0302050 A1 Sep. 28, 2023

(30) Foreign Application Priority Data
May 20, 2020 (EP) .................................... 20305535

(51) Int. Cl.
| | |
|---|---|
| *A61K 35/17* | (2025.01) |
| *A61K 40/11* | (2025.01) |
| *A61K 40/31* | (2025.01) |
| *A61K 40/42* | (2025.01) |
| *C07K 16/28* | (2006.01) |
| *C12N 15/63* | (2006.01) |
| *G01N 33/574* | (2006.01) |

(52) U.S. Cl.
CPC .............. *A61K 35/17* (2013.01); *A61K 40/11* (2025.01); *A61K 40/31* (2025.01); *A61K 40/4206* (2025.01); *A61K 40/4211* (2025.01); *C07K 16/2863* (2013.01); *C12N 15/63* (2013.01); *G01N 33/574* (2013.01); *A61K 2239/46* (2023.05); *C07K 2317/565* (2013.01); *C07K 2317/567* (2013.01); *C07K 2317/569* (2013.01)

(58) Field of Classification Search
CPC ............................ C07K 16/2863; A61K 40/31
See application file for complete search history.

(56) References Cited

U.S. PATENT DOCUMENTS

2018/0318440 A1 11/2018 Khan et al.

OTHER PUBLICATIONS

International Search Report issued in corresponding International Patent Application No. PCT/EP2021/063518 dated Jul. 28, 2021.
Written Opinion issued in corresponding International Patent Application No. PCT/EP2021/063518 dated Jul. 28, 2021.
Database Embase [Online] Elsevier Science Publishers, Alijaj et al., "Targeting fibroblast growth factor receptors in rhabdomyosarcoma," (Jul. 1, 2019).
Database Embase [Online] Elsevier Science Publishers, Shivaprasad et al., "FGFR4 specific chimeric antigen receptor (CAR) T cell therapy against rhabdomyosarcoma," (Nov. 1, 2017).

*Primary Examiner* — Christopher M Babic
*Assistant Examiner* — Jennifer S Spence
(74) *Attorney, Agent, or Firm* — Morgan, Lewis & Bockius LLP

(57) ABSTRACT

The present application relates to fully humanized anti-FGFR4 single domain antibodies (sdAbs) and variants thereof. The present invention further relates to functionalized drug nanocarriers, nucleic acids, vectors, host cells, immune cells comprising said sdAbs, and compositions comprising thereof, as well as their use for therapy.

24 Claims, 7 Drawing Sheets

Figure 1:
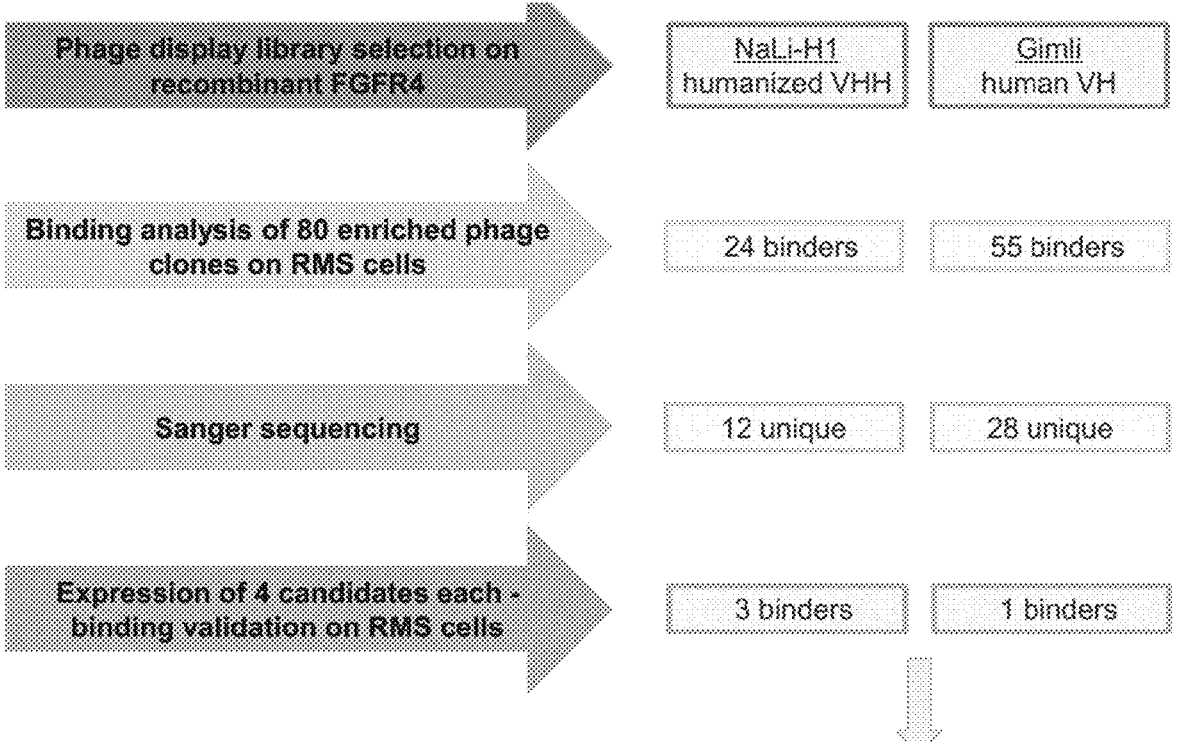

Specification includes a Sequence Listing.

| Name | CDR1 | CDR2 | CDR3 | Nanobody |
|------|------|------|------|----------|
| A8 | RTYSRDT (SEQ ID NO: 1) | SRHSHTT (SEQ ID NO: 2) | EWDVFDMHYALPPMW (SEQ ID NO: 3) | VHH |
| B1 | YTSRSSA (SEQ ID NO: 4) | DLTGYPY (SEQ ID NO: 5) | AYQDDKWTYGSQHGK (SEQ ID NO: 6) | VHH |
| B5 | RTWLTT (SEQ ID NO: 7) | SFSSKQG (SEQ ID NO: 8) | YASYPRHQGNGRWKDFVE (SEQ ID NO: 9) | VHH |
| F8 | TGYALDD (SEQ ID NO: 10) | DDESMAD (SEQ ID NO: 11) | SYKEYKYQSGHHYFA (SEQ ID NO: 12) | VH |

L-A8    L-B1    L-B5

L-F8    L-mCh

SEQUENCE LISTING

<160> NUMBER OF SEQ ID NOS: 45

<210> SEQ ID NO 1
<211> LENGTH: 7
<212> TYPE: PRT
<213> ORGANISM: Artificial Sequence
<220> FEATURE:
<223> OTHER INFORMATION: Synthetic sequence

<400> SEQUENCE: 1

Arg Thr Tyr Ser Arg Asp Thr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic sequence

<400> SEQUENCE: 2

Ser Arg His Ser His Thr Thr
1               5

<210> SEQ ID NO 3
<211> LENGTH: 15
<212> TYPE: PRT
<213> ORGANISM: Artificial Sequence
<220> FEATURE:
<223> OTHER INFORMATION: Synthetic sequence

<400> SEQUENCE: 3

Glu Trp Asp Val Phe Asp Met His Tyr Ala Leu Pro Pro Met Trp
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic sequence

<400> SEQUENCE: 4

-continued

```
Tyr Thr Ser Arg Ser Ser Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic sequence

<400> SEQUENCE: 5

Asp Leu Thr Gly Tyr Pro Tyr
1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic sequence

<400> SEQUENCE: 6

Ala Tyr Gln Asp Asp Lys Trp Thr Tyr Gly Ser Gln His Gly Lys
1               5                   10                  15

<210> SEQ ID NO 7
<211> LENGTH: 6
<212> TYPE: PRT
<213> ORGANISM: Artificial Sequence
<220> FEATURE:
<223> OTHER INFORMATION: Synthetic sequence

<400> SEQUENCE: 7

Arg Thr Trp Leu Thr Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic sequence

<400> SEQUENCE: 8

Ser Phe Ser Ser Lys Gln Gly
1               5

<210> SEQ ID NO 9
<211> LENGTH: 18
<212> TYPE: PRT
<213> ORGANISM: Artificial Sequence
<220> FEATURE:
<223> OTHER INFORMATION: Synthetic sequence

<400> SEQUENCE: 9

Tyr Ala Ser Tyr Pro Arg His Gln Gly Asn Gly Arg Trp Lys Asp Phe
1               5                   10                  15

Val Glu

<210> SEQ ID NO 10
<211> LENGTH: 7
<212> TYPE: PRT
<213> ORGANISM: Artificial Sequence
<220> FEATURE:
<223> OTHER INFORMATION: Synthetic sequence
```

-continued

```
<400> SEQUENCE: 10

Thr Gly Tyr Ala Leu Asp Asp
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic sequence

<400> SEQUENCE: 11

Asp Asp Glu Ser Met Ala Asp
1               5

<210> SEQ ID NO 12
<211> LENGTH: 15
<212> TYPE: PRT
<213> ORGANISM: Artificial Sequence
<220> FEATURE:
<223> OTHER INFORMATION: Synthetic sequence

<400> SEQUENCE: 12

Ser Tyr Lys Glu Tyr Lys Tyr Gln Ser Gly His His Tyr Phe Ala
1               5                   10                  15

<210> SEQ ID NO 13
<211> LENGTH: 26
<212> TYPE: PRT
<213> ORGANISM: Artificial Sequence
<220> FEATURE:
<223> OTHER INFORMATION: Synthetic sequence

<400> SEQUENCE: 13

Glu Val Gln Leu Gln Ala Ser Gly Gly Gly Phe Val Gln Pro Gly Gly
1               5                   10                  15

Ser Leu Arg Leu Ser Cys Ala Ala Ser Gly
            20                  25

<210> SEQ ID NO 14
<211> LENGTH: 19
<212> TYPE: PRT
<213> ORGANISM: Artificial Sequence
<220> FEATURE:
<223> OTHER INFORMATION: Synthetic sequence

<400> SEQUENCE: 14

Met Gly Trp Phe Arg Gln Ala Pro Gly Lys Glu Arg Glu Phe Val Ser
1               5                   10                  15

Ala Ile Ser

<210> SEQ ID NO 15
<211> LENGTH: 39
<212> TYPE: PRT
<213> ORGANISM: Artificial Sequence
<220> FEATURE:
<223> OTHER INFORMATION: Synthetic sequence

<400> SEQUENCE: 15

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Arg Ala Glu Asp
            20                  25                  30

Thr Ala Thr Tyr Tyr Cys Ala
```

```
        35

<210> SEQ ID NO 16
<211> LENGTH: 12
<212> TYPE: PRT
<213> ORGANISM: Artificial Sequence
<220> FEATURE:
<223> OTHER INFORMATION: Synthetic sequence

<400> SEQUENCE: 16

Tyr Trp Gly Gln Gly Thr Gln Val Thr Val Ser Ser
1               5                   10

<210> SEQ ID NO 17
<211> LENGTH: 26
<212> TYPE: PRT
<213> ORGANISM: Artificial Sequence
<220> FEATURE:
<223> OTHER INFORMATION: Synthetic sequence

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 18
<211> LENGTH: 19
<212> TYPE: PRT
<213> ORGANISM: Artificial Sequence
<220> FEATURE:
<223> OTHER INFORMATION: Synthetic sequence

<400> SEQUENCE: 18

Met Gly Trp Val Arg Gln Ala Pro Gly Lys Gly Leu Glu Trp Val Ser
1               5                   10                  15

Ala Ile Ser

<210> SEQ ID NO 19
<211> LENGTH: 39
<212> TYPE: PRT
<213> ORGANISM: Artificial Sequence
<220> FEATURE:
<223> OTHER INFORMATION: Synthetic sequence

<400> SEQUENCE: 19

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Arg Ala Glu Asp
            20                  25                  30

Thr Ala Val Tyr Tyr Cys Ala
        35

<210> SEQ ID NO 20
<211> LENGTH: 12
<212> TYPE: PRT
<213> ORGANISM: Artificial Sequence
<220> FEATURE:
<223> OTHER INFORMATION: Synthetic sequence

<400> SEQUENCE: 20

Tyr Arg Gly Gln Gly Thr Leu Val Thr Val Ser Ser
1               5                   10
```

-continued

```
<210> SEQ ID NO 21
<211> LENGTH: 21
<212> TYPE: DNA
<213> ORGANISM: Artificial Sequence
<220> FEATURE:
<223> OTHER INFORMATION: Synthetic sequence

<400> SEQUENCE: 21
cgtacataca gtcgtgatac a                                          21

<210> SEQ ID NO 22
<211> LENGTH: 21
<212> TYPE: DNA
<213> ORGANISM: Artificial Sequence
<220> FEATURE:
<223> OTHER INFORMATION: Synthetic sequence

<400> SEQUENCE: 22
agtcgtcatt cgcatacaac a                                          21

<210> SEQ ID NO 23
<211> LENGTH: 45
<212> TYPE: DNA
<213> ORGANISM: Artificial Sequence
<220> FEATURE:
<223> OTHER INFORMATION: Synthetic sequence

<400> SEQUENCE: 23
gagtgggacg tttttgacat gcactatgca ctgcctccta tgtgg               45

<210> SEQ ID NO 24
<211> LENGTH: 21
<212> TYPE: DNA
<213> ORGANISM: Artificial Sequence
<220> FEATURE:
<223> OTHER INFORMATION: Synthetic sequence

<400> SEQUENCE: 24
tatacaagtc gttcgtccgc a                                          21

<210> SEQ ID NO 25
<211> LENGTH: 21
<212> TYPE: DNA
<213> ORGANISM: Artificial Sequence
<220> FEATURE:
<223> OTHER INFORMATION: Synthetic sequence

<400> SEQUENCE: 25
gacctgacag ggtatcctta c                                          21

<210> SEQ ID NO 26
<211> LENGTH: 45
<212> TYPE: DNA
<213> ORGANISM: Artificial Sequence
<220> FEATURE:
<223> OTHER INFORMATION: Synthetic sequence

<400> SEQUENCE: 26
gcatatcagg acgacaagtg gacatatggt tcgcagcacg gtaag               45

<210> SEQ ID NO 27
<211> LENGTH: 21
<212> TYPE: DNA
<213> ORGANISM: Artificial Sequence
<220> FEATURE:
<223> OTHER INFORMATION: Synthetic sequence
```

-continued

```
<400> SEQUENCE: 27
cgtacttcat ggctgactac a                                               21

<210> SEQ ID NO 28
<211> LENGTH: 21
<212> TYPE: DNA
<213> ORGANISM: Artificial Sequence
<220> FEATURE:
<223> OTHER INFORMATION: Synthetic sequence

<400> SEQUENCE: 28
agtttttcga gtaagcaggg t                                               21

<210> SEQ ID NO 29
<211> LENGTH: 54
<212> TYPE: DNA
<213> ORGANISM: Artificial Sequence
<220> FEATURE:
<223> OTHER INFORMATION: Synthetic sequence

<400> SEQUENCE: 29
tatgcatcgt atcctcgtca ccagggtaac ggtcgttgga aggactttgt tgag           54

<210> SEQ ID NO 30
<211> LENGTH: 21
<212> TYPE: DNA
<213> ORGANISM: Artificial Sequence
<220> FEATURE:
<223> OTHER INFORMATION: Synthetic sequence

<400> SEQUENCE: 30
acaggatatg ccctcgatga t                                               21

<210> SEQ ID NO 31
<211> LENGTH: 21
<212> TYPE: DNA
<213> ORGANISM: Artificial Sequence
<220> FEATURE:
<223> OTHER INFORMATION: Synthetic sequence

<400> SEQUENCE: 31
gatgatgaga gtatggctga t                                               21

<210> SEQ ID NO 32
<211> LENGTH: 45
<212> TYPE: DNA
<213> ORGANISM: Artificial Sequence
<220> FEATURE:
<223> OTHER INFORMATION: Synthetic sequence

<400> SEQUENCE: 32
tcctataagg agtacaagta tcagagcgga caccactatt tcgct                     45

<210> SEQ ID NO 33
<211> LENGTH: 78
<212> TYPE: DNA
<213> ORGANISM: Artificial Sequence
<220> FEATURE:
<223> OTHER INFORMATION: Synthetic sequence

<400> SEQUENCE: 33
gaagtgcagc tgcaggcttc cggggggagga tttgtgcagc cggggggggtc attgcgactg   60 agctgcgccg catccggg                                                   78
```

-continued

<210> SEQ ID NO 34
<211> LENGTH: 57
<212> TYPE: DNA
<213> ORGANISM: Artificial Sequence
<220> FEATURE:
<223> OTHER INFORMATION: Synthetic sequence

<400> SEQUENCE: 34
atgggctggt ttcgtcaggc ccctggcaag gagagagagt tcgtttccgc catctcg          57

<210> SEQ ID NO 35
<211> LENGTH: 117
<212> TYPE: DNA
<213> ORGANISM: Artificial Sequence
<220> FEATURE:
<223> OTHER INFORMATION: Synthetic sequence

<400> SEQUENCE: 35
tactacgctg acagcgtaaa gggaagattt acaattagcc gggataactc caaaaacacg          60
gtctatctcc agatgaacag cctcagggcc gaggacacag ctacgtatta ctgtgca          117

<210> SEQ ID NO 36
<211> LENGTH: 36
<212> TYPE: DNA
<213> ORGANISM: Artificial Sequence
<220> FEATURE:
<223> OTHER INFORMATION: Synthetic sequence

<400> SEQUENCE: 36
tattggggac aggggacgca ggtaactgtg agtagc                                   36

<210> SEQ ID NO 37
<211> LENGTH: 78
<212> TYPE: DNA
<213> ORGANISM: Artificial Sequence
<220> FEATURE:
<223> OTHER INFORMATION: Synthetic sequence

<400> SEQUENCE: 37
gaagtgcagc tggtggagtc cggggggagga ctggtgcagc cggggggggtc attgcgactg          60 agctgcgccg catccggg                                                       78

<210> SEQ ID NO 38
<211> LENGTH: 57
<212> TYPE: DNA
<213> ORGANISM: Artificial Sequence
<220> FEATURE:
<223> OTHER INFORMATION: Synthetic sequence

<400> SEQUENCE: 38
atgggctggg ttcgtcaggc ccctggcaag gggctggagt gggtttccgc catctcc          57

<210> SEQ ID NO 39
<211> LENGTH: 117
<212> TYPE: DNA
<213> ORGANISM: Artificial Sequence
<220> FEATURE:
<223> OTHER INFORMATION: Synthetic sequence

<400> SEQUENCE: 39
tattacgctg acagcgtaaa gggaagattt acaattagcc gggataactc caaaaacacg          60
gtctatctcc agatgaacag cctcagggcc gaggacactg cagtgtatta ctgtgca          117

<210> SEQ ID NO 40

```
<211> LENGTH: 36
<212> TYPE: DNA
<213> ORGANISM: Artificial Sequence
<220> FEATURE:
<223> OTHER INFORMATION: Synthetic sequence

<400> SEQUENCE: 40
tatcgtggac aggggacgct ggtaactgtg agtagc                                          36

<210> SEQ ID NO 41
<211> LENGTH: 125
<212> TYPE: PRT
<213> ORGANISM: Artificial Sequence
<220> FEATURE:
<223> OTHER INFORMATION: Synthetic sequence

<400> SEQUENCE: 41

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Tyr Ser Arg Asp
            20                  25                  30

Thr Met Gly Trp Phe Arg Gln Ala Pro Gly Lys Glu Arg Glu Phe Val
        35                  40                  45

Ser Ala Ile Ser Ser Arg His Ser His Thr Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Glu Trp Asp Val Phe Asp Met His Tyr Ala Leu Pro Pro Met
            100                 105                 110

Trp Tyr Trp Gly Gln Gly Thr Gln Val Thr Val Ser Ser
        115                 120                 125

<210> SEQ ID NO 42
<211> LENGTH: 125
<212> TYPE: PRT
<213> ORGANISM: Artificial Sequence
<220> FEATURE:
<223> OTHER INFORMATION: Synthetic sequence

<400> SEQUENCE: 42

Glu Val Gln Leu Gln Ala Ser Gly Gly Gly Phe Val Gln Pro Gly Gly
1               5                   10                  15

Ser Leu Arg Leu Ser Cys Ala Ala Ser Gly Tyr Thr Ser Arg Ser Ser
            20                  25                  30

Ala Met Gly Trp Phe Arg Gln Ala Pro Gly Lys Glu Arg Glu Phe Val
        35                  40                  45

Ser Ala Ile Ser Asp Leu Thr Gly Tyr Pro Tyr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Ala Tyr Gln Asp Asp Lys Trp Thr Tyr Gly Ser Gln His Gly
            100                 105                 110

Lys Tyr Trp Gly Gln Gly Thr Gln Val Thr Val Ser Ser
        115                 120                 125
```

-continued

```
<210> SEQ ID NO 43
<211> LENGTH: 128
<212> TYPE: PRT
<213> ORGANISM: Artificial Sequence
<220> FEATURE:
<223> OTHER INFORMATION: Synthetic sequence

<400> SEQUENCE: 43

Glu Val Gln Leu Gln Ala Ser Gly Gly Gly Phe Val Gln Pro Gly Gly
1               5                   10                  15

Ser Leu Arg Leu Ser Cys Ala Ala Ser Gly Arg Thr Ser Trp Leu Thr
            20                  25                  30

Thr Met Gly Trp Phe Arg Gln Ala Pro Gly Lys Glu Arg Glu Phe Val
        35                  40                  45

Ser Ala Ile Ser Ser Phe Ser Ser Lys Gln Gly Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Tyr
                85                  90                  95

Cys Ala Tyr Ala Ser Tyr Pro Arg His Gln Gly Asn Gly Arg Trp Lys
            100                 105                 110

Asp Phe Val Glu Tyr Trp Gly Gln Gly Thr Gln Val Thr Val Ser Ser
            115                 120                 125

<210> SEQ ID NO 44
<211> LENGTH: 125
<212> TYPE: PRT
<213> ORGANISM: Artificial Sequence
<220> FEATURE:
<223> OTHER INFORMATION: Synthetic sequence

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Gly Tyr Ala Leu Asp
            20                  25                  30

Asp Met Gly Trp Val Arg Gln Ala Pro Gly Lys Gly Leu Glu Trp Val
        35                  40                  45

Ser Ala Ile Ser Asp Asp Glu Ser Met Ala Asp Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Ser Tyr Lys Glu Tyr Lys Tyr Gln Ser Gly His His Tyr Phe
            100                 105                 110

Ala Tyr Arg Gly Gln Gly Thr Leu Val Thr Val Ser Ser
        115                 120                 125

<210> SEQ ID NO 45
<211> LENGTH: 802
<212> TYPE: PRT
<213> ORGANISM: Homo sapiens

<400> SEQUENCE: 45

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
```

-continued

```
                    20                25                30
Cys Leu Ala Pro Ser Leu Glu Gln Gln Glu Gln Glu Leu Thr Val Ala
            35                40                45
Leu Gly Gln Pro Val Arg Leu Cys Cys Gly Arg Ala Glu Arg Gly Gly
        50                55                60
His Trp Tyr Lys Glu Gly Ser Arg Leu Ala Pro Ala Gly Arg Val Arg
65                70                75                80
Gly Trp Arg Gly Arg Leu Glu Ile Ala Ser Phe Leu Pro Glu Asp Ala
                85                90                95
Gly Arg Tyr Leu Cys Leu Ala Arg Gly Ser Met Ile Val Leu Gln Asn
            100               105               110
Leu Thr Leu Ile Thr Gly Asp Ser Leu Thr Ser Ser Asn Asp Asp Glu
        115               120               125
Asp Pro Lys Ser His Arg Asp Pro Ser Asn Arg His Ser Tyr Pro Gln
        130               135               140
Gln Ala Pro Tyr Trp Thr His Pro Gln Arg Met Glu Lys Lys Leu His
145               150               155               160
Ala Val Pro Ala Gly Asn Thr Val Lys Phe Arg Cys Pro Ala Ala Gly
            165               170               175
Asn Pro Thr Pro Thr Ile Arg Trp Leu Lys Asp Gly Gln Ala Phe His
            180               185               190
Gly Glu Asn Arg Ile Gly Gly Ile Arg Leu Arg His Gln His Trp Ser
            195               200               205
Leu Val Met Glu Ser Val Val Pro Ser Asp Arg Gly Thr Tyr Thr Cys
        210               215               220
Leu Val Glu Asn Ala Val Gly Ser Ile Arg Tyr Asn Tyr Leu Leu Asp
225               230               235               240
Val Leu Glu Arg Ser Pro His Arg Pro Ile Leu Gln Ala Gly Leu Pro
            245               250               255
Ala Asn Thr Thr Ala Val Val Gly Ser Asp Val Glu Leu Leu Cys Lys
            260               265               270
Val Tyr Ser Asp Ala Gln Pro His Ile Gln Trp Leu Lys His Ile Val
        275               280               285
Ile Asn Gly Ser Ser Phe Gly Ala Asp Gly Phe Pro Tyr Val Gln Val
        290               295               300
Leu Lys Thr Ala Asp Ile Asn Ser Ser Glu Val Glu Val Leu Tyr Leu
305               310               315               320
Arg Asn Val Ser Ala Glu Asp Ala Gly Glu Tyr Thr Cys Leu Ala Gly
            325               330               335
Asn Ser Ile Gly Leu Ser Tyr Gln Ser Ala Trp Leu Thr Val Leu Pro
            340               345               350
Glu Glu Asp Pro Thr Trp Thr Ala Ala Pro Glu Ala Arg Tyr Thr
            355               360               365
Asp Ile Ile Leu Tyr Ala Ser Gly Ser Leu Ala Leu Ala Val Leu Leu
        370               375               380
Leu Leu Ala Gly Leu Tyr Arg Gly Gln Ala Leu His Gly Arg His Pro
385               390               395               400
Arg Pro Pro Ala Thr Val Gln Lys Leu Ser Arg Phe Pro Leu Ala Arg
            405               410               415
Gln Phe Ser Leu Glu Ser Gly Ser Ser Gly Lys Ser Ser Ser Ser Leu
            420               425               430
Val Arg Gly Val Arg Leu Ser Ser Ser Gly Pro Ala Leu Leu Ala Gly
            435               440               445
```

```
Leu Val Ser Leu Asp Leu Pro Leu Asp Pro Leu Trp Glu Phe Pro Arg
    450             455             460
Asp Arg Leu Val Leu Gly Lys Pro Leu Gly Glu Gly Cys Phe Gly Gln
465             470             475             480
Val Val Arg Ala Glu Ala Phe Gly Met Asp Pro Ala Arg Pro Asp Gln
            485             490             495
Ala Ser Thr Val Ala Val Lys Met Leu Lys Asp Asn Ala Ser Asp Lys
            500             505             510
Asp Leu Ala Asp Leu Val Ser Glu Met Glu Val Met Lys Leu Ile Gly
    515             520             525
Arg His Lys Asn Ile Ile Asn Leu Leu Gly Val Cys Thr Gln Glu Gly
    530             535             540
Pro Leu Tyr Val Ile Val Glu Cys Ala Ala Lys Gly Asn Leu Arg Glu
545             550             555             560
Phe Leu Arg Ala Arg Arg Pro Pro Gly Pro Asp Leu Ser Pro Asp Gly
            565             570             575
Pro Arg Ser Ser Glu Gly Pro Leu Ser Phe Pro Val Leu Val Ser Cys
            580             585             590
Ala Tyr Gln Val Ala Arg Gly Met Gln Tyr Leu Glu Ser Arg Lys Cys
            595             600             605
Ile His Arg Asp Leu Ala Ala Arg Asn Val Leu Val Thr Glu Asp Asn
    610             615             620
Val Met Lys Ile Ala Asp Phe Gly Leu Ala Arg Gly Val His His Ile
625             630             635             640
Asp Tyr Tyr Lys Lys Thr Ser Asn Gly Arg Leu Pro Val Lys Trp Met
            645             650             655
Ala Pro Glu Ala Leu Phe Asp Arg Val Tyr Thr His Gln Ser Asp Val
            660             665             670
Trp Ser Phe Gly Ile Leu Leu Trp Glu Ile Phe Thr Leu Gly Gly Ser
            675             680             685
Pro Tyr Pro Gly Ile Pro Val Glu Glu Leu Phe Ser Leu Leu Arg Glu
    690             695             700
Gly His Arg Met Asp Arg Pro Pro His Cys Pro Pro Glu Leu Tyr Gly
705             710             715             720
Leu Met Arg Glu Cys Trp His Ala Ala Pro Ser Gln Arg Pro Thr Phe
            725             730             735
Lys Gln Leu Val Glu Ala Leu Asp Lys Val Leu Leu Ala Val Ser Glu
            740             745             750
Glu Tyr Leu Asp Leu Arg Leu Thr Phe Gly Pro Tyr Ser Pro Ser Gly
    755             760             765
Gly Asp Ala Ser Ser Thr Cys Ser Ser Ser Asp Ser Val Phe Ser His
    770             775             780
Asp Pro Leu Pro Leu Gly Ser Ser Ser Phe Pro Phe Gly Ser Gly Val
785             790             795             800
Gln Thr
```

SINGLE DOMAIN ANTIBODIES AND THEIR USE IN CANCER THERAPIES

SEQUENCE LISTING SUBMISSION VIA EFS-WEB

A computer readable text file, entitled "SequenceListing.txt" created on Jun. 12, 2023 with a file size of 21,048 bytes contains the sequence listing for this application and is hereby incorporated by reference in its entirety.

FIELD OF THE INVENTION

The present disclosure relates to anti-FGFR4 single domain antibodies (sdAb) and their use in diagnostic or in cancer therapy. Said anti FGFR4-sdAb can also further be included in chimeric antigen receptor and used in cancer cell therapy, notably cellular cancer therapy.

DETAILED DESCRIPTION

The Fibroblast Growth Factor Receptor 4 (FGFR4) belongs to the family of FGF receptors which also includes FGFR1, FGFR2 and FGFR3. Like the other members of the FGF receptor family, the transmembrane receptor FGFR4 contains a signal peptide, an extracellular ligand-binding domain (ECD), a transmembrane domain, an intracellular protein tyrosine kinase domain (TKD) and a C-terminal phosphorylation domain (Klint P et al., 1998). Similar to the other three FGFR members, the extracellular region of FGFR4 consists of three immunoglobulin-like domains (IgI, IgII, and IgIII), which are essential for specific ligand-binding.

As an important mediator of homeostasis in the liver, FGFR4 function is required for the maintenance of both lipid and glucose metabolism under normal dietary conditions, in addition to its established role in cholesterol (Huang X et al., Diabetes. 2007; 56:2501-2510). FGF6/FGFR4 pathway plays also an important role in myoblast differentiation and myotube regeneration (Floss T et al., Genes Dev. 1997; 11:2040-2051; Zhao P et al., Dev. Dyn. 2004; 229: 380-392).

FGFR4 is activated by FGF1, FGF2, FGF4, FGF6, FGF8 and FGF9 with decreasing efficiency (Ornitz et al., 1996); while all of these activate also other family members, FGF19 is specific for FGFR4 (Xie et al., 1999). Canonical FGFs bind to and activate FGFR4 with heparin/heparin sulfate (HS) (Lin B. C et al., J. Biol. Chem. 2007; 282: 27277-27284). As a specific ligand of FGFR4, FGF19 can bind and active FGFR4 with the 0-klotho (KLB) co-receptor. FGF19, as an endocrine ligand, has a more specific selective affinity to FGFR4 than other FGFR members (Ornitz D. M et al., J. Biol. Chem. 1996; 271:15292-15297; Zhang X et al., J. Biol. Chem. 2006; 281:15694-15700).

Fibroblast growth factor receptors (FGFRs) have been found to play a vital role in tumorigenesis and cancer progression through increased cell proliferation, metastasis, and survival (Babina I. S et al., Nat. Rev. Cancer. 2017; 17:318-332; Porta R et al., Crit. Rev. Oncol./Hematol. 2017; 113:256-267). Elevated FGFR4 has been tightly correlated with cancer development and progression, making it an attractive target to develop novel and effective anticancer therapeutics. Recently, one study evaluated the alterations of FGFR genes in a variety of cancer types (Helsten T et al., Clin. Cancer Res. 2016; 22:259-267), and showed that gene alterations of FGFRs occurred in 7.1% of 4853 solid tumors. Although the gene alteration is relatively low, FGFR4 overexpression has further been reported in many types of cancer. Increased FGFR4 mRNA expression has been detected in one-third of hepatocellular carcinoma (HCC) (Ho H. K et al., J. Hepatol. 2009; 50:118-127) and in 32% of breast cancer samples (Penault-Llorca F et al., Int. J. Cancer. 1995; 61:170-176). FGFR4 overexpression has also been observed in 64% of oropharyngeal squamous cell carcinoma and 41% of oral squamous cell carcinoma (Koole K et al., Pathobiology. 2015; 82:280-289). Overexpressed FGFR4 has also been found in pancreatic carcinomas and derived cell lines, which are mediated by an intronic enhancer activated by hepatic nuclear factor 1 alpha (Shah R. N et al., Oncogene. 2002; 21:8251-8261). Additionally, highly FGFR4 expression was detected in rhabdomyosarcoma (Taylor J. G et al., J. Clin. Investig. 2009; 119:3395-3407, see also Crose, L. E. S. et al. Clin. Cancer Res. 18, 3780-3790 (2012)).

The amplification of the FGF19 gene was found in liver cancer, breast cancer, lung cancer, bladder cancer, head and neck squamous cell carcinoma (HNSCC), and esophageal cancer (Huang X. et al, Proc. Natl. Acad. Sci. USA. 2002; 99:11369-11374; Sawey E. T. et al., Cancer Cell. 2011; 19:347-358; Tiong K. H. et al., Oncotarget. 2016; 7:57633; Zhang X. et al., Thorac. Cancer. 2017; 8:655-665; Hoover H. et al., J. Proteome Res. 2015; 14:3670-3679).

Mechanistic studies showed that phosphorylated FGFR4 recruits and phosphorylates two important intracellular targets, phospholipase γ (PLCγ) and FGFR substrate 2 (FRS2) [4]. MAPK then can be stimulated by activated protein kinase C (PKC) through PLCγ. Meanwhile, the MAPK and PI3K-AKT pathway can be triggered by activated FRS2 through recruitment of growth factor receptor bound 2 (GRB2). Upregulated activity of AKT and ERK1/2 leads to enhanced cell proliferation and survival in HCC upon the activation of FGF19/FGFR4 signaling. The FGF19-FGFR4 axis has further been linked to metastasis and poor survival (Touat M. et al., Clin. Cancer Res. 2015; 21:2684-2694).

Efforts have been focused on developing selective inhibitors to target FGFR4, which show particular promise as an anticancer monotherapy or an adjunct treatment. Three strategies have been notably developed to target FGFR4, including neutralizing antibodies, antisense oligonucleotides, and small molecule inhibitors.

However, inevitable on-target toxicities and off-target activity resulting from the use of nonspecific FGFR inhibitors lead to several adverse effects (Dieci M. V. et al., Cancer Discov. 2013; 3:264-279). Such disadvantages eventually limit their usage in cancer patients.

In order to provide further products for diagnostic and/or therapeutic applications it is thus highly desirable to have high affinity FGFR4 antibodies that bind specifically to the extracellular domain and block FGFR4 mediated signal transduction.

Thus, one of the technical problems underlying the present invention, was to provide novel FGFR4 antibodies and methods of use of the same which are suitable for diagnosing, preventing and/or treating diseases associated with FGFR4 expression. In particular, as single domain antibody scaffolds have many advantages for use in therapy such as better penetration in tissues, faster clearance in kidneys, high specificity or reduced immunogenicity, it is thus an objective of the present disclosure to provide high affinity single domain antibodies directed against FGFR4 that may be used in various therapeutic and diagnostic strategies.

Adoptive transfer of chimeric antigen receptor T-cell (CAR-T) therapy is typically one of the potential immunotherapies that have shown great promise for the treatment of hematologic malignancies in a series of dramatic successes in clinical trials. Unfortunately, the breakthrough with CAR-T cell therapy in the treatment of hematologic malignancies is still not well replicated in solid tumors (Y. Guo, Y et al., Chimeric antigen receptor-modified T cells for solid tumors: challenges and prospects, J Immunol Res, 2016; J. Li et al., Chimeric antigen receptor T cell (CAR-T) immunotherapy for solid tumors: lessons learned and strategies for moving forward; J Hematol Oncol, 11 (2018), p. 22). Furthermore, scFvs, which are mostly used in the design of chimeric antigen receptors exhibit a number of characteristics that may negatively impact on the therapeutic efficacy of CAR-Ts. Indeed, scFv are notably characterized by poor expression and stability and are prone to unfolding and aggregation. Thus, there remains a constant need to improve and diversify current therapeutic tools in oncology to cover not only the diversity of patient profiles but also the significant variability of tumours. This is particularly critical for aggressive tumours related to FGFR4 overexpression such as rhabdomyosarcoma.

SUMMARY OF THE INVENTION

The present application now provides synthetic humanized single domain antibodies specifically binding to FGFR4 with an affinity in the nano and picomolar range. These sdAb have further been shown to have the ability to block activation of the FGFR4 downstream MAPK pathway in FGFR4-mediated cancer cells and in particular in RMS cells. The inventors have further shown that liposome functionalized with said FGFR4 sdAb bind specifically to FGFR4 positive cancer cells and are internalized. These results provide strong evidence that FGFR4-targeted nanocarrier (and in particular liposomal) formulations, as per the present disclosure, represent a specific drug-delivery platform for FGFR4 overexpressing cancer cells, characterized by their rapid and specific receptor-mediated intracellular uptake. Lastly the inventors produced FGFR4-CAR T cells that were shown to mediate significant antitumor activity against FGFR4-expressing cancer cells in vitro, thus representing a promising targeted treatment option.

Thus, the present disclosure relates to a single domain antibody (sdAb) directed against FGFR4, wherein said humanized anti-FGFR4 sdAb has the following formula FRW1-CDR1-FRW2-CDR2-FRW3-CDR3-FRW4, and wherein the CDRs are selected from:

a CDR1 of SEQ ID NO:1; a CDR2 of SEQ ID NO:2 and
      a CDR3 of SEQ ID NO: 3,
    a CDR1 of SEQ ID NO: 4; a CDR2 of SEQ ID NO:5 and
      a CDR3 of SEQ ID NO:6,
    a CDR1 of SEQ ID NO: 7; a CDR2 of SEQ ID NO:8 and
      a CDR3 of SEQ ID NO:9,
    a CDR1 of SEQ ID NO:10; a CDR2 of SEQ ID NO:11
      and a CDR3 of SEQ ID NO:12, In some embodiments, the framework region consists of a FRW1 selected from SEQ ID NO:13 or SEQ ID NO: 17, a FRW2 selected from SEQ ID NO:14 or SEQ ID NO: 18, a FRW3 selected from SEQ ID NO:15 or SEQ ID NO: 19 a FRW4 selected from SEQ ID NO: 16 or SEQ ID NO: 20, or their functional variants with no more than 0, 1, 2 or 3 conservative amino acid substitutions in each of FRW1, FRW2, FRW3 and FRW4. In more specific embodiments, the framework region consists of a FRW1 of SEQ ID NO:13, a FRW2 of SED ID NO:14, a FRW3 of SEQ ID NO:15, a FRW4 of SEQ ID NO: 16, or FRW1 of SEQ ID NO:17, a FRW2 of SED ID NO:18, a FRW3 of SEQ ID NO:19, and aW FR4 of SEQ ID NO: 20, or their functional variants with no more than 0, 1, 2 or 3 conservative amino acid substitutions in each of FRW1, FRW2, FRW3 and FRW4.

In even more particular embodiments, the present disclosure contemplates humanized anti-FGFR4 sdAb having a sequence set forth in any one SEQ ID NO:41, SEQ ID NO:42, SEQ ID NO:43, and SEQ ID NO:44.

The humanized anti-FGFR4 sdAb of the present disclosure can be linked directly or indirectly, covalently or non-covalently to a compound of interest selected from a nucleic acid, a polypeptide or a protein, a virus, a toxin and a chemical entity. In some embodiments, the humanized anti-FGFR4 sdAb is linked directly or indirectly, covalently or non-covalently to a diagnostic compound selected from an enzyme, a fluorophore, a NMR or MRI contrast agent, a radioisotope and a nanoparticle. In some embodiments, the humanized anti-FGFR4 sdAb is linked directly or indirectly, covalently or non-covalently to a compound selected from cytotoxic agents, chemotherapeutic agents, radioisotopes, targeted anti-cancer agents, immunotherapeutic agents (such as immunosuppressants or immune stimulators), and lytic peptides. In some embodiments, the humanized anti-FGFR4 sdAb is linked directly or indirectly, covalently or non-covalently to a drug nanocarrier, optionally an organic nanocarrier. Typically, the organic nanocarrier can be selected from polymeric nanoparticles, liposomes, micelles and protein-based nanocarrier such as albumin.

The FGFR4 sdAb can also be fused to an immunoglobulin domain, in particular to an Fc domain.

The present disclosure also encompasses multispecific binding compounds comprising at least a first sdAb consisting in the FGFR4 sdAb as herein described, and further comprising another sdAb binding to a second antigen, optionally wherein, the first sdAb is located at the N-terminus of the second sdAb or wherein the first sdAb is located at the C-terminus of the second sdAb.

The present disclosure also encompasses a chimeric antigen receptor (CAR) comprising (a) an antigen binding domain comprising at least a first sdAb consisting in the FGFR4 sdAb as herein defined and optionally a second sdAb specifically binding to a second antigen, (b) a transmembrane domain; and (c) an intracellular domain.

Typically, the second antigen is selected from the group consisting of PSMA, PSCA, BCMA, CS1, GPC3, CSPG4, EGFR, fetal acetylcholine receptor gamma subunit gamma (fAChRγ), HER3, IGF1R, SLC19A1, ACVR2A, EPHB4, CA125, IL-13R, CD278, CD123, NCAM, 5T4, CD2, CD3, CD16 (FcγRIII), CD23, MART-1, L1 CAM, MUC16, ROR1, SLAMF7, cKit, CD38, CD53, CD56, CD71, CD74, CD92, CD100, CD123, CD138, CD148, CD150, CD200, CD261, CD262, CD276, CD362, gp100, ROR1, mesothelin, CD33/IL3Ra, c-Met, Glycolipid F77, EGFRvIII, GD-2, NKp46 receptor, NY-ESO-1 TCR or MAGE A3 TCR, human telomerase reverse transcriptase (hTERT), survivin, cytochrome P450 1 B1 (CY1 B), HER2, Wilm's tumor gene 1 (WT1), livin, alphafetoprotein (AFP), carcinoembryonic antigen (CEA), mucin 16, MUC1, p53, cyclin, an immune checkpoint target or combinations thereof.

The transmembrane domain can be selected from the transmembrane domain of cell surface-targeted protein including the CD3zeta transmembrane domain, the CD28 transmembrane domain, the CD8 alpha transmembrane domain, the DAP10 transmembrane domain, or the DAP12 transmembrane domain.

The intracellular domain can comprise one or more domains derived from the CD28, the OX40, the CD3zeta, the 4-1BB, the DAP10 and/or the DAP12 intracellular domains.

The present disclosure also encompasses an isolated nucleic acid comprising a nucleic acid sequence encoding the humanized anti-FGFR4 sdAb or the CAR as herein described which is advantageously linked to a heterologous regulatory control sequence.

The present disclosure also encompasses vectors comprising the nucleic acids as herein disclosed, host cells comprising thereof, isolated cells or population of cells expressing the humanized anti-FGFR4 sdAb, or the CAR as herein disclosed. Typically said cells are allogenic or autologous cell and can be elected from macrophages, NK cells and T cells, notably CD4+/CD8+, TILs/tumor derived CD8 T cells, central memory CD8+ T cells, Treg, MAIT, and Yδ T cell.

The therapeutic product of the present disclosure, including the humanized anti-FGFR4 sdAb, the CAR, the nucleic acid, the vector, the host cell, the isolated cell or cell population as defined can be use in therapy, notably in the treatment of cancer. They can be used in particular in cellular therapy of cancer and/or in combination with other therapy (notably other cancer therapies such as a chemotherapeutic agent, and/or an immunotherapeutic agent, notably one or more checkpoint inhibitors).

Lastly the present disclosure includes the use of humanized anti-FGFR4 sdAb as previously defined for molecular imaging, notably for the detection or monitoring of an FGFR4-mediated cancer. Is in particular described herein, an in vitro or ex vivo method for diagnosing or monitoring an FGFR4 mediated cancer in a subject comprising the steps of:
- a) Contacting in vitro an appropriate sample from said subject with a diagnostic agent as previously defined, and
- b) Determining the expression of FGFR4 in said sample.

DETAILED DESCRIPTION

Definitions

The terminology used herein is for the purpose of describing particular embodiments only and is not intended to be exhaustive. It must be noted that, as used in the specification and the appended claims, the singular forms "a," "an" and "the" include plural referents unless the context clearly dictates otherwise.

The term "comprising" as used herein is synonymous with "including" or "containing" and is inclusive or open-ended and does not exclude additional, uncited members, elements or method steps.

Unless specifically stated or obvious from context, as used herein, the term "about" is to be understood as within a range of normal tolerance in the art, for example within 2 standard deviations of the mean. About can be understood as within 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the term "isolated" refers to a substance or entity that has been (1) separated from at least some of the components with which it was associated when initially produced (whether in nature or in an experimental setting), and (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The "isolated" products of the present disclosure, including isolated nucleic acids, proteins, polypeptides, and antibodies are not products of nature (i.e., "non-naturally occurring"). Rather, the "isolated" nucleic acids, proteins, polypeptides, and antibodies of the present disclosure are "man-made" products. The "isolated" products of the present disclosure can be "markedly different" or "significantly different" from products of nature. By way of a non-limiting example, the isolated nucleic acids may be purified, recombinant, synthetic, labeled, and/or attached to a solid substrate. Such nucleic acids can be markedly different or significantly different than nucleic acids that occur in nature. By way of further non-limiting example, the "isolated" proteins, polypeptides, and antibodies of the present disclosure may be purified, recombinant, synthetic, labeled, and/or attached to a solid substrate. Such proteins, polypeptides, and antibodies can be markedly different or significantly different from proteins, polypeptides, and antibodies that occur in nature.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The nucleic acid (also referred to as polynucleotides) may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, inter-nucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

A "synthetic" RNA, DNA or a mixed polymer is one created outside of a cell, for example one synthesized chemically.

The term "nucleic acid fragment" as used herein refers to a nucleic acid sequence that has a deletion, e.g., a 5'-terminal or 3'-terminal deletion compared to a full-length reference nucleotide sequence. In an embodiment, the nucleic acid fragment is a contiguous sequence in which the nucleotide sequence of the fragment is identical to the corresponding positions in the naturally-occurring sequence. In some embodiments, fragments are at least 10, 15, 20, or 25 nucleotides long, or at least 20, 30, 40, 50, 60, 70, 80, 90, 100, 1 10, 120, 130, 140, or 150 nucleotides long. In some embodiments a fragment of a nucleic acid sequence is a fragment of an open reading frame sequence. In some embodiments such a fragment encodes a polypeptide fragment (as defined herein) of the protein encoded by the open reading frame nucleotide sequence.

The nucleic acid can be purified. Preferably, the purified nucleic acid is more than 50%, 75%, 85%, 90%, 95%, 97%, 98%, or 99% pure. Within the context of the present disclosure, a purified nucleic acid that is at least 50% pure means a purified nucleic acid sample containing less than 50% other nucleic acids. For example, a sample of a plasmid can be at least 99% pure if it contains less than 1% contaminating bacterial DNA.

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof. Further, a polypeptide may comprise a number of different domains each of which having one or more distinct activities. For the avoidance of doubt, a "polypeptide" may be any length greater two amino acids.

The term "peptide" as used herein refers to a short polypeptide, e.g., one that typically contains less than about 50 amino acids and more typically less than about 30 amino acids. The term as used herein encompasses analogs and mimetics that mimic structural and thus biological function.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from a cell in which it was synthesized.

The protein or polypeptide can be purified. Preferably, the purified protein or polypeptide is more than 50%, 75%, 85%, 90%, 95%, 97%, 98%, or 99% pure. Within the context of the present disclosure, a purified protein that is more than 50% (etc.) pure means a purified protein sample containing less than 50% (etc.) other proteins. For example, a sample of a protein comprising can be 99% pure if it contains less than 1% contaminating host cell proteins.

The term "polypeptide fragment" as used herein refers to a polypeptide that has a deletion, e.g., an amino-terminal and/or carboxy-terminal deletion compared to a full-length polypeptide, such as a naturally occurring protein. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino acids long, or at least 20 amino acids long, or at least 25, 30, 35, 40 or 45, amino acids, or at least 50 or 60 amino acids long, or at least 70 amino acids long, or at least 100 amino acids long.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 91% 92%, 93%, 94%, 95%, 96%, 97%, 98% or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89: 10915) alignments (B) of 50, expectation (E) of 10, M=5, N=−4, and a comparison of both strands. The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4: 11-17, 1988) which has been incorporated into the ALIGN program (version 2.0) using a PAM120 weight residue table, a gap length penalty of 12 and a gap penalty of 4. In addition, the percent identity between two amino acid sequences can be determined using the Needleman and Wunsch, J. Mol. Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

As used herein a "functional variant" or a given protein includes the wild-type version of said protein, a variant protein belonging to the same family, an homolog protein, or a truncated version, which preserves the functionality of the given protein. Typically the functional variant exhibit at least 70%, 75%, 80%, 85%, 90%, 95%, 97%, 98%, or 99% amino acid identity with the given protein.

As used herein, the term "mammal" refers to any member of the taxonomic class mammalian, including placental mammals and marsupial mammals. Thus, "mammal" includes humans, primates, livestock, and laboratory mammals. Exemplary mammals include a rodent, a mouse, a rat, a rabbit, a dog, a cat, a sheep, a horse, a goat, a llama, cattle, a primate, a pig, and any other mammal. In some embodiments, the mammal is at least one of a transgenic mammal, a genetically-engineered mammal, and a cloned mammal.

According to the present disclosure, the term "disease" refers to any pathological state, including cancer diseases, in particular those forms of cancer diseases described herein.

The term "normal" refers to the healthy state or the conditions in a healthy subject or tissue, i.e., non-pathological conditions, wherein "healthy" preferably means non-cancerous.

The term "malignancy" refers to a non-benign tumor or a cancer. As used herein, the term "cancer" includes a malignancy characterized by deregulated or uncontrolled cell growth.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

Cancers are classified by the type of cell that resembles the tumor and, therefore, the tissue presumed to be the origin of the tumor. These are the histology and the location, respectively.

The term "cancer" according to the disclosure comprises notably leukemias, seminomas, melanomas, teratomas, lymphomas, neuroblastomas, gliomas and sarcomas. The term cancer notably include rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer, soft tissue tumors and the metastases thereof. The term cancer according to the present disclosure also comprises cancer metastases and relapse of cancer.

"Growth of a tumor" or "tumor growth" according to the present disclosure relates to the tendency of a tumor to increase its size and/or to the tendency of tumor cells to proliferate.

For purposes of the present disclosure, the terms "cancer" and "cancer disease" are used interchangeably with the terms "tumor" and "tumor disease".

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject. In particular, the term "treatment of a disease" includes curing, shortening the duration, ameliorating, preventing, slowing down or inhibiting progression or worsening, or preventing or delaying the onset of a disease or the symptoms thereof.

The therapeutically active agents or product, vaccines and compositions described herein may be administered via any conventional route, including by injection or infusion.

The agents described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount of an agent described herein will depend on the condition to be treated, the severity of the disease, the individual parameters of the patient, including age, physiological condition, size and weight, the duration of treatment, the type of an accompanying therapy (if present), the specific route of administration and similar factors. Accordingly, the doses administered of the agents described herein may depend on several of such parameters. In the case that a reaction in a patient is insufficient with an initial dose, higher doses (or effectively higher doses achieved by a different, more localized route of administration) may be used.

The pharmaceutical compositions as herein described are preferably sterile and contain an effective amount of the therapeutically active substance to generate the desired reaction or the desired effect.

The pharmaceutical compositions as herein described are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible.

Single Domain Antibodies and Variants Thereof

As used herein, the term "FGFR4" has its general meaning in the art and includes human FGFR4 (also named "Fibroblast growth factor receptor 4"), in particular the native-sequence polypeptide, isoforms, chimeric polypeptides, all homologs, fragments, and precursors of human FGFR4. The amino acid sequence for native FGFR4 includes the UniProt reference P22455 (FGFR4_HUMAN).

More specifically the term "FGFR4" includes the human FGFR4 of the following SEQ ID:45.

```
>sp|P22455|FGFR4_HUMAN Fibroblast growth factor
receptor 4 OS = Homo sapiens OX = 9606 GN = FGFR4
PE = 1 SV = 2
MRLLLALLGVLLSVPGPPVLSLEASEEVELEPCLAPSLEQQEQELTVALG

QPVRLCCGRAERGGHWYKEGSRLAPAGRVRGWRGRLEIASFLPEDAGRYL

CLARGSMIVLQNLTLITGDSLTSSNDDEDPKSHRDPSNRHSYPQQAPYWT

HPQRMEKKLHAVPAGNTVKFRCPAAGNPTPTIRWLKDGQAFHGENRIGGI

RLRHQHWSLVMESVVPSDRGTYTCLVENAVGSIRYNYLLDVLERSPHRPI

LQAGLPANTTAVVGSDVELLCKVYSDAQPHIQWLKHIVINGSSFGADGFP

YVQVLKTADINSSEVEVLYLRNVSAEDAGEYTCLAGNSIGLSYQSAWLTV

LPEEDPTWTAAAPEARYTDIILYASGSLALAVLLLLAGLYRGQALHGRHP

RPPATVQKLSRFPLARQFSLESGSSGKSSSSLVRGVRLSSSGPALLAGLV

SLDLPLDPLWEFPRDRLVLGKPLGEGCFGQVVRAEAFGMDPARPDQASTV

AVKMLKDNASDKDLADLVSEMEVMKLIGRHKNIINLLGVCTQEGPLYVIV

ECAAKGNLREFLRARRPPGPDLSPDGPRSSEGPLSFPVLVSCAYQVARGM

QYLESRKCIHRDLAARNVLVTEDNVMKIADFGLARGVHHIDYYKKTSNGR

LPVKWMAPEALFDRVYTHQSDVWSFGILLWEIFTLGGSPYPGIPVEELFS

LLREGHRMDRPPHCPPELYGLMRECWHAAPSQRPTFKQLVEALDKVLLAV

SEEYLDLRLTFGPYSPSGGDASSTCSSSDSVFSHDPLPLGSSSFPFGSGV

QT
```

The term "antibody", broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and lgA2) or subclass.

An antibody fragment is a portion of an antibody, for example as F(ab')2, Fab, Fv, sFv and the like. Functional fragments of a full length antibody retain the target specificity of a full length antibody. Recombinant functional antibody fragments, such as Fab (Fragment, antibody), scFv (single chain variable chain fragments) and single domain antibodies (dAbs) have therefore been used to develop therapeutics as an alternative to therapeutics based on mAbs. scFv fragments (~25 kDa) consist of the two variable domains, VH and VL. Naturally, VH and VL domains are non-covalently associated via hydrophobic interaction and tend to dissociate. However, stable fragments can be engineered by linking the domains with a hydrophilic flexible linker to create a single chain Fv (scFv). The smallest antigen binding fragment is the single variable fragment, namely the VH or VL domain. Binding to a light chain/heavy chain partner respectively is not required for target binding. Such fragments are used in single domain antibodies. A single domain antibody (−12 to 15 kDa) therefore has either the VH or VL domain.

As used herein the term "single-domain antibody" (sdAb) or Nanobody® (tradename of Ablynx). has its general meaning in the art and refers to an antibody fragment with a molecular weight of only 12-15 kDa consisting of a single monomeric variable antibody domain derived from a heavy chain. Such single domain antibody (named VHH) can be found in Camelid mammals and are naturally devoid of light chains. For a general description of (single) domain antibodies, reference is also made to the prior art cited above, as well as to EP 0 368 684, Ward et al. (Nature 1989 Oct. 12; 341 (6242): 544-6), Holt et al, Trends Biotechnol, 2003, 21(1 1):484-490; and WO 06/030220, WO 06/003388. The amino acid sequence and structure of a single-domain antibody can be considered to be comprised of four framework regions or "FRWs" which are referred to in the art and herein as "Framework region 1" or "FRW1"; as "Framework region 2" or "FRW2"; as "Framework region 3" or "FRW3"; and as "Framework region 4" or "FRW4" respectively; which framework regions are interrupted by three complementary determining regions or "CDRs", which are referred to in the art as "Complementary Determining Region 1" or "CDR1"; as "Complementarity Determining Region 2" or "CDR2" and as "Complementarity Determining Region 3" or "CDR3", respectively. Accordingly, the single-domain antibody can be defined as an amino acid sequence with the general structure: FRW1-CDR1-FRW2-CDR2-FRW3-CDR3-FRW4 in which FRW1 to FRW4 refer to framework regions 1 to 4 respectively, and in which CDR1 to CDR3 refer to the complementarity determining regions 1 to 3. In the context of the present disclosure, the amino acid residues of the single-domain antibody are numbered according to the general numbering for VH domains given by the International ImMunoGeneTics information system aminoacid numbering.

An "isolated sdAb", as used herein, refers to a single domain antibody (sdAb) that is substantially free of other antibodies, notably other sdAb having different antigenic specificities (e.g., an isolated antibody that specifically binds to FGFR4 is substantially free of antibodies that specifically bind to other antigens than FGFR4). Moreover, an isolated antibody may be substantially free of other cellular material and/or chemicals.

As used herein, the term "synthetic" means that such antibody has not been obtained from fragments of naturally occurring antibodies but produced from recombinant nucleic acids comprising artificial coding sequences.

The term "CDR" refers to the complementarity-determining region within antibody variable sequences. There are three CDRs in each of the variable regions of the heavy chain and the light chain, which are designated CDR1, CDR2 and CDR3, for each of the variable regions. The term "CDR set" refers to a group of three CDRs that occur in a single variable region capable of binding the antigen. The exact boundaries of these CDRs have been defined differently according to different systems. The system described by Kabat is used herein. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242).

sdAb affinity refers to the strength with which the sdAb binds to the epitope presented on an antigen, such as a FGFR4 in the present disclosure, through its antigen-binding site (paratope). Affinity may be assessed based on assessment of the $K_D$ value.

The term "$K_D$", as used herein, is intended to refer to the equilibrium dissociation constant, which is obtained from the ratio of $k_{off}$ to $k_{on}$ (i.e. $k_{off}/k_{on}$) and is expressed as a molar concentration (M). The $K_D$ value relates to the concentration of antibody (the amount of antibody needed for a particular experiment) and so the lower the $K_D$ value (lower concentration) and thus the higher the affinity of the antibody. $K_D$ values for antibodies can be determined using methods well established in the art. Methods for determining the $K_D$ values of mAbs can be found in Harlow et al., Antibodies: A Laboratory Manual, Cold Spring Harbor Laboratory Press, Cold Spring Harbor, N.Y., 1988; Coligan et al., eds., Current Protocols in Immunology, Greene Publishing Assoc. and Wiley Interscience, N.Y., 1992, 1993, and Muller, Meth. Enzymol. 92:589-601, 1983, which references are entirely incorporated herein by reference. A method for determining the $K_D$ of an antibody is by using surface plasmon resonance, or by using a biosensor system such as a Biacore® (see also for detailed information regarding affinity assessment Rich R L et al., Anal Biochem, 2001, but also for more details about the specific implementation of affinity measurement for sdAb Moutel S et al., eLife 2016; 5:e16228). Affinity measurements are generally performed at 25° C. The terms "$k_{assoc}$" or "ka", or "$k_{on}$" as used herein, is intended to refer to the association rate of a particular antibody-antigen interaction, whereas the terms "$k_{dis}$" or "kd,", or $k_{off}$ as used herein, is intended to refer to the dissociation rate of a particular antibody-antigen interaction. Briefly, as sdAb are smaller proteins that their respective antigens, they can be capture on a sensorship from a Biocore biosensor instrument, while the recombinant antigens (i.e., typically rFGFR4) can be used as analytes. Analytes can be injected sequentially with increased concentration ranging for example between 3.125 nM to 50 nM in a single cycle without regeneration of the sensorship between injections. Binding parameters can be obtained by fitting the overlaid sensorgrams with the 1:1. Langmuir binding model of the BIAevalutation software.

Typically, a single domain antibody as per the present disclosure binds to FGFR4, notably human FGFR4 as herein defined with a $K_D$ with a $K_D$ binding affinity of about $10^{-6}$ M or less, $10^{-7}$ M or less, $10^{-8}$ M or less, $10^{-9}$ M or less, $10^{-10}$ M or less, or $10^{-11}$ M or less. In some embodiments, the $K_D$ binding affinity is in the nano/pico-molar range, notably comprised between $10^{-7}$ and $10^{-12}$ M, notably between $10^{-8}$ and $10^{-12}$, in particular between $10^{-8}$ and $10^{-10}$.

The inventors have isolated 4 reference single-domain antibodies (sdAb) with the required properties, notably the required affinity and characterized by following sequences:

TABLE 1

Full sdAb sequences.

| sdAb (No) | FR1 | CDR1 | FR2 | CDR2 | FR3 | CDR3 | FR4 |
|---|---|---|---|---|---|---|---|
| A8 | EVQLQASGG GFVQPGGSL RLSCAASG | RT YS RD T | MGWFRQA PGKEREFV SAIS | SR HS HT T | YYADSVKGRFTISRDN SKNTVYLQMNSLRAE DTATYYCA | EWD VFD MHY ALPP MW | YWGQ GTQVT VSS |
| B1 | EVQLQASGG GFVQPGGSL RLSCAASG | YT SR SS A | MGWFRQA PGKEREFV SAIS | DL TG YP Y | YYADSVKGRFTISRDN SKNTVYLQMNSLRAE DTATYYCA | AYQ DDK WTY GSQ HGK | YWGQ GTQVT VSS |
| B5 | EVQLQASGG GFVQPGGSL RLSCAASG | RT WL TT | MGWFRQA PGKEREFV SAIS | SFS SK QG | YYADSVKGRFTISRDN SKNTVYLQMNSLRAE DTATYYCA | YAS YPRH QGN GRW KDF VE | YWGQ GTQVT VSS |
| F8 | *AEVQLVESGG GLVQPGGSL RLSCAASG* | *TG YA LD D* | *MGWVRQA PGKGLEWV SAIS* | *DD ES MA D* | *YYADSVKGRFTISRDNSK NTVYLQMNSLRAEDTAV YYCA* | *SYKE YKY QSG HHY FA* | *YRGQG TLVTVS S* |

Therefore, the present disclosure encompasses single domain antibodies having at least the 3 CDRs of one of the 4 reference single domain antibodies as defined in table 1.

In some embodiments, sdAbs according to the present disclosure include sdAbs having at least 60, 70, 80, 90, 95, 96, 97, 98, 99 or 100 percent identity with the amino acid sequences as set forth in any one of SEQ ID NO:41-44.

sdAb as per the present disclosure notably include humanized anti-FGFR4 SdAbs having framework region sequences that have at least 60, 70, 80, 90, 95, 96, 97, 98, 99 or 100 percent identity with one or more of the sequences SEQ ID NO:13-20.

The 3 CDR regions of humanized anti-FGFR4 sdAbs as herein disclosed can be 100% identical to the 3 CDR regions of one of the reference humanized sdAbs (hsdAbs) as defined in table 1. Alternatively, in some embodiments, hsdAbs according to the present disclosure may have an amino acid sequence that have been mutated by amino acid deletion, insertion or substitution, yet that have at least 60, 70, 80, 90, 95, 96, 97, 98, 99 or 100 percent identity in the CDR regions compared with the CDR regions of the sdAb of table 1. Typically, as per the present disclosure, antibodies may have between 1, 2, 3 or 4 amino acid variations (including deletion, insertion or substitution) in one or more CDRs, as compared to the respective CDR sequences of the sdAb of the table 1.

In some embodiments, the single domain antibody of the present disclosure is a mutant variant of one of the reference single domain antibodies of table 1, having the 3 CDR regions 100% identical to the corresponding 3 CDR regions of said reference sdAb, and wherein no more than 1, 2, 3, 4 or 5 amino acids have been mutated by amino acid deletion, insertion or substitution in one or more of the FRW1, FRW2, FRW3 and/or FRW4 regions, when compared with the corresponding framework regions of the corresponding reference sdAb.

In some embodiments, an sdAb of the present disclosure is selected from SEQ ID NOs. 41-44 having one or more amino acid substitutions, deletions, insertions or other modifications compared to SEQ ID NOs. 41-44, and which retains a biological function of the single domain antibody. Modifications may include one or more substitution, deletion or insertion of one or more codons encoding the single domain antibody or polypeptide that results in a change in the amino acid sequence as compared with the sequence of the reference single domain antibody or polypeptide. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

In some embodiments, the modification is a conservative sequence modification. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into single domain antibody as herein described by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of a single domain antibody of the present disclosure can be replaced with other amino acid residues from the same side chain family and the altered antibody can be tested for retained function (i.e., the functions set forth in (c) through (I) above) using the functional assays described herein.

In some embodiments, the single domain antibody is selected from one of the SEQ ID NOs. 41-44, but comprises one or more amino acid substitutions, for example 1 to 20, such as 1, 2, 3, 4, 5, 6, 7, 8, 9 or 10 amino acid substitutions. The one or more amino acid substitution can be in one or more of the framework areas. Alternatively, or in addition, the one or more amino acid substitution can be in one or more of the CDRs. In some embodiments, the amino acid substitutions are in the framework and CDR sequences.

In some embodiments, the humanized single domain antibody is a variant of a single domain antibody selected from those having SEQ ID NOs. 41-44, that comprises one or more sequence modification and has improvements in one or more of a property such as binding affinity, specificity, thermostability, expression level, effector function, glycosylation, reduced immunogenicity, or solubility as compared to the unmodified single domain antibody.

In preferred embodiments, a sdAb according to the present disclosure has strict specificity for FGFR4. By having strict specificity for FGFR4, it is herein intended that the sdA according to the present disclosure show no detectable binding to other FGFR molecules such as FGFR1, FGFR2, or FGFR3. Binding assay can be performed as illustrated in the results by detecting sdAb binding to cell expressing of not the various FGFR molecules at their surface. Typically, the assay can be performed by flow cytometry using a labelled (for example a FITC-labelled anti-iXHis-tag antibody) to detect surface-bound single domain antibodies.

In some embodiments, a sdAb

Typically, a single domain antibody as per the present disclosure has an affinity ($K_D$) for FGFR4 which is at least of $10^{-7}$, notably at least of $10^{-8}$, at least of $10^{-9}$ M, while having no affiniy, or a vely low affinity for other FGFR molecules (such as FGFR1, FGFR2 and/or FGFR3) of less than $10^{-3}$ M. In some embodiment an sdAb specific for FGFR4 has no affinity for FGFR1 and FGFR3 while preserving a high affinity (between $1\cdot10^6$ and $1\cdot10^8$, notably between $1\cdot10^6$ and $1\cdot10^7$) for FGFR2.

In preferred embodiments, sdAb as per the present disclosure inhibit FGFR4 signalling. Analysis of this properties can be performed as illustrated in the results enclosed herein. Typically, FGFR4 activation assay can be performed on Rh30 cells and ERK1:2 phosphorylation used as a read-out. Rh30 cells can thus be incubated with FG19 the specific ligand for FGFR4 with or without the antibody to be tested. Increase of phosphor ERK1/2 levels means that the tested antibody activates FGFR4 downstream pathway as per the present disclosure.

A skilled person will know that there are different ways to identify, obtain and optimise the antigen binding molecules as described herein, including in vitro and in vivo expression libraries. Optimisation techniques known in the art, such as display (e.g., ribosome and/or phage display) and/or mutagenesis (e.g., error-prone mutagenesis) can be used. The present disclosure therefore also comprises sequence optimised variants of the single domain antibodies described herein.

In some embodiments of the present disclosure, an isolated humanized single domain antibody as herein described can be linked directly or not, covalently or not to a compound of interest. The substance or compound of interest as defined above can be directly and covalently or non-covalently linked to a single domain antibody as herein defined either to one of the terminal ends (N or C terminus), or to the side chain of one of the amino acids of said single domain antibody. The substance of interest can also be indirectly and covalently or non-covalently linked to said single domain antibody by means of a spacer (or linker) either to one of the terminal ends of said single domain antibody, or to a side chain of one of the amino acids of said single domain antibody. Conventional linking methods of a substance of interest to a peptide, in particular an antibody, are known in the art (e.g., See Ternynck and Avrameas 1987 "Techniques immunoenzymatiques" Ed. INSERM, Paris; Hermanson, 2010, Bioconjugate Techniques, Academic Press).

In some embodiments, single domain antibodies as herein described can be notably in the form of "antibody drug conjugate" of the formula sdAb-(L-(D)m)n or a pharmaceutically acceptable salt thereof; wherein sdAb is a single domain antibody as previously disclosed; L is a linker; D is a compound of interest; m is an integer from 1 to 8; and n is an integer from 1 to 10, typically 3 or 4.

The term "antibody drug conjugate" as used herein refers to the linkage of a single domain antibody with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the immunoconjugate. The linker (L) can be for example selected from the group consisting of a cleavable linker, a non-cleavable linker, a hydrophilic linker, a procharged linker and a dicarboxylic acid-based linker.

In some embodiments, the single domain antibody of the present disclosure is conjugated, or covalently linked to the compound of interest. As used herein, the term "conjugation" has its general meaning in the art and means a chemical conjugation, or chemical crosslinking. Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on polypeptide cross-linking and conjugate preparation is: WONG, Chemistry of protein conjugation and cross-linking, CRC Press (1991), see also Amon et al., "Monoclonal Antibodies For Immunotargeting Of Drugs In Cancer Therapy," in Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62: 119-58. See also, e.g., PCT publication WO 89/12624.). Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Haider, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106.; Junutula, J. R., Flagella, K. M., Graham, R. A., Parsons, K. L., Ha, E., Raab, H., Bhakta, S., Nguyen, T., Dugger, D. L., Li, G., et al. (2010) Engineered thio-trastuzumab-DM1 conjugate with an improved therapeutic index to target human epidermal growth factor receptor 2-positive breast cancer. Clin. Cancer Res. 16, 4769-4778.). Junutula et al. (2008) developed cysteine-based site-specific conjugation called "THIO-MABs" (TDCs) that are claimed to display an improved therapeutic index as compared to conventional conjugation methods. In particular the one skilled in the art can also envisage a polypeptide engineered with an acyl donor glutamine-containing tag (e.g., Gln-containing peptide tags or Q-tags) or an endogenous glutamine that are made reactive by polypeptide engineering (e.g., via amino acid deletion, insertion, substitution, or mutation on the polypeptide). Then a transglutaminase, can covalently crosslink with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882). The term "transglutaminase", used interchangeably with "TGase" or "TG", refers to an enzyme capable of cross-linking proteins through an acyl-transfer reaction between the $\gamma$-carboxamide group of peptide-bound glutamine and the $\varepsilon$-amino group of a lysine or a structurally related primary amine such as amino pentyl group, e.g. a peptide-bound lysine, resulting in a $\varepsilon$-($\gamma$-glutamyl) lysine isopeptide bond. TGases include, inter alia, bacterial transglutaminase (BTG) such as the enzyme having EC reference EC 2.3.2.13 (protein-glutamine-$\gamma$-glutamyltransferase). In some embodiments, the single domain antibody of the present disclosure is conjugated to the heterologous moiety by a linker molecule. As used herein, the term "linker molecule" refers to any molecule attached to the single domain antibody the present disclosure. The attachment is typically covalent. In some embodiments, the linker molecule is flexible and does not interfere with the binding of the single domain antibody the present disclosure.

A compound or substance of interest as herein intended can be non-limitatively selected from a nucleic acid, a polypeptide or a protein, a virus, a toxin and a chemical entity.

In some embodiments, compounds of interest include antigen binding domain agents such as antibodies, variants and fragments thereof, notably the same or another single domain antibody, aptamers, or enzymes.

The compound or substance of interest, as above described, can be a therapeutic or a diagnostic compound. Therapeutic compounds notably include therapeutic compounds having anti-cancer and/or cytotoxic activity (i.e. cytotoxic compounds), and diagnostic compounds typically include imaging probes.

Chemotherapeutic drugs often lack specificity and can also affect healthy tissues. To overcome this problem, nano vehicles can be used to deliver drugs actively to the tumor site. The use of nanotechnology in the field of chemotherapy has the potential to improve biodistribution by increasing drug concentrations at the tumor site and reduce toxicity to normal cells (see Ferrari, M. Cancer nanotechnology: Opportunities and challenges. Nat. Rev. Cancer 5, 161-171 (2005); and Kumari, P., Ghosh, B. & Biswas, S. Nanocarriers for cancer-targeted drug delivery. J. Drug Target. 24, 179-191 (2016) for detailed reviews). Thus, in some embodiments, said substance of interest is a drug nanocarrier, that can be organic such as liposomes or a polymeric entities or inorganic comprising, or encapsulating, a diagnostic or therapeutic compound (Villaraza et al. 2010 Chem Rev., 110, 2921-2959). Hence, nanobodies are very convenient tools for delivering toxic cargos to cancer cells and are well-suited for chemical conjugation onto different nanoparticle or nanocarrier formats. Organic carriers (or cargos) may include lipoparticles such as liposomes or micelles, albumin-based nanoparticles and polymeric nanoparticules including polymer-based polymersomes. Inorganic carriers may include quantum dots, carbon nanotubes, layered double hydroxides, mesoporous silica and magnetic nanoparticles (see notably Senapati, S., Mahanta, A. K., Kumar, S. et al. Controlled drug delivery vehicles for cancer treatment and their performance. Sig Transduct Target Ther 3, 7 (2018)).

Polymeric nanoparticles are solid, biocompatible, colloidal and often biodegradable systems with nanoscale dimensions. Polymeric nanoparticles can be made from synthetic polymers, e.g., poly(lactic acid) (PLA), poly($\varepsilon$-caprolactone) (PCL), poly(lactic-co-glycolic acid), N-(2-hydroxypropyl)-methacrylamide copolymer (HPMA) and poly(styrene-maleic anhydride) copolymer, or from natural polymers, such as gelatin, dextran, guar gum, chitosan, and collagen. Drugs can easily be encapsulated either through dispersion in the polymer matrix or conjugation/attachment to polymer molecules for their controlled delivery through surface or bulk erosion, diffusion through the polymer matrix, swelling followed by diffusion, or as a response to local stimuli.

Albumin is a protein that can be obtained from a variety of sources, including egg white (ovalbumin), bovine serum (bovine serum albumin, BSA), and human serum (human serum albumin, HSA), and is available in soybeans, milk, and grains. Albumin-based nanocarriers have several advantages, such as easy preparation, a high binding capacity for various drugs, nontoxic, non-immunogenic, biocompatible, and biodegradable properties, and along half-life in circulating plasma. The presence of functional groups (amino and carboxylic groups) on albumin nanoparticles surfaces makes it easy to bind targeting ligands and other surface modifications.

Micelles are spherical or globular colloidal nanoscale systems formed by self-assembly of amphiphilic block copolymers in an aqueous solution, resulting in a hydrophobic core and a hydrophilic shell. They belong to a group of amphiphilic colloids that can be formed spontaneously under certain concentrations (critical micelle concentration; CMC) and temperatures. The hydrophobic core serves as a reservoir for hydrophobic drugs, whereas the hydrophilic shell stabilizes the hydrophobic core and renders both polymer and hydrophobic drugs water soluble, making the particle an appropriate candidate for i.v. administration. The drugs are incorporated into a polymeric micelle through physical, chemical, or electrostatic interactions.

Liposomes are small, spherical, self-closed structures with at least one concentric lipid bilayer and an encapsulated aqueous phase in their core. They have been widely used as drug delivery vehicles since their discovery in 1965, due to their biocompatible and biodegradable nature and their unique ability to encapsulate hydrophilic agents (hydrophilic drugs, DNA, RNA, etc.) in their inner aqueous core and hydrophobic drugs within the lamellae, which makes them versatile therapeutic carriers. Furthermore, amphiphilic drugs can also be loaded into the liposome inner aqueous core using remote loading methods, such as the ammonium sulfate method for doxorubicin or the pH gradient method for vincristine (see Bolotin, E. M. et al. Ammonium sulfate gradients for efficient and stable remote loading of amphipathic weak bases into liposomes and ligandoliposomes. J. Liposome. Res. 4, 455-479 (1994), and Boman, N. L. et al., Liposomal vincristine which exhibits increased drug retention and increased circulation longevity cures mice bearing P388 tumors. Cancer Res. 54, 2830-2833 (1994)). Ligand-targeted liposomes have been found to promote the internalization of liposome-drug conjugates into specific target cells both in vitro and in vivo. Some liposomal formulations of chemotherapeutics have been translated into the clinic and demonstrated safety and improved pharmacokinetic properties of the drug. Prominent examples are liposomal doxorubicin (Doxil®), daunorubicin (DaunoXome®) and VCR (Marqibo®) which have contributed to reduced side-effects compared to the free drug (see O'Brien, M. E. R. et al., Ann. Oncol. 15, 440-449 (2004); Gill, P. S. et al., J. Clin. Oncol. 14, 2353-2364 (1996); and Shah, N. N. et al., Pediatr. Blood Cancer 63, 997-1005 (2016)).

For a recent review on liposome technologies for delivery of therapeutic compounds, see Bulbake, Upendra et al. "Liposomal Formulations in Clinical Use: An Updated Review." Pharmaceutics vol. 9, 2 12. 27 Mar. 2017. A typical example of targeted liposomes (i.e. bound to FGFR4 sdAbs as above described) is notably described in the result section (but see also Roveri, M. et al., Nanomedicine nnm-2017-0430 (2017). Exemplified liposome notably comprises a combination of egg sphingomyelin, cholesterol, PEG-ceramide (typically N-palmitoyl-sphingosine-1-[succinyl [methoxyPEG-2000]]), DSPE-PEG-maleimide (typically 1,2-distearoyl-sn-glycero-3-phosphoethanolamine-N-[maleimide (polyethylene glycol)-2000]) (both Avanti Polar Lipids) and DiR (1,1'-dioctadecyl-3,3,3',3'-tetramethylindotricarbocyanine Iodide) (Thermo Fisher Scientific). A favoured ratio of said lipids is typically of 49.8:45:4:1:0.2 mol %, respectively. A concentration around 70 mM of total lipids is achieved in the lipid film.

To produce actively targeted liposomes, DSPE-PEG lipids were introduced with reactive maleimide groups at the distal end. Single domain antibodies harboring a free cysteine at the C-terminus were then coupled to the liposomal surface. Typical therapeutic agents that can be encapsulated into liposomes include doxorubicin (Doxil®, Myocet®), daunorubicin (DaunoXome®), VCR (Marqibo®), Vinorelbine (TCL178).

The compounds as listed below can be directly conjugated to a single domain antibody as herein disclosed or encapsulated into a carrier as described above.

The term "toxin," "cytotoxin" or "cytotoxic compound" as used herein, refers to any agent that is detrimental to the growth and proliferation of cells and may act to reduce, inhibit, or destroy a cell or malignancy.

The term "anti-cancer compound" as used herein refers to any agent that can be used to treat a cell proliferative disorder such as cancer, including but not limited to, cytotoxic agents, chemotherapeutic agents, radioisotopes, targeted anti-cancer agents, immunotherapeutic agents (such as immunosuppressants or immune stimulators), and lytic peptides.

A therapeutic compound having anti-cancer or cytotoxic activity can be for example selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

Cytotoxic compound may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxyanthracindione; a tubulin-inhibitor such as maytansine or an analog or derivative thereof; an antimitotic agent such as mono methyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, Aleuritesfordii proteins, dianthin proteins, Phytolaccaamericana proteins such as PAPI, PAPII, and PAP-S, momordicacharantia inhibitor, curcin, crotin, sapaonariaofficinalis inhibitor, gelonin, mitogellin, restrictocin, phenomycin, and enomycin toxins; ribonuclease (R ase); DNase I, Staphylococcal enterotoxin A; pokeweed antiviral protein; diphtherin toxin; and *Pseudomonas* endotoxin.

In some embodiments, the therapeutic compound conjugated to a sdAb as herein disclosed or encapsulated into a nanocarrier functionalized with an sdAb as herein disclosed include an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and antifungal activity (Pettit et al, (1998) Antimicrob. Agents and Chemother. 42: 2961-2965). For example, auristatin E can be reacted with para-acetyl benzoic acid or benzoylvaleric acid to produce AEB and AEVB, respectively. Other typical auristatin derivatives include AFP, MMAF (monomethylauristatin F), and MMAE (monomethylauristatin E). Suitable auristatins and auristatinanalogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In some embodiments, the therapeutic compound conjugated to a sdAb as herein disclosed or encapsulated into a nanocarrier functionalized with an sdAb as herein disclosed include Mertansine (also called emtansine or DM1) or a peptide analog, derivative or prodrug thereof. Mertansine is a tubulin inhibitor, meaning that it inhibits the assembly of microtubules by binding to tubulin.

In some embodiments, the therapeutic compound conjugated to a sdAb as herein disclosed or encapsulated into a nanocarrier functionalized with an sdAb as herein disclosed include pyrrolo[2,1-c][1,4]-benzodiazepine (PDB) or an analog, derivative or prodrug thereof. Suitable PDBs and PDB derivatives, and related technologies are described in, e.g., Hartley J. A. et al, Cancer Res 2010; 70(17): 6849-6858; Antonow D. et al, Cancer J 2008; 14(3): 154-169; Howard P. W. et al, Bioorg Med ChemLett 2009; 19: 6463-6466 and Sagnou et al, Bioorg Med ChemLett 2000; 10(18): 2083-2086.

In some embodiments, the therapeutic compound conjugated to a sdAb as herein disclosed or encapsulated into a nanocarrier functionalized with an sdAb as herein disclosed include the group consisting of an anthracycline, maytansine, calicheamicin, duocarmycin, rachelmycin (CC-1065), dolastatin 10, dolastatin 15, irinotecan, monomethylauristatin E, monomethylauristatin F, a PDB, or an analog, derivative, or prodrug of any thereof.

In some embodiments, the therapeutic compound conjugated to a sdAb as herein disclosed or encapsulated into a nanocarrier functionalized with an sdAb as herein disclosed include an anthracycline or an analog, derivative or prodrug thereof. In some embodiments, the single domain antibody is conjugated to maytansine or an analog, derivative or prodrug thereof. In some embodiments, the single domain antibody is conjugated to calicheamicin or an analog, derivative or prodrug thereof. In some embodiments, the single domain antibody is conjugated to duocarmycin or an analog, derivative or prodrug thereof. In some embodiments, the single domain antibody is conjugated to rachelmycin (CC-1065) or an analog, derivative or prodrug thereof. In some embodiments, the antibody is conjugated to dolastatin 10 or an analog, derivative or prodrug thereof. In some embodiments, the antibody is conjugated to dolastatin 15 or an analog, derivative or prodrug thereof. In some embodiments, the antibody is conjugated to monomethylauristatin E or an analog, derivative or prodrug thereof. In some embodiments, the single domain antibody is conjugated to monomethylauristatin F or an analog, derivative or prodrug thereof. In some embodiments, the antibody is conjugated to pyrrolo [2,1-c][1,4]-benzodiazepine or an analog, derivative or prodrug thereof. In some embodiments, the single domain antibody is conjugated to irinotecan or an analog, derivative or prodrug thereof.

In some embodiments, the therapeutic compound conjugated to a sdAb as herein disclosed or encapsulated into a nanocarrier functionalized with an sdAb as herein disclosed include a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In some embodiments, the antibody is conjugated to an aptamer or a ribozyme.

In some embodiments, the therapeutic compound conjugated to a sdAb (e.g., as a fusion protein) as herein disclosed or encapsulated into a nanocarrier functionalized with an sdAb as herein disclosed include a lytic peptide such as CLIP, Magainin 2, mellitin, Cecropin and PI 8.

In some embodiments, the therapeutic compound conjugated to a sdAb (e.g., as a fusion protein) as herein disclosed or encapsulated into a nanocarrier functionalized with an sdAb as herein disclosed include a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFNa, IFN3, IFNy, GM-CSF, CD40L, Flt3 ligand, stem cell factor, ancestim, and TNFa.

In some embodiments, the therapeutic compound conjugated to a sdAb as herein disclosed or encapsulated into a nanocarrier functionalized with an sdAb as herein disclosed include a radioisotope or to a radioisotope-containing chelate. For example, the antibody can be conjugated to a chelator linker, e.g. DOTA, DTPA or tiuxetan, which allows for the antibody to be complexed with a radioisotope. The single domain antibody may also or alternatively comprise or be conjugated to one or more radiolabeled amino acids or other radiolabeled molecules Non-limiting examples of radioisotopes include $^3$H, $^{14}$C, $^{15}$N, $^{35}$S $^{90}$Y, "Tc, $^{125}$I, $^{131}$I, $^{186}$Re, $^{213}$Bi, $^{225}$Ac and $^{227}$Th. For therapeutic purposes, a radioisotope emitting beta- or alpha-particle radiation can be used, e.g., 1311, 90Y, 211At, 212Bi, 67Cu, 186Re, 188Re, and 212Pb.

A diagnostic compound can be selected from an enzyme, a fluorophore, a NMR or MRI contrast agent, a radioisotope or a nanoparticle. For example, the diagnostic compound can be selected from the group consisting of:

an enzyme such as horseradish peroxidase, alkaline phosphatase, glucose-6-phosphatase or beta-galactosidase;

a fluorophore such as green fluorescent protein (GFP), blue fluorescent dyes excited at wavelengths in the ultraviolet (UV) part of the spectrum (e.g. AMCA (7-amino-4-methylcournarin-3-acetic acid); Alexa Fluor® 350), green fluorescent dyes excited by blue light (e.g. FITC, Cy2, Alexa Fluor® 488), red fluorescent dyes excited by green light (e.g. rhodamines, Texas Red, Cy3, Alexa Fluor dyes 546, 564 and 594), or dyes excited with far-red light (e.g. Cy5) to be visualized with electronic detectors (CCD cameras, photomultipliers);

a radioisotope such as 18F, nC, 13N, 150, 68Ga, 82Rb, 44Sc, 64Cu, 86Y, 89Zr, 124I, 152Tb that can be used for PET imaging or 67Ga, 81mKr, 99mTc, mIn, 123I, 125I, 3Xe, 201Tl, 155Tb, 195mPt that can be used for SPECT/scintigraphic studies, or 14C, 3H, 35S, 3P, 125I that can be 211 212 75 76 131 1 1 1 used for autoradiography or in situ hybridisation, or At-, Bi-, Br-, Br-, I-, In, 177Lu—, 212Pb-, 186Re-, 188Re-, 153Sm-, 0Y that can be used to label the compounds;

a NMR or MRI contrast agent such as the paramagnetic agents gadolinium (Gd), dysprosium (Dy) and manganese (Mn), and the superparamagnetic agents based on iron oxide (such as MION, SPIO or USPIO) or iron platinium (SIPP), and X-nuclei such as 18F, 13C, 23Na, 170, 15N;

a nanoparticle such as gold nanoparticles (B. Van de Broek et al, ACSNano, Vol. 5, No. 6, 4319-4328, 2011) or quantum dots (A. Sukhanova et al, 2012 Nanomedicine, 8 516-525).

In a preferred embodiment, said diagnostic compound is a fluorophore, more preferably Alexa Fluor® 488, or a MRI contrast agent, more preferably gadolinium.

When the diagnostic agent is used for detection, it may comprise a radioactive atom for scintigraphic studies, for example 99Tc or 123I, or a spin label for nuclear magnetic resonance (NMR) imaging (also known as MRI), such as 13C, 9F, Fe, Gd, 123I, n lIn, Mn, 15N or 70.

The substance of interest according to the present disclosure may or may not permeate the mammal or human blood-brain barrier.

In some embodiments, when the compound of interest is a heterologous polypeptide, the single domain antibody of the present disclosure can be (alternatively, or in addition) fused to one or more heterologous polypeptide(s) to form a fusion protein (also named herein "fusion polypeptide" or "polypeptide"). A "fusion" or "chimeric" protein or polypeptide comprises a first amino acid sequence linked to a second amino acid sequence with which it is not naturally linked in nature. The amino acid sequences, which normally exist in separate proteins can be brought together in the fusion polypeptide. A fusion protein or polypeptide is created, for example, by chemical synthesis, or by creating and translating a polynucleotide in which the polypeptide regions are encoded in the desired relationship.

According to the present disclosure, the fusion protein can thus comprise at least one isolated humanized single domain antibody (hsbAb) according to the present disclosure that is fused either directly or via a spacer at its C-terminal end and/or at its N terminal end, notably fused at its C-terminal end to the N-terminal end of the heterologous polypeptide, and/or at its N-terminal end to the C-terminal end of the heterologous polypeptide. As used herein, the term "directly" means that the (first or last) amino acid at the terminal end (N or C-terminal end) of the humanized single domain antibody is fused to the (first or last) amino acid at the terminal end (N or C-terminal end) of the heterologous polypeptide. In other words, in this embodiment, the last amino acid of the C-terminal end of said sdAb is directly linked by a covalent bond to the first amino acid of the N-terminal end of said heterologous polypeptide, or the first amino acid of the N-terminal end of said sdAb is directly linked by a covalent bond to the last amino acid of the C-terminal end of said heterologous polypeptide. As used herein, the term "spacer" also called "linker" refers to a sequence of at least one amino acid that links the sdAb of the present disclosure to the heterologous polypeptide. Such a spacer may be useful to prevent steric hindrances. Examples of linkers disclosed in the present disclosure have the following sequences (Gly3-Ser)4, (Gly3-Ser), Ser-Gly or (Ala-Ala-Ala).

In some embodiments the compound of interest can be one or more polypeptides comprising another or the same antigen binding domain. Notably, the compound of interest can be one or more single domain antibodies as herein disclosed or not. The resulting fusion protein, or polypeptide, that comprises two or more antigen binding domains, notably that comprises or essentially consists of two or more single domain antibodies are referred to herein as "multivalent" polypeptides or antigen binding compounds. In some embodiments, said fusion protein or polypeptide can comprise at least one single domain antibody with a first binding domain, as herein described, and at least one other binding domain (e.g. directed against the same or another epitope, antigen, target, protein or polypeptide), which is typically also a single domain antibody. "Multispecific" (fusion) polypeptide refers to a polypeptide comprising at least two different antigen binding domains (i.e. that target different epitope, antigen or target), in opposition to a polypeptide comprising similar antigen binding domains, notably comprising the same single domain antibodies ("monospecific" (fusion) polypeptide).

Thus, in some embodiments, a fusion protein as herein described may also provide at least a second antigen binding domain directed against any desired protein, polypeptide, antigen, antigenic determinant or epitope. Said binding domain can be directed against FGFR4, notably against the same or different FGFR4 epitope, or may be directed against any other antigen, polypeptide or protein.

A "bispecific" fusion protein of the present disclosure is a fusion polypeptide that comprises at least one single domain antibody as herein disclosed directed against a first antigen (i.e. FGFR4) and at least one further binding domain directed against a second FGFR4 epitope or antigen (i.e. different from FGFR4), whereas a "trispecific" polypeptide of the present disclosure is a polypeptide that comprises at least one single domain antibody as herein disclosed and directed against a first antigen (i.e. FGFR4), at least one further binding domain directed against a second FGFR4 epitope or antigen (i.e. different from FGFR4) and at least one further binding domain directed against a third FGFR4 epitope or antigen (i.e. different from both i.e. first and second antigen); etc.

Examples antigens other than FGFR4 can be selected from PSMA, PSCA, BCMA, CS1, GPC3, CSPG4, EGFR, fetal acetylcholine receptor gamma subunit gamma (fAChRγ), HER3, IGF1R, SLC19A1, ACVR2A, EPHB4, CA125, IL-13R, CD278, CD123, NCAM, 5T4, CD2, CD3, CD16 (FcγRIII), CD23, MART-1, L1 CAM, MUC16, ROR1, SLAMF7, cKit, CD38, CD53, CD56, CD71, CD74, CD92, CD100, CD123, CD138, CD148, CD150, CD200, CD261, CD262, CD276, CD362, gp100, ROR1, mesothelin, CD33/IL3Ra, c-Met, Glycolipid F77, EGFRvIII, GD-2, NKp46 receptor, NY-ESO-1 TCR or MAGE A3 TCR, human telomerase reverse transcriptase (hTERT), survivin, cytochrome P450 1 Bi (CY1 B), HER2, Wilm's tumor gene 1 (WT1), livin, alphafetoprotein (AFP), carcinoembryonic antigen (CEA), mucin 16, MUC1, p53, cyclin, an immune checkpoint target or combinations thereof.

In some embodiment, the at least one further antigen of the multispecific fusion polypeptide comprises at least an immune cell antigen such as one or more T cell antigens, one or more macrophage antigens, one or more NK cell antigens, one or more neutrophil antigens, and/or one or more eosinophil antigens, as typically exemplifier for Bispecific T-cell or NK-cell engager molecules (see notably for BiTEs® Wolf E, Hofmeister R, Kufer P, Schlereth B, Baeuerle P A. "BiTEs: bispecific antibody constructs with unique anti-tumor activity". Drug Discov Today. 2005 Sep. 15; 10(18):1237-44. Review). Amongst others for T cell antigens, CD2 and framework sequences of T-cell receptor a and R chains can be used, notably CD2 or CD3 and most particularly the c chain of the CD3 complex. For example, for NK cell antigens fragments from the FcγRIII and/or from the NKp46 receptor can be used.

Said multispecific polypeptide can in used immune cell redirecting immune therapies on the same principle as for CAR therapies (see for illustrative review Ellwanger K, Reusch U, Fucek I, et al. Redirected optimized cell killing (ROCK®): A highly versatile multispecific fit-for-purpose antibody platform for engaging innate immunity. MAbs. 2019; 11(5):899-918).

In some embodiments, a further binding domain can be directed against a serum protein so that the half-life of the single domain antibody is increased. Typically, said serum protein is albumin.

In some embodiments, a further binding domain can be directed against a receptor on the vascular endothelium of the blood-brain barrier so that the single domain antibodies of the present disclosure would cross the blood-brain barrier. The targeted receptors include transferrin receptor, insulin receptor, IGF-I and IGF-II receptors, among others.

In some embodiments, the one or more further binding domain may comprise one or more parts, fragments or domains of conventional chain antibodies (and in particular human antibodies) and/or of heavy chain antibodies. For example, a single domain antibody as herein defined may be linked to a conventional (typically human) VH or VL optionally via a linker sequence.

In some embodiments, the polypeptides, or fusion proteins of the present disclosure can comprise a single domain antibody of the present disclosure that is linked to an immunoglobulin domain. For example, the polypeptides, or fusion proteins comprise a single domain antibody of the present disclosure that is linked to an Fc portion (such as a human Fc). Said Fc portion may be useful for increasing the half-life and even the production of the single domain antibody of the present disclosure. For example, the Fc portion can bind to serum proteins and thus increases the half-life on the single domain antibody. In some embodiments, at least one single domain antibody may also be linked to one or more (typically human) Hinge and/or CHI, and/or CH2 and/or CH3 domains, optionally via a linker sequence. For instance, a single domain antibody linked to a suitable CHI domain could for example be used—together with suitable light chains—to generate antibody fragments/ structures analogous to conventional Fab fragments or F(ab')2 fragments, but in which one or (in case of an F(ab')2 fragment) both of the conventional VH domains have been replaced by a single domain antibody as herein defined. In some embodiments, one or more single domain antibodies of the present disclosure may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the present disclosure and/or may confer the ability to bind to one or more Fc receptors. For example, for this purpose, and without being limited thereto, the one or more further amino acid sequences may comprise one or more CH2 and/or CH3 domains of an antibody, such as from a heavy chain antibody and more typically from a conventional human chain antibody; and/or may form and Fc region, for example from IgG (e.g. from IgG1, IgG2, IgG3 or IgG4), from IgE or from another human Ig such as IgA, IgD or IgM.

Chimeric Antigen Receptors

The terms "Chimeric antigen receptor" or "CAR" or "CARs" as used herein refer to engineered receptors, which graft an antigen specificity onto cells (for example T cells such as naive T cells, central memory T cells, effector memory T cells or combination thereof) thus combining the antigen binding properties of the antigen binding domain with the lytic capacity and self renewal of T cells. CARs are also known as artificial T cell receptors, chimeric T cell receptors or chimeric immunoreceptors. The term "antigen binding domain or "antigen-specific targeting domain" as used herein refers to the region of the CAR which targets and binds to specific antigens. When a CAR is expressed in a host cell, this domain forms the extracellular domain (ectodomain).

The CAR of the present disclosure comprises a molecule of the general formula:

$$\text{sdAb(n)-transmembrane domain-intracellular signaling domain,}$$

wherein n is 1 or more.

In some embodiments, n is at least 2, for example 2, 3, 4 or 5. The sdAb(n) form the antigen binding domain and is/are located at the extracellular side when expressed in a cell.

Typically, a CAR as herein described preferably comprises one or more, notably at least two antigen binding domains (each comprising a single domain antibody), which target one or more antigen. The antigen binding domain of a CAR of the present disclosure can comprise two or at least two sdAb that are both specific for the FGFR4, thus providing a bivalent binding molecule. In some embodiments, the antigen binding domain comprises two or at least two VH single domain antibodies that are both specific for FGFR4 but bind to different epitopes. In other words, the antigen binding domain comprises a first single domain antibody that binds to a first epitope of FGFR4 and a second single domain antibody that binds to a second epitope of FGFR4. The epitopes may be overlapping. Thus, the antigen binding domain is biparatopic. In other embodiments, the antigen binding domain comprises two single domain antibodies that are both specific for FGFR4 and bind to the same epitope.

In preferred embodiments, the antigen binding domain comprises one single domain antibody according to the present disclosure and that is thus specific for FGFR4 and another antigen binding domain that is specific for another antigen, thus providing a bispecific antigen binding domain. In other words, the antigen binding domain comprises a first single domain antibody that binds to a first target consisting in FGFR4 and a second single domain antibody that binds to a second target. Thus, in certain embodiments, the present disclosure relates to bispecific CARs.

As used herein, the term "bispecific CAR" or "bispecifc antigen binding domain" thus refers to a polypeptide that has specificity for two targets including FGFR4. Accordingly, a bispecific binding molecule as described herein can selectively and specifically bind to a cell that expresses (or displays on its cell surface) FGFR4 and the second target.

In other embodiments, the binding molecule comprises more than two antigen-binding domains providing a multispecific binding molecule. A multispecific antigen-binding domain as described herein can thus in addition to binding FGFR4 bind one or more additional targets, i.e., a multispecific polypeptide can bind at least two, at least three, at least four, at least five, at least six, or more targets, wherein the multispecific polypeptide agent has at least two, at least, at least three, at least four, at least five, at least six, or more target binding sites respectively.

In some embodiments, additional antigens that can be bound by a multispecific CAR according to the present disclosure include tumor antigens. In some embodiments, the tumor antigens are associated with a hematologic malignancy or with a solid tumor. For example, a tumor antigen can be selected from the group consisting of PSMA, PSCA, BCMA, CS1, GPC3, CSPG4, EGFR, fetal acetylcholine receptor gamma subunit gamma (fAChRγ), HER3, IGF1R, SLC19A1, ACVR2A, EPHB4, CA125, IL-13R, CD278, CD123, NCAM, 5T4, CD2, CD3, CD16 (FcγRIII), CD23, MART-1, L1 CAM, MUC16, ROR1, SLAMF7, cKit, CD38, CD53, CD56, CD71, CD74, CD92, CD100, CD123, CD138, CD148, CD150, CD200, CD261, CD262, CD276, CD362, gp100, ROR1, mesothelin, CD33/IL3Ra, c-Met, Glycolipid F77, EGFRvIII, GD-2, NKp46 receptor, NY-ESO-1 TCR or MAGE A3 TCR, human telomerase reverse transcriptase (hTERT), survivin, cytochrome P450 1 B1 (CY1 B), HER2, Wilm's tumor gene 1 (WT1), livin, alphafetoprotein (AFP), carcinoembryonic antigen (CEA), mucin 16, MUC1, p53, cyclin, an immune checkpoint target or combinations thereof. However, a skilled person would understand that other tumor antigens are also targets within the scope of the present disclosure.

In addition to a binding domain as described in detail above, a CAR of the present disclosure further comprises a transmembrane domain. A "transmembrane domain" (TMD) as used herein refers to the region of the CAR which crosses the plasma membrane and is connected to the endoplasmic signaling domain and the antigen binding domain, in case of the latter optionally via a hinge. In one embodiment, the transmembrane domain of the CAR of the present disclosure is the transmembrane region of a transmembrane protein (for example Type I transmembrane proteins), an artificial hydrophobic sequence or a combination thereof. In some embodiments, the transmembrane domain comprises the CD3zeta domain, CD28 transmembrane domain, the CD8 alpha transmembrane domain, the DAP10 transmembrane domain or the DAP 12 transmembrane domain. Other transmembrane domains will be apparent to those of skill in the art and may be used in connection with alternate embodiments of the present disclosure.

DAP10 and DAP12 are adapters that partner with most activating NKRs expressed in NK cells and all NKRs expressed in T cells (see Chen X, Bai F, Sokol L, et al. A critical role for DAP10 and DAP12 in CD8+ T cell-mediated tissue damage in large granular lymphocyte leukemia. Blood. 2009; 113(14):3226-3234).

In some embodiments the extracellular domain is fused to a hinge fused to the binding domain. A hinge may be any linker amino acid sequence comprising 2 to 50 amino acids, such as a CD8 hinge.

A CAR of the present disclosure further comprises an intracellular signaling domain. An "intracellular signaling domain", "cytoplasmic domain" or "endodomain" is the domain that transmits activation signals to T cells and directs the cell to perform its specialized function. Examples of domains that transduce the effector function signal and can be used according to the present disclosure include but are not limited to the ζ chain of the T-cell receptor complex or any of its homologs (e.g., η chain, FcsRIy and β chains, MB 1 (Iga) chain, B29 (Ig) chain, etc.), human CD3zeta chain, CD3 polypeptides (Δ, δ and ε), syk family tyrosine kinases (Syk, ZAP 70, etc.), src family tyrosine kinases (Lck, Fyn, Lyn, etc.) and intracellular domains from other molecules involved in T-cell transduction, such as CD2, CD5, OX40, CD28, DAP 10 and DAP12. Other intracellular signaling domains will be apparent to those of skill in the art and may be used in connection with alternate embodiments of the present disclosure. In some embodiments, the intracellular domain in notably selected from the intracellular domain of DAP10, DAP12, CD28, 4-1BB or the human CD3zeta chain.

Typically, a CAR according to the present disclosure can comprise the intracellular domains of the CD3 zeta chain and of 4-1BB.

In some embodiments, the CAR can comprise additional activation domain(s) (or intracellular domain) comprising a fragment of at least 50, 60, 70, 80, 90, 100, 1 10, 120, 150, or 200 amino acids of at least one additional activation domain selected from CD3-ζ chain (also shortly named ζ) and the cytoplasmic domain of a costimulatory receptors CD28, 4-1 BB (CD137), OX40 (CD134), LAG3, TRIM, HVEM, ICOS, CD27, or CD40L. In various embodiments, the CAR comprises additional activation domain(s) comprising a fragment of at least 20, 30, 40, 50, 60, 70, 80, 90, 100, 1 10, 120, 150, or 200 amino acids that shares at least than 90%, preferably more than 95%, more preferably more than 99% identity with the amino acid sequence of the additional activation domain above mentioned.

In some embodiments, a CAR of the present disclosure further comprises one or more co-stimulatory domains to enhance CAR-T cell activity after antigen specific engagement. Inclusion of this domain in the CAR of the present disclosure enhances the proliferation, survival and/or development of memory cells. The co-stimulatory domain is located intracellularˆ. The co-stimulatory domain is a functional signaling domain obtained from a protein selected form the following group: CD3zeta, CD28, CD137 (4-IBB), CD134 (OX40), DapIO, CD27, CD2, CD5, ICAM-1, LFA-1 (CD1 la/CD18), Lck, TNFR-I, TNFR-II, Fas, CD30, CD40, LAG3, TRIM, HVEM, ICOS, CD40L or combinations thereof. Other co-stimulatory domains (e.g., from other proteins) will be apparent to those of skill in the art. Multiple co-stimulatory domains can be included in a single CAR to recruit multiple signaling pathways. In one embodiment, the co-stimulatory domain is obtained from 4-1 BB. The term "4-1 BB" refers to a member of the TNFR superfamily with an amino acid sequence provided as GenBank Acc. No. AAA62478.2, or the equivalent residues from a non-human species, e.g., rodent (e.g. mouse or rat), monkey or ape. The term "4-1 BB costimulatory domain" refers to amino acid residues 214-255 of GenBank Acc. No. AAA62478.2, or the equivalent residues from a non-human species, e.g., mouse, rodent, monkey, ape and the like.

In some embodiments, a CAR of the present disclosure further comprises a hinge or spacer region which connects the extracellular antigen binding domain and the transmembrane domain. This hinge or spacer region can be used to achieve different lengths and flexibility of the resulting CAR. Examples of the a hinge or spacer region that can be used according to the present disclosure include, but are not limited to, Fc fragments of antibodies or fragments or derivatives thereof, hinge regions of antibodies, or fragments or derivatives thereof, CH2 regions of antibodies, CH3 regions of antibodies, artificial spacer sequences, for example peptide sequences, or combinations thereof. Other hinge or spacer region will be apparent to those of skill in the art and may be used in connection with alternate embodiments of the present disclosure. In one embodiment, the hinge is an IgG4 hinge or a CD8A hinge.

In some embodiments, a CAR of the present disclosure further comprises a "linker domain" or "linker region" that connects different domains of the CAR. This domain includes an oligo- or polypeptide region from about 1 to 100 amino acids in length. Suitable linkers will be apparent to those of skill in the art and may be used in connection with alternate embodiments of the present disclosure.

In some embodiments, a CAR of the present disclosure further comprises a "leader sequence". In one embodiment, the leader sequence is a CD8A domain.

A CAR of the present disclosure may further include a label or a tag. For example a label that facilitates imaging, such as a fluorescent label or other tag (such as myc). This can, for example be used in methods for imaging tumor binding. The label may be conjugated to the antigen binding domain.

The CARs described herein may be synthesized as single polypeptide chains. In this embodiment, the antigen-specific targeting regions are at the N-terminus, arranged in tandem and are separated by a linker peptide.

Example of CAR designs are notably provided in Jaspers J E, Brentjens R J. "Development of CAR T cells designed to improve antitumor efficacy and safety" (Pharmacol Ther. 2017; 178:83-91). Well-suited CAR designs according to the present disclosure notably include those described by Ying, Z. et al. (A safe and potent anti-CD19 CAR T cell therapy. Nat. Med. 25, 947-953 (2019)) and by June, C. H., O'Connor, R. S., Kawalekar, O. U., Ghassemi, S. & Milone, M. C. (CAR T cell immunotherapy for human cancer. Science (80-.). 359, 1361-1365 (2018)). Further suitable CAR constructs as per the present disclosure are notably disclosed in WO2019077165. Advantageously according to the present disclosure, the scFv binding domain(s) as described therein is/are replaced with one or more single domain antibody and comprise(s) at least one anti-FGFR4 single domain antibody as herein described.

The results included therein showed that FGFR4-CAR T cells composed of the myc-tagged A8 followed by the hinge and transmembrane domains of CD8 alpha and the intracellular signaling domains of 4-1BB and CD3 zeta mediate significant antitumor activity against FGFR4-expressing RMS cells in vitro and therefore represent a promising further targeted treatment option.

Nucleic Acids, Vectors, Host Cells

The present disclosure also provides isolated nucleic acids encoding a single domain antibody or a variant therefore or a CAR as previously described and nucleic acid constructs comprising thereof. A nucleic acid according to the present disclosure may be obtained by well-known methods of recombinant DNA technology and/or of chemical DNA synthesis. Also within the scope of the present disclosure, are sequences with at least 60%, 70%, 80% or 90% sequence identity thereto.

The term "nucleic acid," "polynucleotide," or "nucleic acid molecule" refers to deoxyribonucleic acid (DNA) or ribonucleic acid (RNA), or a combination of a DNA or RNA. RNA includes in vitro transcribed RNA or synthetic RNA; an mRNA sequence encoding a CAR polypeptide as described herein). The nucleic acid may further comprise a suicide gene. The construct may be in the form of a plasmid, vector, transcription or expression cassette.

The present disclosure thus also provides a recombinant expression cassette comprising a nucleic acid according to the present disclosure under the control of a transcriptional promoter allowing the regulation of the transcription of said nucleic acid in a host cell. Said nucleic acid can also be linked to appropriate control sequences allowing the regulation of its translation in a host cell.

The present disclosure also provides a recombinant vector (e.g., a recombinant expression vector) comprising a nucleic acid according to the present disclosure. Advantageously, said recombinant vector is a recombinant expression vector comprising an expression cassette according to the present disclosure.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

A vector according to the present disclosure is preferably a vector suitable for stable gene transfer and long-term gene expression into mammalian cells, such as by replication of the sequence of interest, expression of this sequence, maintaining of this sequence in extrachromosomal form, or else integration into the chromosomal material of the host. The recombinant vectors are constructed using standard recombinant DNA technology techniques and produced using conventional methods that are known in the art.

In some embodiments, a vector of the present disclosure is an integrating vector, such as an integrating viral vector, such as in particular a retrovirus or AAV vector. Preferably, the viral vector is a lentiviral vector, most preferably an integrating viral vector.

Within the context of the present disclosure, a "lentiviral vector" means a non-replicating non-pathogenic virus engineered for the delivery of genetic material into cells, and requiring lentiviral proteins (e.g., Gag, Pol, and/or Env) that are provided in trans. Indeed, the lentiviral vector lacks expression of functional Gag, Pol, and Env proteins. The lentivirus vector is advantageously a self-inactivating vector (SIN vector). The lentiviral vector comprises advantageously a central polypurine tract/DNA FLAP sequence (cPPT-FLAP), and/or insulator sequence (s) such as chicken beta-globin insulator sequence(s) to improve expression of the gene(s) of interest. The lentiviral vector is advantageously pseudotyped with another envelope protein, preferably another viral envelope protein, preferably the vesicular *stomatis* virus (VSV) glycoprotein. In some preferred embodiments, said lentiviral vector is a human immunodeficiency virus (HIV) vector.

Lentiviral vectors derive from lentiviruses, in particular human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV), which are modified to remove genetic determinants involved in pathogenicity and introduce new determinants useful for obtaining therapeutic effects.

The lentiviral vector may be present in the form of an RNA or DNA molecule, depending on the stage of production or development of said retroviral vectors. The lentiviral vector can be in the form of a recombinant DNA molecule, such as a plasmid, or in the form of a lentiviral vector particle (interchangeably named lentiviral particle in the context of the present disclosure), such as an RNA molecule(s) within a complex of lentiviral and other proteins.

Such vectors are based on the separation of the cis- and trans-acting sequences. In order to generate replication-defective vectors, the trans-acting sequences (e.g., gag, pol, tat, rev, and env genes) can be deleted and replaced by an expression cassette encoding a transgene.

Efficient integration and replication in non-dividing cells generally requires the presence of two c/s-acting sequences at the center of the lentiviral genome, the central polypurine tract (cPPT) and the central termination sequence (CTS). These lead to the formation of a triple-stranded DNA structure called the central DNA "flap", which acts as a signal for uncoating of the pre-integration complex at the nuclear pore and efficient importation of the expression cassette into the nucleus of non-dividing cells, such as dendritic cells. In one embodiment, the present disclosure encompasses a lentiviral vector comprising a central poly-purine tract and central termination sequence referred to as cPPT/CTS sequence as described, in particular, in the European patent application EP 2 169 073.

Further sequences are usually present in cis, such as the long terminal repeats (LTRs) that are involved in integration of the vector proviral DNA sequence into a host cell genome. Vectors may be obtained by mutating the LTR sequences, for instance, in domain U3 of said LTR (AU3) (Miyoshi H et al, 1998, J Virol. 72(10):8150-7; Zufferey et al., 1998, J V/ro/72(12):9873-80). Preferably, the vector does not contain an enhancer. In one embodiment, the present disclosure encompasses a lentiviral vector comprising LTR sequences, preferably with a mutated U3 region (AU3) removing promoter and enhancer sequences in the 3' LTR.

The packaging sequence Ψ (psi) can also be incorporated to help the encapsidation of the polynucleotide sequence into the vector particles (Kessler et al., 2007, Leukemia, 21 (9): 1859-74; Paschen et al., 2004, Cancer Immunol Immunother 12(6): 196-203). In one embodiment, the present disclosure encompasses a lentiviral vector comprising a lentiviral packaging sequence Ψ (psi).

Further additional functional sequences, such as a trans-port RNA-binding site or primer binding site (PBS) or a Woodchuck PostTranscriptional Regulatory Element (WPRE), can also be advantageously included in the lenti-viral vector polynucleotide sequence of the present disclo-sure, to obtain a more stable expression of the transgene in vivo. can also be advantageously included in the lentiviral vector polynucleotide sequence of the present disclosure, to obtain a more stable expression of the transgene in vivo. In some embodiments, the present disclosure encompasses a lentiviral vector comprising a PBS. In some embodiments, the present disclosure encompasses a lentiviral vector com-prising a WPRE and/or an IRES.

Thus, in a preferred embodiment, the lentiviral vector comprises at least one cPPT/CTS sequence, one Ψ sequence, one (preferably 2) LTR sequence, and an expression cassette including a transgene under the transcriptional control of a β2ηη or class I MHC promoter.

In some embodiments of the present disclosure, a vector (i.e. a recombinant transfer vector) of the present disclosure is an expression vector comprising appropriate means for expression of the target fusion protein in a host cell.

Various promoters may be used to drive high expression of the nucleic acid sequence encoding the target fusion protein. The promoter may be a tissue-specific, ubiquitous, constitutive or inducible promoter. Preferred promoters are notably functional in T cells and/or NK cells, preferably human T cells and human NK cells. In particular, preferred promoters are able to drive high expression of the target fusion protein (notably a CAR as previously defined) from lentivectors in T cells or NK cells, preferably human T cells or NK T cells. For example, a promoter according to the present disclosure can be selected from phosphoglycerate kinase promoter (PGK), spleen focus-forming virus (SFFV) promoters, elongation factor-1 alpha (EF-1 alpha) promoter including the short form of said promoter (EFS), viral promoters such as cytomegalovirus (CMV) immediate early enhancer and promoter, retroviral 5' and 3' LTR promoters including hybrid LTR promoters, human ubiquitin promoter, MHC class I promoter, MHC class II promoter, and β2 microglobulin (β2ηη) promoter. The promoters are advan-tageously human promoters, i.e., promoters from human cells or human viruses such as spleen focus-forming virus (SFFV). Human ubiquitin promoter, MHC class I promoter, MHC class II promoter, and β2 microglobulin (β2ηη) promoter are more particular preferred. Preferably, the MHC class I promoter is an HLA-A2 promoter, an HLA-B7 promoter, an HLA-Cw5 promoter, an HLA-F, or an HLA-E promoter. In some embodiments the promoter is not a CMV promoter/enhancer, or is not a dectin-2 or MHCII promoter. Such promoters are well-known in the art and their sequences are available in sequence data base.

Typically, lentiviral particles refer to the extracellular infectious form of a virus composed of genetic material made from either DNA or RNA (most preferably single stranded RNA) surrounded by a protein coat, called the capsid, and in some cases an envelope of lipids that sur-rounds the capsid. Thus a lentiviral vector particle (or a lentiviral particle) comprises a lentiviral vector as previously defined in association with viral proteins. The vector is preferably an integrating vector.

The RNA sequences of the lentiviral particle can be obtained by transcription from a double-stranded DNA sequence inserted into a host cell genome (proviral vector DNA) or can be obtained from the transient expression of plasmid DNA (plasmid vector DNA) in a transformed host cell. Appropriate methods for designing and preparing len-tiviral particles in particular for therapeutic application are well-known in the art and are for example described in Merten O W, Hebben M, Bovolenta C. Production of len-tiviral vectors. Mol Ther Methods Clin Dev. 2016 Apr. 13; 3:16017.

Preferably the lentiviral particles have the capacity for integration. As such, they contain a functional integrase protein. Non-integrating vector particles have one or more mutations that eliminate most or all of the integrating capacity of the lentiviral vector particles. For, example, a non-integrating vector particle can contain mutation(s) in the integrase encoded by the lentiviral pol gene that cause a reduction in integrating capacity. In contrast, an integrating vector particle comprises a functional integrase protein that does not contain any mutations that eliminate most, or all of the integrating capacity of the lentiviral vector particles.

In some embodiments, the present disclosure encom-passes a vector system comprising one or more vector comprising:

(a) a nucleic acid comprising a nucleic acid sequence encoding a chimeric antigen receptor as previously defined, wherein the nucleic acids (a) and (b) are located on the same or on separated vectors.

Preferred nucleic acids (a) have been described in the prior section.

When the vector system comprises more than one vector, typically two or more vectors, said vectors are typically of the same type (e.g.: a lentiviral vector). In the following sections the vector can also be intended as "the one or more vector" or "the vector system". Preferably the present disclosure encompasses a lentiviral vector system and notably a lentiviral particle system.

According to the present disclosure, the vector can be an expression vector. The vector can be a plasmid vector.

Thus in one embodiment, the present disclosure encompasses a vector notably and expression vector, most preferably a lentiviral vector, comprising a nucleic acid encoding the CAR protein as previously defined.

The present disclosure also encompasses a viral particle system, wherein the one or more viral particle comprises a viral vector, typically an integrating viral vector, as previously defined. Preferably, the viral vector is a lentiviral vector and the viral particle is a lentiviral particle.

The present disclosure also provides a host cell containing a nucleic acid construct as herein disclosed, notably a recombinant expression cassette or a recombinant vector according to the present disclosure. The host cell is either a prokaryotic or eukaryotic host cell. The terms "host cell" refers to a cell into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell but may contain mutations. Mutant progeny that have the same function or biological activity as screened or selected for in the originally transformed cell are included herein.

The present disclosure also provides a method for producing in a host cell as defined above a polypeptide, consisting or comprising a single domain antibody or a CAR as previously defined, comprising the steps of providing a host cell containing a nucleic acid construct, a recombinant expression cassette or a recombinant vector according to the present disclosure,
 culturing said host cell,
 and optionally purifying the single domain antibody or CAR of the present disclosure.

Methods for purifying polypeptides are well known in the art, such as chromatography (e.g., ion exchange chromatography, gel permeation chromatography and reversed phase chromatography).

The present disclosure also encompasses compositions comprising a nucleic acid construct as herein disclosed.

Immune Cells and Method for Obtaining Thereof

The present disclosure also provides isolated cells, populations of cells, cell lines, or cell cultures, comprising a nucleic acid construct as previously described, notably vectors and more particularly a viral vector particle encoding at least one or more CAR as previously described.

In one embodiment, the cell contains the vector and/or viral vector particle integrated into the cellular genome. In one embodiment, the cell contains the vector stably expressing the CAR. In one embodiment, the cell produces lentiviral vector particles encoding the CARs.

The cells are preferably mammalian cells, particularly human cells. Particularly preferred are human non-dividing cells. Preferably, the cells are immune cells, As used herein, the term "immune cells" includes cells that are of hematopoietic origin and that play a role in the immune response. Immune cells include lymphocytes, such as B cells and T cells, natural killer cells (NK cells), myeloid cells, such as monocytes, macrophages, eosinophils, mast cells, basophils, and granulocytes.

As used herein, the term "T cell" includes cells bearing a T cell receptor (TCR), T-cells according to the present disclosure can be selected from the group consisting of inflammatory T-lymphocytes, cytotoxic T-lymphocytes, regulatory T-lymphocytes, Mucosal-Associated Invariant T cells (MAIT), Yδ T cell, tumour infiltrating lymphocyte (TILs) or helper T-lymphocytes included both type 1 and 2 helper T cells and Th17 helper cells. In another embodiment, said cell can be derived from the group consisting of CD4+ T-lymphocytes and CD8+ T-lymphocytes.

Said immune cells may originate from a healthy donor or from a subject suffering from a cancer.

Immune cells can be extracted from blood or derived from stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells.

T-cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments, T-cells can be obtained from a unit of blood collected from a subject using any number of techniques known to the skilled person, such as FICOLL™ separation. In one embodiment, cells from the circulating blood of a subject are obtained by apheresis. In certain embodiments, T-cells are isolated from PBMCs. PBMCs may be isolated from buffy coats obtained by density gradient centrifugation of whole blood, for instance centrifugation through a LYMPHOPREP™ gradient, a PERCOLL™ gradient or a FICOLL™ gradient. T-cells may be isolated from PBMCs by depletion of the monocytes, for instance by using CD14 DYNABEADS®. In some embodiments, red blood cells may be lysed prior to the density gradient centrifugation.

In another embodiment, said cell can be derived from a healthy donor, from a subject diagnosed with cancer, notably with Ewing sarcoma. The cell can be autologous or allogeneic.

In allogeneic immune cell therapy, immune cells are collected from healthy donors, rather than the patient. Typically, these are HLA matched to reduce the likelihood of graft vs. host disease. Alternatively, universal 'off the shelf' products that may not require HLA matching comprise modifications designed to reduce graft vs. host disease, such as disruption or removal of the TCRαβ receptor. See Graham et al., Cells. 2018 October; 7(10): 155 for a review. Because a single gene encodes the alpha chain (TRAC) rather than the two genes encoding the beta chain, the TRAC locus is a typical target for removing or disrupting TCRαβ receptor expression. Alternatively, inhibitors of TCRαβ signalling may be expressed, e.g. truncated forms of CD3 (can act as a TCR inhibitory molecule. Disruption or removal of HLA class I molecules has also been employed. For example, Torikai et al., Blood. 2013; 122:1341-1349 used ZFNs to knock out the HLA-A locus, while Ren et al., Clin. Cancer Res. 2017; 23:2255-2266 knocked out Beta-2 microglobulin (B2M), which is required for HLA class I expression. Ren et al. simultaneously knocked out TCRαβ, B2M and the immune-checkpoint PD1. Generally, the immune cells are activated and expanded to be utilized in the adoptive cell therapy. The immune cells as herein disclosed can be expanded in vivo or ex vivo. The immune cells, in particular T-cells can be activated and expanded generally using methods known in the art. Generally the T-cells are expanded by contact with a surface having attached thereto an agent that stimulates a CD3/TCR complex associated signal and a ligand that stimulates a co-stimulatory molecule on the surface of the T cells.

Typically, the immune cell is modified to express chimeric antigen receptor as herein disclosed. Expression of multiple tumor-specific targets may reduce the chance of antigen escape by mutating or reducing expression of the target antigen. As previously described the CARs of the present disclosure may be multispecific CARs (i.e. directed against more than one antigen, that is directed against FGFR4 and at least another antigen). In addition, or alternatively, an immune cell as herein described may express one or more CAR(s) as herein defined and at least another CAR targeting one or more nother antigen(s).

Methods by which immune cells can be genetically modified to express a recombinant antigen receptor are well known in the art. A nucleic acid molecule encoding the antigen receptor may be introduced into the cell in the form of e.g. a vector, or any other suitable nucleic acid construct. Vectors, and their required components, are well known in the art. Nucleic acid molecules encoding antigen receptors can be generated using any method known in the art, e.g. molecular cloning using PCR. Antigen receptor sequences can be modified using commonly-used methods, such as site-directed mutagenesis.

In another aspect, the present disclosure relates to an ex vivo method for generating a population of cells for use in adaptive immunotherapy comprising transforming said cell with a CAR as herein described.

Compositions and Kits of the Present Disclosure

The present disclosure also encompasses pharmaceutical compositions comprising one or more anti-FGFR4 single domain antibody(ies), CAR(s), nucleic acid construct encoding thereof and/or one or more isolated cell(s) or cell population(s) comprising a CAR as herein disclosed, alone or in combination with at least one other agent, such as a stabilizing compound, which may be administered in any sterile, biocompatible pharmaceutical carrier and optionally formulated with formulated with sterile pharmaceutically acceptable buffer(s), diluent(s), and/or excipient(s). Pharmaceutically acceptable carriers typically enhance or stabilize the composition, and/or can be used to facilitate preparation of the composition. Pharmaceutically acceptable carriers include solvents, dispersion media, coatings, antibacterial and antifungal agents, isotonic and absorption delaying agents, and the like that are physiologically compatible, and in some embodiments, pharmaceutically inert. In some embodiment, a pharmaceutical composition according to the present disclosure comprises an anti-FGFR4 single domain antibody as herein disclosure linked to drug nanocarrier as previously disclosed. Typically said drug nanocarriers, dunctionalized with an anti-FGFR4 sdAb as herein disclosed are encapsulated a therapeutic (such as a cytotoxic) or a diagnostic compound. In particular embodiments, said drug nanocarriers are liposomes.

Administration of a pharmaceutical composition comprising sdAbs as herein disclosed can be accomplished orally or parenterally. Methods of parenteral delivery include topical, intra-arterial (directly to the tumor), intramuscular, spinal, subcutaneous, intramedullary, intrathecal, intraventricular, intravenous, intraperitoneal, or intranasal administration.

The genetically modified cells or pharmaceutical composition of the present disclosure can be administered by any convenient route, including parenteral administration. Parenteral administration includes, for example, intravenous, intramuscular, intraarterial, intraperitoneal, intranasal, rectal, intravesical, intradermal, topical or subcutaneous administration. Compositions can take the form of one or more dosage units.

Thus, in addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Ed. Maack Publishing Co, Easton, Pa.).

Depending on the route of administration, the single domain antibody or variant thereof, may be coated in a material to protect the compound from the action of acids and other natural conditions that may inactivate the compound.

The composition is typically sterile and preferably fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxilliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl, cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, ie. dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the present disclosure may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Pharmaceutical compositions of the disclosure can be prepared in accordance with methods well known and routinely practiced in the art. See. e.g., Remington: The Science and Practice of Pharmacy, Mack Publishing Co., 20th ed., 2000; and Sustained and Controlled Release Drug Delivery Systems, J R. Robinson, ed., Marcel Dekker, Inc., New York, 1978. Pharmaceutical compositions are preferably manufactured under GMP conditions.

The amount of the pharmaceutical composition of the present disclosure that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions as herein disclosed comprise an effective amount of a binding molecule of the present disclosure (e.g. a single domain antibody or variant thereof or a chimeric antigen receptor) such that a suitable dosage will be obtained. The correct dosage of the compounds will vary according to the particular formulation, the mode of application, and its particular site, host and the disease being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Typically, this amount is at least about 0.01% of a binding molecule of the present disclosure by weight of the composition. Preferred compositions of the present disclosure are prepared so that a parenteral dosage unit contains from about 0.01% to about 2% by weight of the binding molecule of the present disclosure.

For intravenous administration, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight.

The present compositions can take the form of suitable carriers, such aerosols, sprays, suspensions, or any other form suitable for use. Other examples of suitable pharmaceutical carriers are described in "Remington's Pharmaceutical Sciences" by E. W. Martin.

The pharmaceutical compositions as herein disclosed can be co-administered with other therapeutics, for example anti-cancer agents.

Medical Uses

The present disclosure also relates to an anti-FGFR4 single domain antibody or variant thereof as herein described, a CAR directed against FGFR4 or variant thereof as herein described, a nucleic acid encoding said anti-FGFR4 single domain antibody or CAR, or to a cell, line or cell population comprising a CAR as described herein for use in therapy, in particular, for use in the treatment of cancer. The present disclosure also relates to an anti-FGFR4 single domain antibody or variant thereof as herein described, a CAR directed against FGFR4 or variant thereof as herein described, a nucleic acid encoding said anti-FGFR4 single domain antibody or CAR, or to a cell, line or cell population comprising said CAR as described herein in the manufacture of a medicament, notably for the treatment of cancer.

The present disclosure also encompasses methods for the prevention and/or treatment of cancer, comprising administering to a subject to an anti-FGFR4 single domain antibody or variant thereof as herein described, a CAR directed against FGFR4 or variant thereof as herein described, a nucleic acid encoding said anti-FGFR4 single domain antibody or CAR, or a cell, line or to a cell population comprising a CAR as described herein, said method comprising administering, to a subject in need thereof, a pharmaceutically active amount of an anti-FGFR4 single domain antibody or variant thereof, a CAR, a cell, line or cell population comprising a CAR as described herein and/or of a pharmaceutical composition of the present disclosure. The method may additionally comprise the step of identifying a subject who has cancer.

The present disclosure also include the use of one or more of to the anti-FGFR4 single domain antibodies or variants thereof, CARs directed against FGFR4 or variants thereof, nucleic acids encoding said anti-FGFR4 single domain antibodies or CARs, cell lines or cell population comprising a CAR as described herein in targeted immune therapy. For example sdAbs of the present disclosure and in particular variants thereof in the form of multispecific polypeptides further targeting an immune cell antigen, and CAR expressing immune cells (notably CAR T cells) may be used in immune cell redirecting immune therapies.

In another aspect, the present disclosure relates to a method for stimulating a T cell-mediated immune response to a target cell population or tissue in a subject, the method comprising administering to a subject an effective amount of a cell or cell population that expresses a CAR directed against FGFR4 as herein described.

In another aspect, the present disclosure relates to a method of providing an anti-tumor immunity in a subject, the method comprising administering to the mammal an effective amount of a cell or cell population genetically modified to express a CAR directed against FGFR4 as herein described, thereby providing an anti-tumor immunity in the subject.

The present disclosure also relates to an anti-FGFR4 single domain antibody (including variants thereof), a CAR directed against FGFR4 as herein described, or a nucleic acid construct encoding said humanized anti-FGFR4 SdAb or CAR, or to an immune cell expressing said CAR, as previously defined, for use in adoptive cell or CAR-T cell therapy in a subject. Typically, the immune cell for use in the method of the present disclosure is a redirected T-cell, e.g. a redirected CD8+ and/or CD4+ T-cell.

In some embodiments, anti-FGFR4 single domain antibodies (including variants thereof), and CARs directed against FGFR4 as herein described, as well as nucleic acid constructs encoding them and cells comprising such CARs are useful for inhibiting tumor growth, inducing differentiation, reducing tumor volume, and/or reducing the tumorigenicity of a tumor. The methods of use can be in vitro, ex vivo, or in vivo methods.

In specific embodiments of the medical uses as described herein, the anti-FGFR4 sdAb is linked as previously described to a drug nanocarrier, such as a liposome. Said drug nanocarrier, notably such liposome, functionalized with one or more anti-FGFR4 sdAbs as herein described typically encapsulates a therapeutic compound (such as a cytotoxic compound) or a diagnostic compound.

In certain aspects, the subject is a human, notably a pediatric patient. In certain aspects, the subject has a tumor or has had a tumor removed. The subject can also be at risk of developing a cancer.

The cancer can be a solid cancer or a liquid tumor. Cancers that may treated by methods, uses and compositions described herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma (RMS); embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

More specific cancers which can be treated and/or prevented according to the present disclosure include FGFR4-mediated cancers. Typically, FGFR4-mediated cancers are cancers wherein FGFR4 is expressed or overexpressed. Typical cancers wherein FGFR4 is expressed and/or overexpressed include hepatocellular carcinoma (HCC), breast cancer, oropharyngeal squamous cell carcinoma, oral squamous cell carcinoma, pancreatic carcinomas and derived cell lines and rhabdomyosarcoma (RMS).

In some embodiments, cancer treatment, and/or adoptive cell cancer therapy as above described are administered in combination with additional cancer therapies. In some embodiments, cancer treatment and/or adoptive cell cancer therapy as above described are administered in combination with targeted therapy, immunotherapy such as immune checkpoint therapy and immune checkpoint inhibitor, co-stimulatory antibodies, chemotherapy and/or radiotherapy.

Immune checkpoint therapy such as checkpoint inhibitors include, but are not limited to programmed death-1 (PD-1) inhibitors, programmed death ligand-1 (PD-L1) inhibitors, programmed death ligand-2 (PD-L2) inhibitors, lymphocyte-activation gene 3 (LAG3) inhibitors, T-cell immunoglobulin and mucin-domain containing protein 3 (TIM-3) inhibitors, T cell immunoreceptor with Ig and ITIM domains (TIGIT) inhibitors, B- and T-lymphocyte attenuator (BTLA) inhibitors, V-domain Ig suppressor of T-cell activation (VISTA) inhibitors, cytotoxic T-lymphocyte-associated protein 4 (CTLA4) inhibitors, Indoleamine 2,3-dioxygenase (IDO) inhibitors, killer immunoglobulin-like receptors (KIR) inhibitors, KIR2L3 inhibitors, KIR3DL2 inhibitors and carcinoembryonic antigen-related cell adhesion molecule 1 (CEACAM-1) inhibitors. In particular, checkpoint inhibitors include antibodies anti-PD1, anti-PD-L1, anti-CTLA-4, anti-TIM-3, anti-LAG3. Co-stimulatory antibodies deliver positive signals through immune-regulatory receptors including but not limited to ICOS, CD137, CD27, OX-40 and GITR.

Example of anti-PD1 antibodies include, but are not limited to, nivolumab, cemiplimab (REGN2810 or REGN-2810), tislelizumab (BGB-A317), tislelizumab, spartalizumab (PDR001 or PDR-001), ABBV-181, JNJ-63723283, BI 754091, MAG012, TSR-042, AGEN2034, pidilizumab, nivolumab (ONO-4538, BMS-936558, MDX1106, GTPL7335 or Opdivo), pembrolizumab (MK-3475, MK03475, lambrolizumab, SCH-900475 or Keytruda) and antibodies described in International patent applications WO2004004771, WO2004056875, WO2006121168, WO2008156712, WO2009014708, WO2009114335, WO2013043569 and WO2014047350.

Example of anti-PD-L1 antibodies include, but are not limited to, LY3300054, atezolizumab, durvalumab and avelumab.

Example of anti-CTLA-4 antibodies include, but are not limited to, ipilimumab (see, e.g., U.S. Pat. Nos. 6,984,720 and 8,017,114), tremelimumab (see, e.g., U.S. Pat. Nos. 7,109,003 and 8,143,379), single chain anti-CTLA4 antibodies (see, e.g., International patent applications WO1997020574 and WO2007123737) and antibodies described in U.S. Pat. No. 8,491,895.

Example of anti-VISTA antibodies are described in US patent application US20130177557.

Example of inhibitors of the LAG3 receptor are described in U.S. Pat. No. 5,773,578.

Example of KIR inhibitor is IPH4102 targeting KIR3DL2.

As used herein, the term "chemotherapy" has its general meaning in the art and refers to the treatment that consists in administering to the patient a chemotherapeutic agent. A chemotherapeutic entity as used herein refers to an entity which is destructive to a cell, that is the entity reduces the viability of the cell. The chemotherapeutic entity may be a cytotoxic drug. Chemotherapeutic agents include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBT-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; methylhydrazine derivatives including N-methylhydrazine (MIH) and procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-1 1); topoisomerase inhibitor RFS 2000; difluoromethylomithine (DMFO); retinoids such as retinoic acid; capecitabine; anthracyclines, nitrosoureas, antimetabolites, epipodophylotoxins, enzymes such as L-asparaginase; anthracenediones; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide; biological response modifiers such as IFNa, IL-2, G-CSF and GM-CSF; and pharmaceutically acceptable salts, acids or derivatives of any of the above.

Suitable examples of radiation therapies include, but are not limited to external beam radiotherapy (such as superficial X-rays therapy, orthovoltage X-rays therapy, megavoltage X-rays therapy, radiosurgery, stereotactic radiation therapy, Fractionated stereotactic radiation therapy, cobalt therapy, electron therapy, fast neutron therapy, neutron-capture therapy, proton therapy, intensity modulated radiation therapy (IMRT), 3-dimensional conformal radiation therapy (3D-CRT) and the like); brachytherapy; unsealed source radiotherapy; tomotherapy; and the like. Gamma rays are another form of photons used in radiotherapy. Gamma rays are produced spontaneously as certain elements (such as radium, uranium, and cobalt 60) release radiation as they decompose, or decay. In some embodiments, radiotherapy may be proton radiotherapy or proton minibeam radiation therapy. Proton radiotherapy is an ultra-precise form of radiotherapy that uses proton beams (Prezado Y, Jouvion G, Guardiola C, Gonzalez W, Juchaux M, Bergs J, Nauraye C, Labiod D, De Marzi L, Pouzoulet F, Patriarca A, Dendale R. Tumor Control in RG2 Glioma-Bearing Rats: A Comparison Between Proton Minibeam Therapy and Standard Proton Therapy. Int J Radiat Oncol Biol Phys. 2019 Jun. 1; 104(2): 266-271. doi: 10.1016/j.ijrobp.2019.01.080; Prezado Y, Jouvion G, Patriarca A, Nauraye C, Guardiola C, Juchaux M, Lamirault C, Labiod D, Jourdain L, Sebrie C, Dendale R, Gonzalez W, Pouzoulet F. Proton minibeam radiation therapy widens the therapeutic index for high-grade gliomas. Sci Rep. 2018 Nov. 7; 8(1):16479. doi: 10.1038/s41598-018-34796-8). Radiotherapy may also be FLASH radiotherapy (FLASH-RT) or FLASH proton irradiation. FLASH radiotherapy involves the ultra-fast delivery of radiation treatment at dose rates several orders of magnitude greater than those currently in routine clinical practice (ultra-high dose rate) (Favaudon V, Fouillade C, Vozenin M C. The radiotherapy FLASH to save healthy tissues. Med Sci (Paris) 2015; 31: 121-123. DOI: 10.1051/medsci/20153102002); Patriarca A., Fouillade C. M., Martin F., Pouzoulet F., Nauraye C., et al. Experimental set-up for FLASH proton irradiation of small animals using a clinical system. Int J Radiat Oncol Biol Phys, 102 (2018), pp. 619-626. doi: 10.1016/j.ijrobp.2018.06.403. Epub 2018 Jul. 11).

"In combination" may refer to administration of the additional therapy before, at the same time as or after administration of the T cell composition according to the present disclosure.

In addition, or as an alternative to the combination with checkpoint blockade, the T cell composition of the present disclosure may also be genetically modified to render them resistant to immune-checkpoints using gene-editing technologies including but not limited to TALEN and Crispr/Cas. Such methods are known in the art, see e.g. US20140120622. Gene editing technologies may be used to prevent the expression of immune checkpoints expressed by T cells (see the above listed checkpoint inhibitors) and more particularly but not limited to PD-1, Lag-3, Tim-3, TIGIT, BTLA CTLA-4 and combinations of these. The T cell as discussed here may be modified by any of these methods.

The T cell according to the present disclosure may also be genetically modified to express molecules increasing homing into tumors and or to deliver inflammatory mediators into the tumor microenvironment, including but not limited to cytokines, soluble immune-regulatory receptors and/or ligands.

Having thus described different embodiments of the present disclosure, it should be noted by those skilled in the art that the disclosures herein are exemplary only and that various other alternatives, adaptations, and modifications may be made within the scope of the present disclosure. Accordingly, the present disclosure is not limited to the specific embodiments as illustrated herein.

Molecular Imaging and Diagnostic Tool

The nanobodies as herein disclosed are of high interest in molecular imaging and diagnostic (both in vitro and in vivo), typically to target imaging agents such as radionuclides to the cell of interest in vivo. Thus nanobody-targeted imaging can be used according to the present invention for a variety of purposes including the diagnostic of diseases, the monitoring of disease progression and the prediction of response to a specific therapeutic agent in particular to an anti-FGFR4 agent such as an anti-FGFR4 sdAb as herein disclosed.

Nanobodies can aid in early diagnosis and cancer prevention by detecting or defining biomarkers. Nanobodies can improve current mAb-based diagnostic techniques due to their high specificity. Furthermore, their high stability under extremes of temperature, pH, or ionic strength, ensures that the application still can occur under harsh conditions.

The small size of nanobodies is highly advantageous especially in the field of molecular imaging as it enables rapid tumor accumulation and homogenous distribution as well as efficient blood clearance, contributing to high tumor-to-background ratios.

Nanobodies as herein described, for use in molecular imaging and/or as a diagnostic tool can be easily conjugated to several kinds of imaging agents and their high specificity renders their use relatively safe.

In some embodiments, the nanobodies as herein disclosed can be conjugated to radionuclides for use in radio-imaging. Single-photon emission computed tomography (SPECT) is based on $\gamma$-rays and sdAb of the present disclosure can thus linked to longer-lived radionuclides such as $^{99m}$Tc, $^{177}$Lu, $^{123}$I, $^{125}$I and $^{111}$In. On the other hand, shorter-lived radionuclides such as $^{68}$Ga, $^{124}$I or $^{89}$Zr, $^{64}$Cu, $^{18}$F, or $^{15}$O can be used for positron emission tomography (PET) purposes. Scintigraphy may use the same radionuclides as SPECT.

Other imaging agents usable is nanobody-targeted based imaging as per the present disclosure includes absorbing small-molecule dyes, metallic nanoparticles (photoacoustic imaging, PAI), small synthetic fluorescent probes, which popular imaging agent includes near-infrared fluorophores such as IRDye 800CW, Ag2S quantum dots and the FDA-approved indocyanine green, or fluorescent protein-expressing genes (fluorescence molecular tomography), luciferase expressing genes (bioluminescence imaging), Superparamagnetic iron oxide (SPIO), gadolinium-DTPA (magnetic resonance imaging), Nanoparticle-based contrast agents (computed tomography).

sdAbs are typically highly relevant in molecular imaging strategy due to their small size and fast clearance. They also possess high chemical and temperature resistance due to their small size and less complex 3D structure. This is thus favorable for molecular imaging procedures as well as for conjugation chemistry (production).

Anti-FGFR4 sdAbs as per the present disclosure can also be used in cell-based ELISA assays. To perform sandwich ELISA, both a capturing and detecting nanobody are used, preferably targeting different epitopes on the antigen.

In some embodiments of the present disclosure, the anti-FGFR4 single domain antibodies as herein described are thus useful for detecting the presence of FGFR4 in a biological sample. The term "detecting" as used herein encompasses quantitative or qualitative detection. In certain aspects, a biological sample comprises one or more cell(s) or tissue(s). In certain aspects, such tissues include normal and/or cancerous tissues that express FGFR4, notably that express FGFR4 at higher levels relative to other tissues or similar tissue from a control subject or from a control population of subjects.

Also included is a method of diagnosing a disorder associated with an increased expression of FGFR4, typically FGFR4-associated cancers or tumors. In certain aspects, the method comprises:

contacting a test cell with an anti-FGFR4 single domain
antibody of the present disclosure;
determining the level of expression (either quantitatively
or qualitatively) of FGFR4 on the test cell by detecting
binding of said humanized anti-FGFR4 sdAb to HER;
and
comparing the level of expression of FGFR4 in the test
cell with the level of expression of FGFR4 in a control
cell (e.g., a normal cell of the same tissue origin as the
test cell or a cell that expresses FGFR4 at levels
comparable to such a normal cell), wherein a higher
level of expression of FGFR4 on the test cell as
compared to the control cell indicates the presence of a
disorder associated with increased expression of
FGFR4. In certain aspects, the test cell is obtained from
an individual suspected of having a disorder associated
with increased expression of FGFR4. In certain aspects,
the disorder is a cell proliferative disorder, such as a
cancer or a tumor.

In certain aspects, a method of diagnosis or detection,
such as those described above, comprises detecting binding
of an anti-FGFR4 single domain antibody expressed on the
surface of a cell or in a membrane preparation obtained from
a cell expressing FGFR4 on its surface. An exemplary assay
for detecting binding of an humanized anti-FGFR4 sdAb to
FGFR4 expressed on the surface of a cell is a "FACS" assay.

Certain other methods can be used to detect binding of
humanized anti-FGFR4 sdAb as herein disclosed to FGFR4.
Such methods include, but are not limited to, antigen-
binding assays that are well known in the art, such as
western blots, radioimmunoassays, ELISA (enzyme linked
immunosorbent assay), "sandwich" immunoassays, immu-
noprecipitation assays, fluorescent immunoassays, protein A
immunoassays, and immunohistochemistry (IHC). Advan-
tageously in these embodiments humanized anti-FGFR4
sdAbs as herein disclosed are linked to a diagnostic com-
pound, in particular a detectable label, as previously
described.

In some embodiments of the methods as herein described,
the anti FGFR4 sdAb as herein disclosed is linked to a drug
nanocarrier, such as a liposome. Typically, said drug nano-
carrier functionalized with antiFGFR4 sdAb as herein dis-
closed encapsulates a diagnostic compound.

In the following, the invention will be illustrated by
means of the following examples and figures.

FIGURES LEGENDS

FIG. 1: Schematic overview of phage display biopanning
and preselection of FGFR4 binding nanobody sequences.
Phage display selection was performed on biotinylated and
Dynabeads®-bound FGFR4 with two different synthetic
nanobody phage display libraries. Enriched phage clones
were tested for their binding to cell-surface FGFR4 on
Rh4-FR4 wt cells resulting in 40 unique binders. Eight
nanobodies were chosen, expressed in E. coli and finally the
four candidates A8, B1, B5 and F8 bound to Rh4-FR4 wt but
not to Rh4-FR4ko cells.

Figure 2:
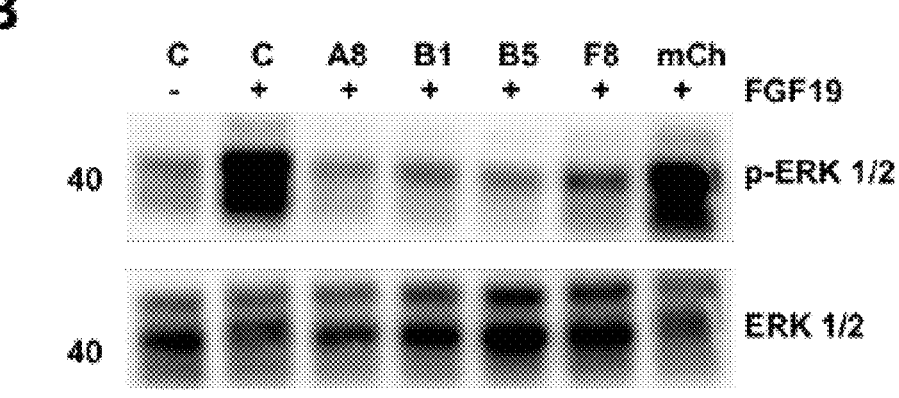

FIG. 2: In vitro binding validation of nanobodies. A)
Nanobodies were tested for their binding selectivity to cell
surface FGFR4 by flow cytometry. Histograms show the
single cell living population of each nanobody binding to
Rh4-FR4 wt versus Rh4-FR4ko cells. Secondary FITC
labelled anti HIS-tag antibody (2nd) was used as back-
ground control and mCherry (mCh) was used as negative
control. Median fluorescence intensities (MFI) were deter-
mined with FlowJo™ 10 software. B) Activation assay of FGFR4 in Rh30 cells was performed with recombinant
FGF19 and in combination with nanobodies. The cells were
incubated for 1 h with nanobodies at 10 µM (A8, B1, B5, F8,
mCh) followed by stimulation of FGFR4 with 50 nM FGF19
for 10 min. Control cells (C) were either not stimulated or
stimulated with FGF19 in absence of the nanobodies. The
cell lysates were analysed by western blot with anti phospho
ERK1/2 antibody. Total Erk1/2 levels are shown as loading
control.

Figure 3:
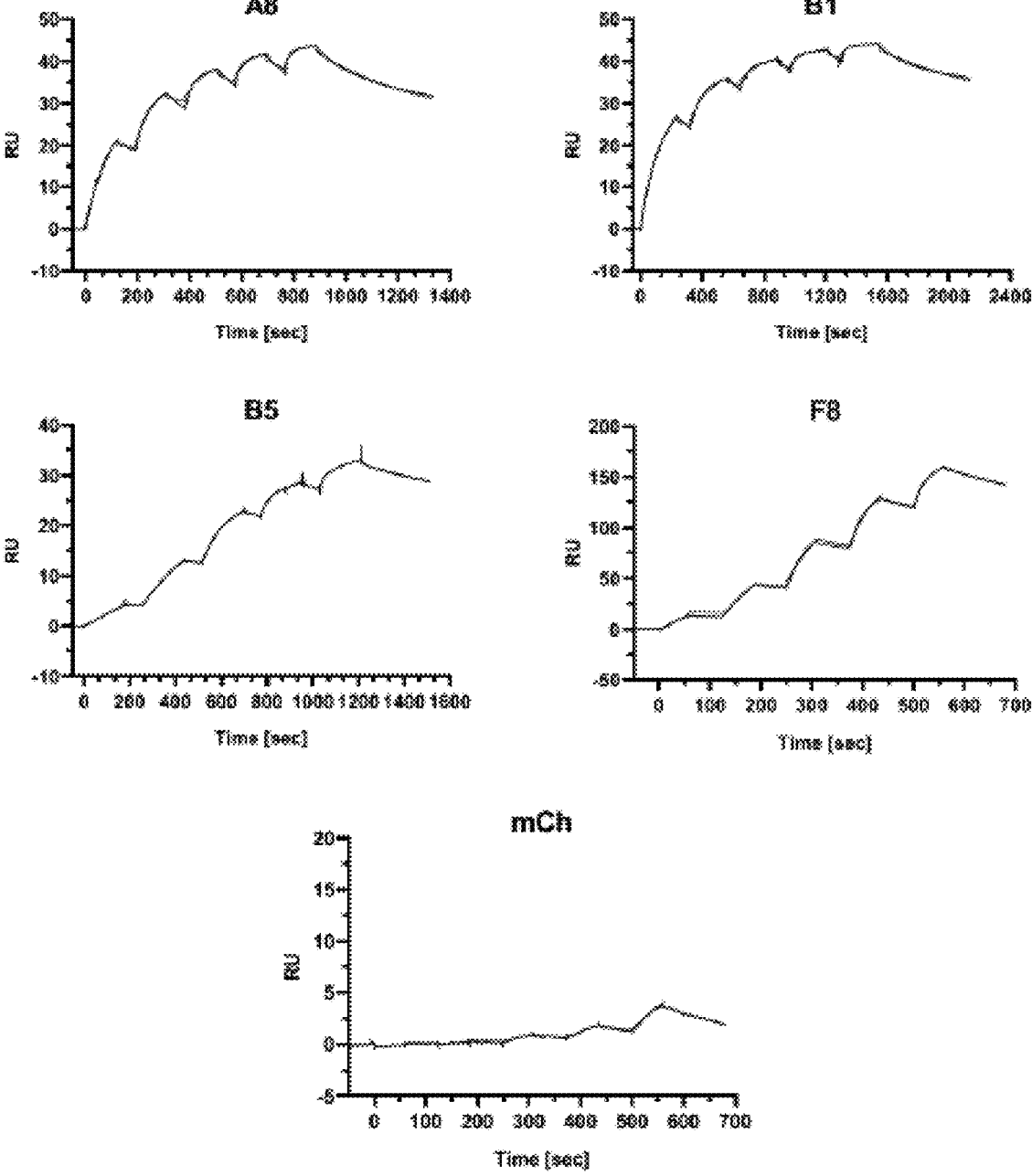

FIG. 3: Affinity determination of nanobodies to recombi-
nant protein via surface plasmon resonance spectroscopy.
Single cycle kinetics analysis was performed on immobi-
lized FGFR4 through covalent amine binding on the dextran
based sensor chip. The analytes A8, B1, B5, F8 and mCh
were injected in 5 different concentrations followed by a
dissociation phase. A final dissociation step was added after
the last injection step to determine Koff rates for the KD
calculations. The black curves represent the measured data
and red curves show the fit analysis (heterogeneous ligand
model) performed with the BIAevaluation software.

Figure 4:
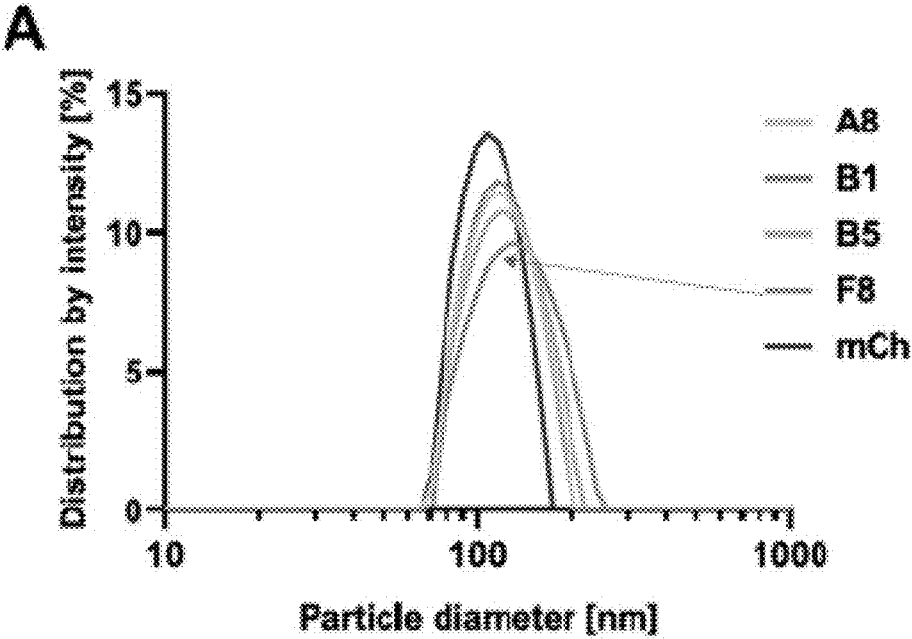
Figure 4:
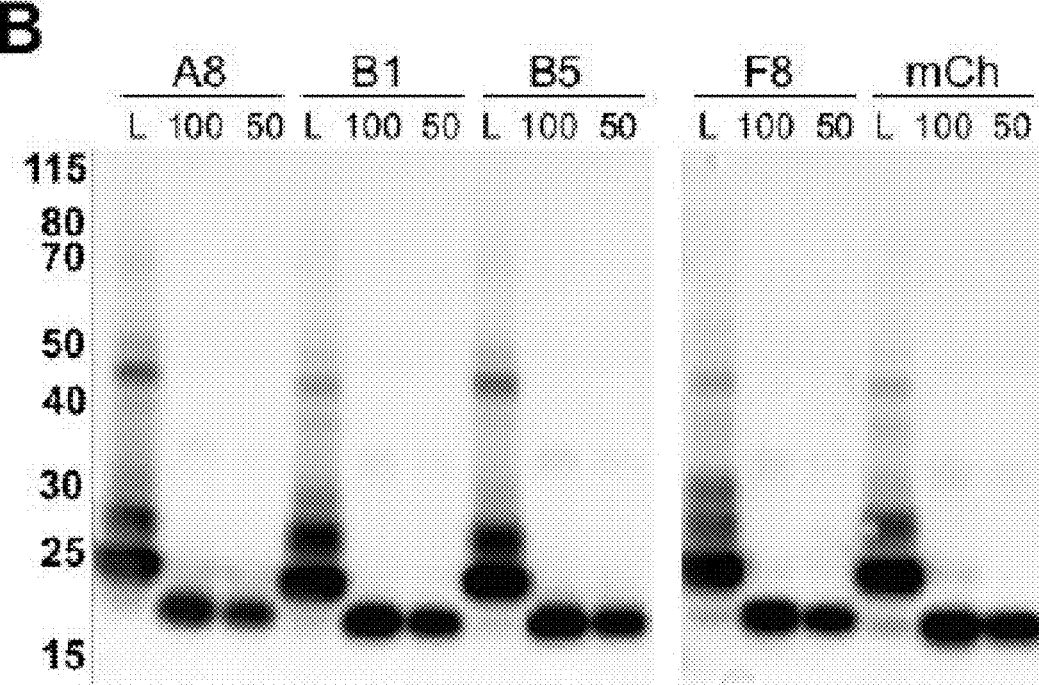

FIG. 4: Characterization of vincristine-loaded targeted
liposomes. A) Size distribution of nanobody-coated lipo-
somes measured by dynamic light scattering. B) Western
blot analysis of coupled nanobodies. Liposome suspensions
(L) equivalent to 100 ng of nanobodies were loaded under
reducing and denaturing conditions for gelelectrophoresis.
100 and 50 ng of uncoupled protein was loaded as control.
Nanobodies were detected with an anti His6-tag antibody.

Figure 5:
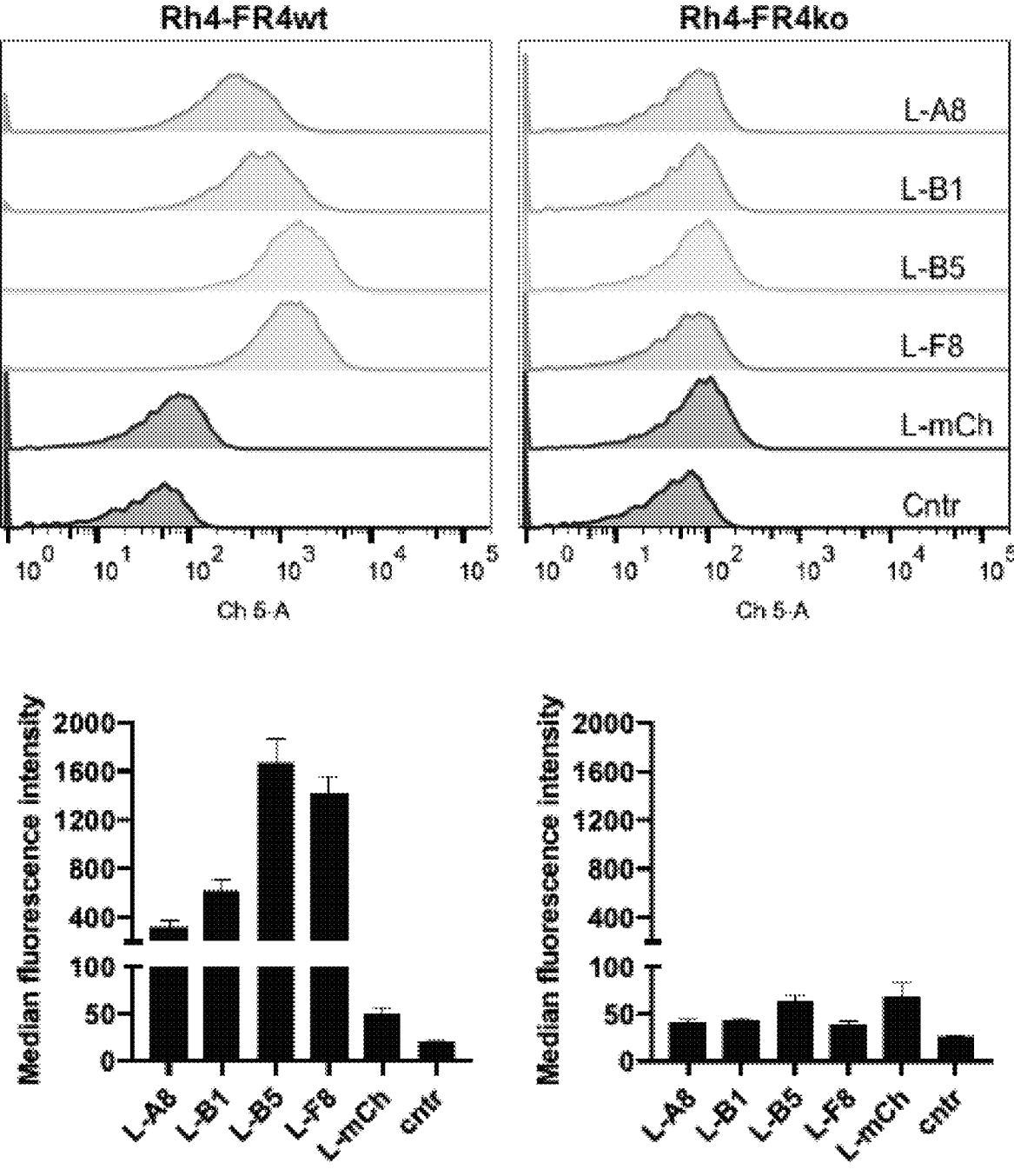

FIG. 5: In vitro binding validation of FGFR4 targeting
liposomes. Liposomes decorated with FGFR4 targeting
nanobodies A8, B1, B5 and F8 or mCh negative control were
tested for their binding selectivity to cell surface FGFR4 by
flow cytometry. Attached cells were incubated for 2 h with
0.5 mM total lipid concentration at 37° C. and 5% CO2.
Histograms show the single cell living population of lipo-
somes binding to Rh4-FR4 wt versus Rh4-FR4ko cells.
Non-treated cells represent the control populations. Median
fluorescence intensities (MFI) were determined with
FlowJo™ 10 software.

Figure 6:
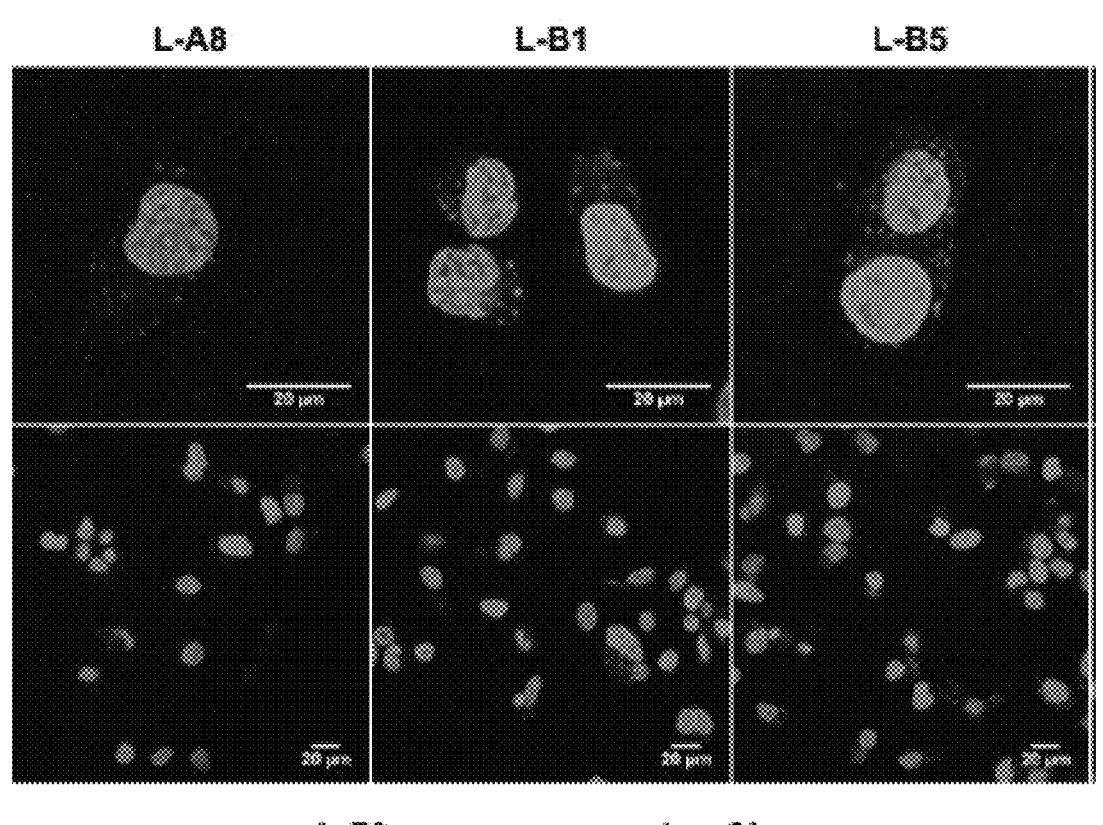
Figure 6:
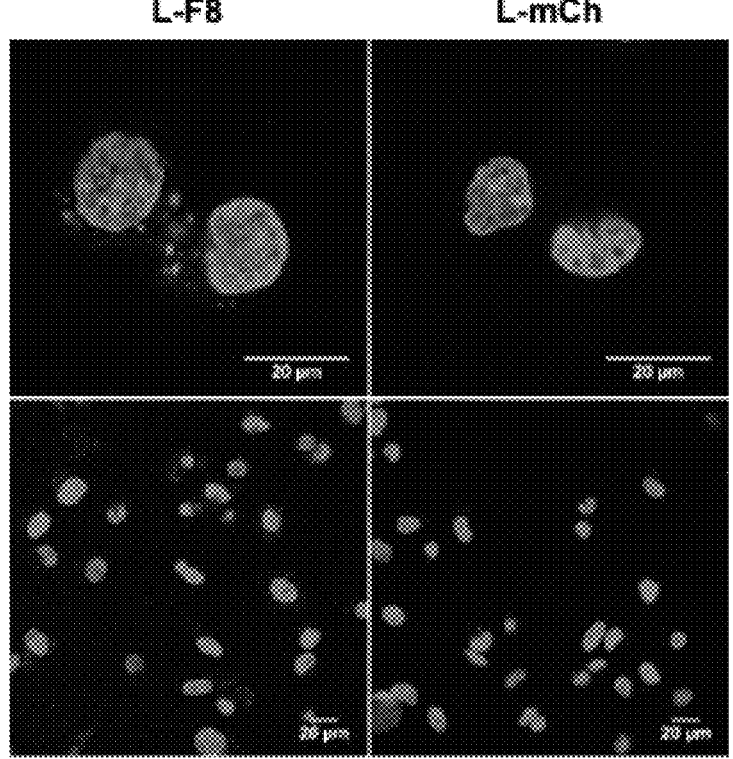

FIG. 6: Internalization of FGFR4 targeting liposomes.
Confocal microscopy analysis of Rh4-FR4 wt cells incu-
bated for 2 h at 37° C. and 5% CO2 with nanobody coated
fluorescent liposomes. The total lipid concentration was 3
mM. Cells were washed, fixed and mounted with DAPI
containing medium.

Figure 7:
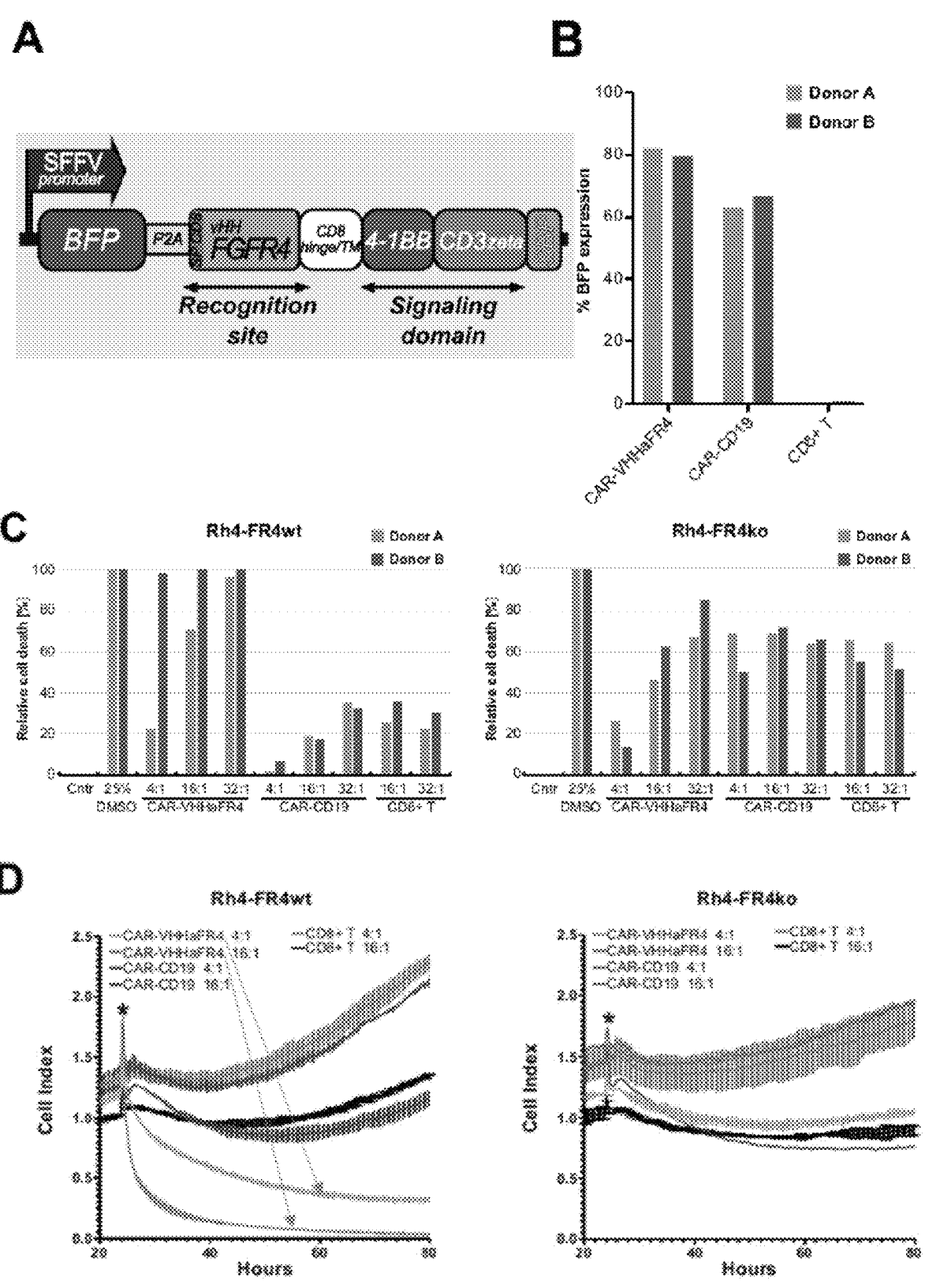

FIG. 7: Cytotoxicity of FGFR4-CAR T cells towards
RMS cells. A) Schematic representation of the CAR-
VHHaFR4 construct. The CAR is composed of the nano-
body A8 with CD8 alfa single peptide sequence and C-ter-
minal myc-tag followed by the hinge and transmembrane
(TM) domains of CD8 alfa. Intracellular signaling domains
are 4-1BB and CD3 zeta and are followed by a streptavidib
binding peptide (SBP). B) CD8+ T cell transduction effi-
ciencies of donor A and B were determined by flow cytom-
etry analysis of BFP signals. C) Cytotoxicity determined by
luciferase activity of Rh4 cells co-cultured for 72 h with
effector T cells of donors A and B. Relative cell death was
highest for Rh4-FR4 wt cells incubated with FGFR4-CAR T
cells at the indicated effector:target (E:T) cell ratios in both
donors. In Rh4-FR4ko cells, non-specific cell killing was
observed for the cocultivation of all CAR T cells and the
non-transduced CD8+ T cells. D) Real-time cell death
analysis of Rh4 cells co-cultured with effector T cells from
donor B using xCELLigence® RTCA DP. FGFR4-CAR T
cells showed higher killing activities at the indicated E:T cell
ratios in Rh4-FR4 wt wcompared to non-specific CD19-
CAR T cells or non-transduced CD8+ T cells. In Rh4-FR4ko cells no specific cytotoxicity was observed. The asterisks indicate the time of addition of the effector T cells.

EXAMPLES

Materials and Methods

Plasmids and Cloning

For recombinant protein expression, nanobody encoding sequences on the pHEN2 phagemid vector were PCR amplified with SapI-introducing primers for FX cloning[54] into pSB_init (kindly provided by M. Seeger lab, University of Zurich). The expression vector harbors a ccdB suicide cassette, a C-terminal cysteine and 6×His-tag. Successful cloning of nanobody sequences replaced ccdB and the constructs were amplified in E. coli MC1061. CAR T cell constructs were generated with the A8 nanobody sequence and was cloned by ligation to the pTRIP-BFP-2a-scFvCD19-myc-41BB-CD3zeta-SBP with the substitution of the scFvCD19 by A8 (pTRIP-BFP-2a-vHH-FGFR4-myc-41BB-CD3zeta-SBP). The pTRIP-BFP-2a-scFvCD19-myc-41BB-CD3zeta-SBP was previously generated by gene synthesis of the sequence composed of: single peptide CD8 alfa-single chain variable fragment against CD19-myc tag-hinge and transmembrane domain of CD8 alfa-stimulatory domains 4-1BB and the CD3zeta domain-Streptavidin binding peptide (SBP). This gene was cloned into the pTRIP-SFFV-tagBFP-2A.ape kindly provided by Nicolas Manel (Institut Curie, Paris)[55].

Cell Lines

The cell lines Rh4 (kindly provided by Peter Houghton, Research Institute at Nationwide Children's Hospital, Columbus, OH), Rh30, HEK293 ft HEK293T (purchased from ATCC, LGC Promochem) were maintained in DMEM supplemented with 10% FBS (both Sigma-Aldrich), 2 mM L-glutamine and 100 U/ml penicillin/streptomycin (both Thermo Fisher Scientific) at 37° C. in 5% $CO_2$. RMS cell lines were tested and authenticated by cell line typing analysis (STR profiling) in 2014/2015 and positively matched[48]. All cell lines tested negative for mycoplasma.

Generation of CRISPR/Cas9 FGFR4 Knockout Cells

Rh4 FGFR4 knockout clones were generated via CRISPR/Cas9 technology. Complementary single strand oligonucleotides encoding the sgRNA sequence for FGFR4 knockout (TTGCACATAGGGGAAACCGT) were annealed and cloned into the lentiCRISPRv2 puro vector (#98290, Addgene) via Esp3I (ER0451, Thermo Fisher Scientific) restriction and T4 ligation (15224017, Thermo Fisher Scientific). Lentiviral vectors were produced in HEK293T cells. The cells were transiently transfected with pMDL, pREV, pVSV-G and the lentiCRISPRv2-sgFR4Ex14 using JetPrime® (Polyplus Transfection). After 24 h, medium was replaced and virus supernatant was harvested after additional 48 h. The supernatant was filtered, 20-fold concentrated (Amicon® Ultra 15, Merck Millipore, 4000 g, 15 min) and stored at –80° C. Transduction of RMS cells was performed with concentrated viral supernatant in the presence of 10 µg/ml polybrene (Merck Millipore). After 24 h, medium was changed and puromycin selection at 1 µg/ml was started after 72 h and carried out for 7 days. Single cell cloning was performed with selected cells on 96-well plates and the FGFR4 knockout was confirmed on protein level by western blotting. All experiments were performed with the knockout clone #8.

Production of Lentiviral Vector for CAR T Cell Construction

Lentivirus particles were produced by co-transfection of the plasmid containing the genes of interest (BFP-2a-scFvCD19/sdAB-FGFR4-myc-41BB-CD3zeta-SBP), the packaging plasmid psPAX2 and envelop plasmid pVSVG into HEK293 ft using the polyethyleneimine (PEI) precipitation protocol. The cells were incubated at 37° C. with 5% $CO_2$ and the supernatant was harvested and saved after 48 h, followed by the addition of fresh medium for further 24 h of lentivirus production. After the 72 h, the supernatants were pooled together and filtered using a 0.2 µm-pore-size-filter. To concentrate the lentivirus particles, 20% sucrose in PBS was applied to the filtered supernatant followed by centrifugation at 100,000 g for 1.5 h at 4° C. The pellet was recovered in 1 mL of freezing medium (DMEM complete medium+0.1 mM β-mercaptoethanol (Gibco) and 1 mM HEPES (GIBCO)) and stored at –80° C. until use. Lentivirus titer was determined by flow cytometry thought the detection of fluorescent protein (mtag BFP) in HEK293 ft cells 72 h after transduction.

T Cell Isolation and Transduction

Peripheral blood mononuclear cells (PBMCs) were recovered using the density gradient Lymphoprep™ (StemCells). CD8+ T cells were isolated by negative selection using a cocktail containing antibodies against CD4, CD15, CD16, CD19, CD34, CD36, CD56, CD123, TCRγ/δ, and CD235a (Glycophorin A), according to the instruction of CD8+ T cell human isolation kit (Miltenyi). Isolated CD8+ T cells were then cultured in X-VIVO® medium (Lonza) supplemented with 50 µM of β-mercaptoethanol (Merck Millipore) and 5% Human Serum (Merck Millipore) and activated using Human T-activator CD3/CD28 Dynabeads® (Gibco) following the manufacture instructions. After approximately 24 h of T cell activation, the T cells were transduced with lentiviral particles mixed with 4 µg/mL of polybrene (Merck Millipore) at an MOI of approximately or higher than 5. Two days after, the medium was exchanged and replaced by fresh medium supplemented with 5 ng/mL recombinant human interleukin-2 (IL2; R&D Biosystem). The transduction efficiency was evaluated at day 6 or 7 after transduction through the detection of mtagBFP expressing cells using flow cytometry.

The healthy adult blood donors (Saint-Louis Etablissement Français du sang (EPS) or Saint-Antoine Crozatier EFS at Paris, France) consented to provide their blood for research purposes.

Phage Display Selection

Screening for FGFR4 was performed with biotinylated extracellular FGFR4 (G&P Biosciences) in native condition as described[56] using Nali-H1 library[24] composed of $3 \times 10^9$ synthetic humanized sdAb and Gimli library composed of $1.6 \times 10^9$ synthetic fully humanized sdAb.

Protein Expression and Purification

Periplasmic expression of nanobodies was performed in E. coli MC1061 harboring the pSB_init vector enabling protein production with a C-terminal cysteine and 6×His-tag. A 20 ml overnight pre-culture grown in Terrific Broth medium (25 µg/ml Chloramphenicol) was diluted in 2000 ml fresh medium and grown at 37° C. for 2 h. The temperature was then reduced to 25° C. and after 1 h protein expression was induced with 0.02% L-arabinose. The bacterial culture was grown overnight at 25° C. and cells were harvested by centrifugation (12000 g, 15 min). Periplasmic protein extraction was performed with the osmotic shock method. The cells were resuspended with 50 ml lysis buffer 1 (50 mM Tris/HCl, pH 8.0, 20% sucrose, 0.5 mM EDTA, 5 µg/ml lysozyme, 2 mM DTT) and incubated for 30 min on ice. After the addition of ice-cold lysis buffer 2 (PBS, pH 7.5, 1 mM $MgCl_2$, 2 mM DTT) the cell debris were harvested by centrifugation (3800 g, 15 min) and the protein containing supernatant was supplemented with a final concentration of 10 mM imidazole. 10 ml of Co$^{2+}$-beads slurry (HisPur™ Cobalt Resin, Thermo Fisher Scientific) were washed with wash buffer (PBS, pH 7.5, 30 mM imidazole, 2 mM DTT) and the supernatant was added to the beads. After an incubation of 1 h at 4° C. the beads were washed with 20 ml wash buffer and bound protein was eluted with 20 ml elution buffer (PBS, pH 7.5, 300 mM imidazole, 2 mM DTT). Prior size exclusion chromatography (SEC), the protein elution was dialyzed overnight into PBS, pH 7.5, 2 mM DTT and concentrated via spin filter centrifugation (Amicon® Ultra 15, 3 kDa, Merck Millipore).

Flow Cytometry

Binding validation of selected phages, recombinant nanobodies and decorated liposomes was performed on Rh4-FR4 wt and Rh4-FR4ko cells. Specificity of selected phage clones binding to FGFR4 was determined by flow cytometry in 96-well plates (Becton Dickinson). Cell surface staining of Rh4-FR4 wt or Rh4-FR4ko cells was performed on ice in PBS supplemented with 1% FBS. 80 µL phages+20 µL PBS/1% milk were incubated on 1×10$^5$ cells for 1 h on ice. After 2 washes in PBS, phage binding was detected by a 1:250 dilution of anti-M13 antibody (27-9420-01; GE healthcare) for 1 h on ice followed by a 1:400 dilution of A488-conjugated anti-Mouse antibody (715-545-151; Jackson ImmunoResearch, Europe Ltd) for 45 min. Samples were analyzed after two washes by flow cytometry on a MACSQuant® cytometer (Miltenyi) and results were analyzed with FlowJo™ software (BD Biosciences, France). Phages displaying anti-mCherry nanobodies were used as negative control[24] and as positive control we used an anti-FGFR4 antibody (BT53, kindly provided by J. Khan lab, NCI, Bethesda, MD). For binding test of recombinant nanobodies, cells were detached with Accutase® (Stemcell Technologies) and washed with PBS. All following steps were performed on ice: 4×10$^5$ cells were incubated with nanobody concentrations of 30 µg/ml for 1 h, washed once with PBS and incubated for an additional 30 min with anti His-tag FITC labeled antibody (LS-C57341, LSBioscience, diluted 1:10). The cells were washed once more with PBS and analyzed. Targeting liposomes were added at 0.5 mM final lipid concentration to cells in 96-well plates and incubated for 2 h at 37° C. and 5% CO$_2$. The cells were washed twice with PBS and detached with Accutase®. All flow cytometry measurements were performed with Fortessa™ flow cytometer (BD Biosciences) and the data were analyzed using FlowJo™ 10.4.1 software.

Receptor Activation Assay

To test the effect of nanobodies on FGFR4 activation, 6×10$^4$ Rh30-FR4 wt and Rh30-FR4ko cells were plated on 24-well plates. The next day, nanobodies were added at 10 µM concentrations to the cells in FBS-free medium and incubated for 1 h at 37° C. prior to stimulation with 50 nM recombinant human FGF19 (Peprotech) for 10 min. Cells were immediately washed with ice cold PBS and lysed in Tris/RIPA buffer (50 mM Tris HCl, pH 7.5, 150 mM NaCl, 10% NP40, 0.5% Na-Deoxycholate, 0.1% SDS, 1 mM EGTA, with standard protease and phosphatase inhibitors). Total cell extracts were then analyzed by western blotting.

Western Blotting

SDS-PAGE samples were separated on 4-12% NuPAGE Bis-Tris gels (Thermo Fisher Scientific) and blotted on Trans-Blot® Turbo™ Transfer Blot membranes (Biorad). After blocking the membranes with blocking buffer (5% milk/TBST) for 1 h at room temperature, the primary antibody was added at a 1:1000 dilution and incubated overnight at 4°. The secondary HRP-conjugated antibody was diluted 1:10'000 in blocking buffer and added to the washed membrane for 1 h at room temperature. Chemiluminescence was detected after incubation with Amersham™ ECL™ detection reagent (GE Healthcare) or SuperSignal™ West Femto Maximum Sensitivity Substrate (ThermoFisher Scientific) in a ChemiDoc™ Touch Imaging system (Bio-Rad). Primary antibodies used were phospho-p44/42 MAPK Thr202/Tyr204 (#9101), O-Tubulin D3U1W (#86298), FGF Receptor 1 D8E4 (#9740) (all from Cell Signaling Technology), FGF Receptor 2 C-17 (sc-122), FGF Receptor 3 B9 (sc-13121) and FGF Receptor 4 A-10 (sc-136988) (all from Santa Cruz Biotechnology). Secondary antibodies were anti-rabbit IgG (#7074, Cell Signaling Technology) and anti-mouse IgG (#7076, Cell Signaling Technology).

Surface Plasmon Resonance Spectroscopy

Single cycle kinetics analysis was performed with the BIAcore® T200 instrument (GE Healthcare) on CMD200M sensor chips (XanTec bioanalytics GmbH) activated with a mixture of 300 mM NHS (N-hydroxysuccinimide) and 50 mM EDC (N-ethyl-N'-(dimethylaminopropyl) carbodiimide). Recombinant FGFR1, FGFR2, FGFR3 and FGFR4 (G&P Biosciences) were immobilized on the activated biosensors (800 to 12,000 RU; 1 RU=1 pg/mm$^2$) followed by a blocking step with 1M ethanolamine. One flow channel per chip was used as a reference to provide background corrections. The nanobodies were injected at 5 different concentrations followed by a dissociation phase. K$_{off}$-rates were determined from a final dissociation step after the last injection. The measurements with FGFR4 were performed for each nanobody on freshly immobilized protein due to strong binding and incomplete dissociation from the surface. Immobilization flow rate was 5 µl/min and binding studies were performed at 30 µl/min. Binding parameters were determined with the heterogeneous ligand model fit of the BIAevaluation software. The black curves represent the measured data and red curves show the performed fit analysis.

Preparation of Fluorescently-Labelled VCR-Loaded Liposomes

The production of liposomes and vincristine loading was performed as described[23], with minor modifications. Liposomes were produced with the film-hydration/extrusion method with egg sphingomyelin (Lipoid GmbH), cholesterol (Sigma Aldrich), PEG-ceramide (N-palmitoyl-sphingosine-1-[succinyl[methoxyPEG-2000]]), DSPE-PEG-maleimide (1,2-distearoyl-sn-glycero-3-phosphoethanolamine-N-[maleimide (polyethylene glycol)-2000]) (both Avanti Polar Lipids) and DiR (1,1'-dioctadecyl-3,3,3',3'-tetramethylindotricarbocyanine Iodide) (Thermo Fisher Scientific) at a ratio of 49.8:45:4:1:0.2 mol %, respectively. The lipid film was hydrated with citrate buffer (250 mM, pH 3) resulting in a concentration of 70 mM of total lipids. Next, six freeze-thaw cycles and ten extrusion steps with a LIPEX® Thermobarrel extruder (Evonik Nutrition and Care GmbH) and a 100 nm pore-size polycarbonate membrane (Whatman) were performed. A transmembrane pH gradient was generated via gel exclusion chromatography with PD Midi-Trap™ Sephadex® G-25 columns (GE Healthcare Lifesciences). The columns were conditioned with coupling buffer (PBS, pH 7.0) and the eluted liposome suspensions (14 mM) was used for vincristine encapsulation. For a molar drug-to-lipid ratio of 0.05, 1 ml of liposomes were mixed with 1 ml of 0.7 mM VCR (VincristineTeva, Teva Pharma AG) diluted in coupling buffer and incubated for 1 h at 65° C. Non-encapsulated VCR was removed via spin filter centrifugation (Amicon® Ultra 0.5, 100 kDa, Merck Millipore) and encapsulation reactions were concentrated to 11.2 mM suspensions.

Decoration of Liposomes with Nanobodies

For coupling of the nanobodies to the liposomal surface, the proteins were buffer exchanged into coupling buffer (PBS, pH 7.0) with PD MiniTrap™ Sephadex® G-25 columns (GE Healthcare Lifesciences). A nanobody to lipid ratio of 0.4 nmol/μmol was chosen for the reaction[45] resulting in approximately 30 nanobodies per liposome. The reaction was incubated over night at 4° C. and non-coupled nanobodies were removed by two steps of washing and filtration via spin filter centrifugation (Amicon® Ultra 0.5, 100 kDa, Merck Millipore). The mean diameter and polydispersity index (PDI) of liposomes were measured by dynamic light scattering (Litesizer™ 500, Anton Paar). To estimate the amount of nanobodies coupled to the liposomes, gel electrophoresis was performed with labelled liposomes and defined amounts of corresponding nanobodies under denaturing and reducing conditions. Sample separation, western blotting and imaging was performed as described above with anti His-tag antibody (ab 18184, Abcam).

VCR Quantification

Quantification of vincristine concentrations was performed via HPLC (Ultimate™ 3000 HPLC system, Thermo Fisher Scientific) with an RP-18 (5 μm, 4.6×250 mm) LiChrospher® 100 column (Merck). A calibration curve for vincristine ranging from 890 μg/ml to 13.9 μg/ml was prepared and liposome samples were disrupted with methanol for analysis. Doxorubicin was mixed to all samples, serving as an internal standard. A di-potassium phosphate buffer (50 mM, pH 3.2) was used as mobile phase (68%) with a mixture of acetonitrile/UPW 90/10 (v/v; 32%) for 30 min at a flowrate of 1.5 ml/min. 20 μl of each sample were injected and detection occurred with the UV-VIS detector at 230 nm. Drug-loading efficiency was determined by analyzing vincristine concentrations in the spin-filter purified liposome suspension and the aqueous flow-through. The encapsulation efficiency represented the percentage of vincristine in the liposome suspension compared to the combined amount of vincristine from filtered liposomes and flow-through.

Confocal Microscopy

Detection of cell binding and internalization of fluorescent liposomes was performed on Rh4 wildtype and Rh4-FGFR4-knockout cells via confocal laser scanning microscopy (CLSM-Leica SP8 inverse). 40'000 cells were seeded in a four-well microscopy slide (Falcon™ Chambered Cell Culture Slides, Fisher Scientific). The next day, targeted or control liposomes were added to the cells at a final lipid concentration of 3 mM, and incubated for 2 h at 37° C. and 5% $CO_2$. The wells were then washed twice with PBS and the cells were fixed for 15 min with 4% formaldehyde solution. After two further washing steps with PBS, the slides were separated from the chamber case and mounted with DAPI-containing medium (VECTASHIELD® Hardset Antifade Mounting Medium with Phalloidin, Vector Laboratories). Microscopy imaging was performed with 63× objective (HC PL APO CS2 63×/1.30) and the lasers Diode405 and Diode638 for DAPI and DiR excitation, respectively. All images were processed with ImageJ.

CAR T Cell Cytotoxicity Assays

Two methods were used to evaluate the cytotoxicity of T cells toward RMS cells. For the bioluminescence assay, Rh4-FR4 wt and Rh4-FR4ko cells were transduced with lentiviral particles to express three proteins together as an operon (P2A), mtag BFP, Red Firefly luciferase and the puromycin resistant gene (BFP-P2A-Luciferase-P2A-Puromycin). Briefly, the target cells were plated (4000 cells/well) in a 96-well ViewPlate™ Black (Perkin-Elmer) in DMEM complete medium and effector cells (CD8+ T cells) were added the next day at the indicated effector to target (E:T) ratios in X-ViVO® medium (2-fold volume compared to DMEM). After approximately 72 hours of incubation at 37° C. and 5% $CO_2$, the wells were washed twice with PBS and 1-2 mg/mL of luciferin substrate (Perkin Elmer) in PBS was added for 10 min (37° C.) prior to luminescence measurement with FLUOstar® OPTIMA (BMG LabTech). The percentage of cell survival was calculated by taking the luminescence values for each point and by dividing it by the highest value of luminescence obtained. Real-time cell death measurements were performed with the xCELLigence® real-Time Analyzer System (ACEA Biosciences). Briefly, the target cells were plated (10,000 cells/well) in a 16-well E-plate (ACEA Biosciences) in DMEM complete medium and the next day the effector cells were added at indicated E:T ratios in X-Vivo® medium (2-fold volume compared to DMEM). Cell index (relative impedance) was monitored in real time every 15 min for about four days at 37° C. and 5% $CO_2$. Horizontal lines within the curves indicate the SD of the duplicate wells used during the assay.

Results

Phage Display Selection of FGFR4-Specific Nanobodies

The screening of FGFR4-binding nanobodies was performed on two synthetic phage display libraries, the humanized sdAb library NaLi—H1[24] and the fully humanized sdAb library Gimli. We performed two independent phage display selections with three rounds of biopanning against recombinant FGFR4 (FIG. 1). In order to verify the binding specificity for FGFR4, we generated FGFR4 knockout cells RMS cells by CRISPR/Cas9, and tested 80 phage clones from each screening for their binding to Rh4 FGFR4 wild-type cells (Rh4-FR4 wt) and Rh4 FGFR4 knockout cells (Rh4-FR4ko). Flow cytometry analysis revealed 24 NaLi—H1 library and 55 phage clones from Gimli library binding to the Rh4-FR4 wt cells only. Sanger sequencing of the 79 phage clones confirmed 12 unique nanobodies from the NaLi—H1 and 28 from the Gimli library. Next, four phage clones from each library (i.e. NaLi—H1: A8, B1, B5, C3; Gimli: A4, F8, F11, H2) that showed the best binding to Rh4-FR4 wt by flow cytometry (data not shown) were expressed recombinantly. As negative control, we expressed an anti-mCherry nanobody (mCh)[24]. Recombinant nanobodies of approximately 17 kDa were engineered to be expressed with a C-terminal Myc/6×His-tag and an additional cysteine for maleimide coupling to the liposomal surface. 6×His-tag purification and size exclusion chromatography resulted in proteins of high purity (Suppl. FIG. 2), with yields in the range of 3-16 mg per liter of bacterial culture.

Selected Nanobodies Bind to RMS Cells and Inhibit Receptor Signaling

Validation of the binding of recombinant nanobodies to cell-surface expressed FGFR4 was performed with Rh4-FR4 wt and Rh4-FR4ko cells by flow cytometry. A FITC-labeled anti-6×His-tag antibody was used to detect surface-bound nanobodies. Four of the recombinant nanobodies tested displayed no significant binding to Rh4-FR4 wt cells (C3, A4, F11, H2, data not shown) whereas recombinant nanobodies A8, B1, B5 and F8 showed a specific binding to Rh4-FR4 wt cells and no binding to Rh4-FR4ko cells (FIG. 2A). As expected, the anti-mCherry negative control nanobody did not bind to Rh4-FR4 wt nor to Rh4-FR4ko cells. Median fluorescence intensities (MFIs) of the four FGFR4 binders incubated with Rh4-FR4 wt cells were in the range of 400, but anti-mCherry negative control, or the anti-6× His-tag antibody only displayed MFI of 200 (FIG. 2B), ing in two $K_D$ values for each candidate. Measurements of the affinities to the receptor family isoforms FGFR1 and FGFR3 showed as expected no binding of the analytes. The SPR data confirmed the strong binding of all candidates to FGFR4 and suggests that B1 and F8 have a strict FGFR4 specificity.

TABLE 2

| | Surface plasmon resonance spectroscopic determination of nanobody binding affinities to FGFR4. | | | | | | | |
|---|---|---|---|---|---|---|---|---|
| Nano-body | $k_{on}1$ (1/M*s) | $k_{off}1$ (1/s) | $k_D1$ (M) | $k_{on}2$ (1/M*s) | $k_{off}2$ (1/s) | $k_D2$ (M) | $R_{max}1$ (RU) | $R_{max}2$ (RU) |
| A8 | 3.14E+05 | 1.32E−09 | 4.22E−15 | 6.67E+04 | 2.45E−03 | 3.68E−08 | 25.6 | 18.1 |
| B1 | 1.11E+06 | 1.18E−06 | 1.06E−12 | 2.16E+05 | 9.92E−04 | 4.60E−09 | 26.1 | 17.5 |
| B5 | 1.84E+06 | 5.66E−04 | 3.08E−10 | 1.73E+05 | 3.75E−08 | 2.16E−13 | 23.1 | 10.3 |
| F8 | 5.45E+04 | 1.04E−06 | 1.91E−11 | 1.35E+06 | 5.57E−03 | 4.14E−09 | 83.0 | 86.4 |
| mCh | 2.60E+03 | 5.11E−03 | 1.96E−06 | 2.32E+03 | 5.05E−03 | 2.18E−06 | 20.7 | 20.7 | similar to the binding to Rh4-FR4ko cells, with a slightly higher value for B5 candidate.

The extracellular domain of FGFR4 has a high amino acid homology to FGFR1, 2 and 3. For an optimal targeting of RMS tumors, we aim to identify binders specific for FGFR4 only. Rh4-FR4 wt and Rh4-FR4ko cells both express FGFR1 and FGFR2, even though Rh4-FR4ko levels are slightly lower than Rh4-FR4 wt (Suppl. FIG. 1), we conclude that the nanobodies are specific for FGFR4 and do not bind to FGFR1 or FGFR2. Taken together, the binding validation of nanobodies on RMS cells revealed four FGFR4-targeting nanobody candidates.

Aberrant FGFR signaling is implicated in various types of cancer. In RMS, besides overexpression, FGFR4 has been shown to harbor activating mutations in over 6% of all tumors, resulting in constitutive tumor promoting signaling within the cells[3,32]. FGFR4 initiates four major signaling pathways: RAS-MAPK, PI3K-AKT, PLCγ and STAT[33]. We therefore tested the effect of the selected nanobodies on FGFR4 activation and downstream signaling. FGFR4 activation assays were performed on Rh30 cells and ERK 1/2 phosphorylation was used as a read-out. We incubated Rh30 cells with FGF19, the specific ligand for FGFR4, with or without prior addition of nanobodies (FIG. 2C). As expected, FGF19 led to a drastic increase of phospho-ERK 1/2 levels. Remarkably, kinase activation was absent when Rh30 cells were preincubated with the selected nanobodies, whereas negative control anti-mCherry did not block ERK 1/2 phosphorylation. These data show that the selected nanobodies have the ability to block activation of the FGFR4 downstream MAPK pathway in RMS cells.

Nanobodies High Affinity Binding to FGFR4

To determine the binding affinity of the nanobodies to FGFR4, we performed surface plasmon resonance (SPR) spectroscopy with recombinant FGFR4. As already mentioned above, FGFR1 and FGFR2 are expressed on Rh4-FR4ko cells and flow cytometry analysis indicated no binding of the nanobodies to the cells. To further confirm FGFR4-specificity, we included also affinity measurements with recombinant FGFR1, FGFR2 and FGFR3. Nanobodies A8, B1, B5, F8, and mCh were injected in five different concentrations on a FGFR coated chip. Except for the negative control mCh, calculated $K_D$ values for FGFR4 binding were in the nano- and picomolar range (FIG. 3; Table 2). Affinity parameters could not be fitted with a 1:1 binding model and best fits were obtained with the heterogeneous ligand model of the BIAevaluation software result- Preparation and Characterization of VCR-Loaded Targeting Liposomes In a previous study, we have optimized the formulation of liposomal VCR[23]. Here, in order to produce actively targeted liposomes, we introduced DSPE-PEG lipids with reactive maleimide groups at the distal end. Nanobodies harboring a free cysteine at the C-terminus were then coupled to the liposomal surface. Fluorescent liposomes composed of egg sphingomyelin, cholesterol, PEG-ceramide, DSPE-PEG-maleimide and DiR (49.8:45:4:1:0.2 mol %) were prepared by the film-hydration/extrusion method followed by VCR encapsulation and nanobody coupling. Dynamic light scattering measurements of decorated liposomes L-A8, L-B1, L-B5, L-F8 and L-mCh revealed hydrodynamic diameters of approximately 120-135 nm and low PDI values of 0.03-0.13 (FIG. 4A; Table 2).

Nanobody coupling to the liposomes was analyzed by western blotting with an anti-6×His-tag antibody. Samples of liposome suspensions were prepared with a theoretical nanobody amount of 100 ng. To estimate the coupling efficiency, we loaded 100 ng and 50 ng of corresponding recombinant nanobodies on the western blot gel (FIG. 4B). All liposome suspensions showed a dominant fraction running at an apparent size of 25 kDa, corresponding to one nanobody molecule (17 kDa) bound to DSPE-PEG-maleimide (2.9 kDa). Two further bands appear at a higher size suggesting the formation of complexes of two or three lipid molecules per nanobody. Besides the C-terminal cysteine, nanobodies have two further cysteines forming an intramolecular disulfide bond and representing possible reaction sites for the maleimide groups. Notably, there was only a faint band corresponding to free nanobodies in all the liposome samples.

To determine the encapsulation efficiency of VCR, we performed HPLC analysis with the VCR encapsulation reaction and all targeted liposomes after their final purification. VCR encapsulation efficiency was high, with 97.8% of the drug entrapped in the nanovesicles, and VCR concentrations of targeted liposomes were in the range of 250-320 µg/ml (Table 3).

Taken together, we were able to produce fluorescently-labelled VCR-loaded and nanobody-coated liposomes with a similar drug concentrations and size distributions between the samples.

TABLE 3

| Characterization of FGFR4-targeting and VCR-loaded liposomes. | | | | | |
|---|---|---|---|---|---|
| | L-A8 | L-B1 | L-B5 | L-F8 | L-mCh |
| Hydr. diameter (nm) | 126 | 127 | 129 | 136 | 122 |
| PDI | 0.129 | 0.108 | 0.093 | 0.122 | 0.025 |
| VCR conc (μg/ml) | 308.4 | 253.8 | 254.6 | 270.3 | 319.9 |

FGFR4-Targeting Liposomes Bind Specifically to FGFR4 Positive RMS Cells and are Internalized

We next wanted to test if nanobodies on the liposomal surface can still bind to FGFR4 expressing RMS cells. Rh4-FR4 wt and Rh4-FR4ko cells were incubated for 2 h with FGFR4-targeted liposomes or mCherry-targeted control liposomes under normal cell culture conditions.

DiR fluorescence was subsequently analyzed by flow cytometry (FIG. 5). Rh4-FR4 wt incubated with FGFR4-targeted liposomes showed an increased fluorescent signal, indicating binding to FGFR4, while no increase in fluorescence was observed in Rh4-FR4ko cells incubated with FGFR4-targeted liposomes. Rh4-FR4 wt incubated with control mCherry-targeted liposomes had an MFI similar to non-treated cells below 50. Among the FGFR4-targeted liposomes, MFI values ranged between 300, 600, 1700 and 1400 for L-A8, L-B1, L-B5 and L-F8, respectively, and thus were 6-, 12-, 34- and 28-fold increased over the MFI value of L-mCh. These results show that nanobodies are still able to bind specifically to Rh4-FR4 wt when coupled to the surface of VCR-loaded liposomes, but binding intensities differed between the four nanobodies.

It is a well-known phenomenon that receptor-mediated internalization of drug-loaded liposomes increases intracellular drug amounts and thus enhances their therapeutic effect[34]. We therefore investigated internalization of FGFR4-targeted liposomes by confocal microscopy. The liposomes were incubated for 2 h on Rh4-FR4 wt and Rh4-FR4ko cells. Subsequently, images of the fixed cells revealed a clear intracellular uptake of all liposomes coated with FGFR4-targeting nanobodies. Remarkably, no fluorescent signal was detected when Rh4-FR4 wt cells were incubated with L-mCh (FIG. 6). Consistent with the flow cytometry data, L-A8 and L-B1 showed a weaker intracellular fluorescence. Strikingly, no fluorescence could be observed in Rh4-FR4ko cells, supporting their specificity for FGFR4 (Suppl. FIG. 4). Therefore, FGFR4-targeted liposomal formulations represent a specific drug-delivery platform for FGFR4 overexpressing RMS tumor cells, characterized by their rapid and specific receptor-mediated intracellular uptake.

FGFR4-CAR T Cell Targeting of RMS Cells

To investigate the therapeutic potential of the selected nanobodies, we generated a chimeric antigen receptor (CAR) to produce T cells against FGFR4. The A8 nanobody was used to substitute the CD19 targeting single chain antibody fragment (scFv) in a CD19-CAR T construct (Celgene, Juno Therapeutics and Kymriad, Novartis), currently used in hematologic cancer therapy[25,35]. The resulting CAR (CAR-sdAbaFGFR4) is composed of the myc-tagged A8 followed by the hinge and transmembrane domains of CD8 alpha and the intracellular signaling domains of 4-1BB and CD3 zeta (FIG. 7A). CD8+ T cells were isolated form four healthy donors (donor A, B, C and D) and were transduced with FGFR4 or CD19 targeting CARs. Transduction efficiency was measured by mtagBFP expression which showed about 80% FGFR4-CAR and 60% CD19-CAR positive cells (FIG. 7B, Suppl. FIG. 5A). To assess the cytotoxic potency of the CAR T cells against Rh4-FR4 wt and Rh4-FR4ko cells we applied bioluminescence and real-time cell death assays (FIG. 7C, D). The RMS cells were co-cultured with CAR T cells at different ratios (E:T—Effector T cell to Target RMS cell), and as an additional control we used non-transduced CD8+ T cells. The bioluminescence assay was performed with T cells from donor A and donor B, and revealed specific killing of Rh4-FR4 wt by FGFR4-CAR T cells (FIG. 7C). T cells from donor B showed higher cytotoxic efficiencies with almost 100% dead cells at the lowest E:T ratio of 4:1. By comparing the cell death at E:T ratios of 32:1 between the T cells, we could verify the selective cytotoxic effect of FGFR4-CAR T cells with almost 100% dead cells. CD19-CAR T cells and CD8+ control T cells reached only values of approximately 20-35% dead cells. T cell mediated toxicity towards Rh4-FR4ko cells was similar for both CARs and CD8+ control T cells. Real-time analysis of cell death with CARs from donors B, C and D showed similar results, with selective cell killing of Rh4-FR4 wt by FGFR4-CAR T, but absent or reduced cytotoxicity in Rh4-FR4ko cells (FIG. 7D, Suppl. FIG. 5B). Taken together, these data showed that the selected nanobody A8 can generate FGFR4-CAR T cells that mediate significant antitumor activity against FGFR4-expressing RMS cells in vitro and therefore represent a promising further targeted treatment option.

Discussion

We report here the development of two therapeutic strategies for RMS by targeting FGFR4 with nanobodies, and validated them on RMS cells. We have selected four FGFR4 binding nanobodies and tested them in vitro for active drug delivery and cell-mediated immunotherapy. VCR-loaded fluorescently-labelled FGFR4-targeting liposomes showed selective binding and internalization when incubated with RMS cells. Moreover, we were able to generate FGFR4-CAR T cells with one nanobody candidate resulting in specific cytotoxicity against FGFR4 expressing RMS cells.

The four selected nanobodies A8, B1, B5 and F8 do not only bind to FGFR4 expressing RMS cells but are also able to block the FGFR4-FGF19 MAPK signaling axis. Although our aim was to select nanobodies to target FGFR4 for active drug delivery rather than its function, it is noteworthy that receptor signaling could also represent a therapeutic target in RMS[32,36]. In ARMS, FGFR4 is a direct target gene of the fusion protein PAX3-FOXO1[37], and in ERMS FGFR4 is frequently amplified with 12% of the tumors harboring activating mutations of the receptor[38-40]. Moreover, FGFR4 is not only implicated in RMS tumorigenesis. FGFR4 drives tumor progression in FGF19 expressing hepatocellular carcinomas and head and neck squamous cell carcinomas[41-43] and it is estimated that 0.5% of all tumors display abnormalities in FGFR4[44]. The selected nanobodies could therefore also serve as possible therapeutic approach in other cancers.

Surface plasmon resonance spectroscopy of nanobodies binding to FGFR4 revealed strong affinities in the order of nano- to picomolar. The measured data could not be fitted with a 1:1 binding model. Best fits were obtained with the heterogeneous ligand model indicating two separate binding affinity parameters for the nanobodies to FGFR4. We had to directly immobilize recombinant FGFR4 to activated carboxyl groups on the sensor chip through amine group binding, since other approaches were not compatible with our measurements. Therefore, it is possible that the non-oriented binding of FGFR4 to the sensor chip could have led to a complete or partial steric hindrance of the nanobody binding site, resulting in heterogeneous binding parameters. This is obvious when comparing $R_{max}$ values, representing the maximal nanobody binding signal: for the affinity measurements of A8, we could immobilize 800 RU FGFR4 to the sensor chip. With approximate molecular weights of 40 kDa for the ligand and 17 kDa for the nanobody, we would expect an $R_{max}$ of 340 RU (($MW_{FGFR4}/MW_{NB}$)*800 RU) but actually a value of only 44 RU was achieved. Since we were not able to fully regenerate the flow cells after nanobody binding, we performed all measurements with freshly immobilized FGFR4 for each nanobody. This resulted in different amounts of immobilized FGFR4. A8, B1 and B5 analysis was performed with approximately 800 RU of FGFR4 whereas for F8 and mCh we immobilized 9000 and 12'000 RU, respectively. The measurement of negative control mCh on such high ligand densities forced unspecific interactions at high nanobody concentrations. This resulted in low calculated affinities compared to the nanobody candidates.

Both free and liposome-conjugated nanobodies bound specifically to Rh4-FR4 wt cells and showed no binding to Rh4-FR4ko.

The formulation of liposomal VCR was modified by the introduction of DSPE-PEG-maleimide at 1 mol %. We were able to produce liposomes of comparable quality, size and drug-loading efficiencies as described before[23]. Nanobody coupling to the surface was performed as described by Oliveira and colleagues[45] with 0.4 nmol nanobodies per µmol of total lipids and resulted in high coupling efficiencies. We have also tested higher ratios of nanobody to lipids within the coupling reaction, but this resulted in precipitation of the liposomes. The small fraction of uncoupled nanobodies in the liposome suspension is negligible and did not interfere with our binding validation on cells.

The fluorescent FGFR4-targeting liposomes showed by confocal microscopy a very specific internalization in Rh4-FR4 wt cells represented by dot like structures within the cells which were absent in Rh4-FR4ko. The images were taken after 2 h of incubation, indicating a rather fast internalization process that can be an advantage for a drug delivery platform to highly vascularized tumors.

In vitro cell assays are not suitable to predict and compare therapeutic effects of drug-loaded nanovesicles which rely on the enhanced permeation and retention effect[13]. We have incubated RMS Rh4-FR4 wt and Rh4-FR4ko cells with increasing concentrations of targeted liposomes and L-mCh but were not able to see significant differences in cytotoxic effects between the liposomes and the cell lines (data not shown). These results were obtained, even after the liposomes were incubated for 1 h or 2 h on the attached cells and subsequently washed off to prevent the unspecific uptake of liposomes within the three days of cultivation, or drug release. Unspecific binding of the liposomes to cell culture plates could be an explanation for this. Therefore, the therapeutic potential of FGFR4-targeted drug delivery to RMS needs to be further studied in vivo.

We were able to verify the selective cell-mediated cytotoxicity of nanobody-based FGFR4-CAR T cells towards Rh4-FR4 wt. Although we saw some differences in killing efficiencies between three CD8+ T cells donors A, B and C, all FGFR4-CAR Ts showed the same specific trend. Real-time cell analysis represents an elegant tool to monitor the cytotoxic potential of CAR Ts and revealed no or reduced effects of FGFR4-CAR T cells on Rh4-FR4ko, comparable to that of CD19-CAR T cells. We believe that the immune-based treatment of RMS with FGFR4-CAR T cells holds promising potential, since RMS tumors display aberrant high FGFR4 expression compared to healthy tissues[39]. It has been shown that high antigen densities above a certain threshold level are required for effective CAR T cell activation and, allowing a therapeutic window for RMS treatment[46,47].

Since the identification of aberrant FGFR4 expression and signaling in RMS, it has been investigated as a possible therapeutic target. Targeting of the receptor with the small molecule inhibitor PD173074 has been reported to induce tumor regression in ARMS bearing mice, but came along with toxic side effects[48]. Li and colleagues investigated the therapeutic effect of the multi-kinase inhibitor ponatinib[36]. In vitro experiments with ERMS and ARMS showed high sensitivities of the cells to the inhibitor with $IC_{50}$ values in the low nanomolar range. Furthermore, they were able to show that the inhibitor delayed tumor growth only in mice bearing RMS with FGFR4 mutations. In a further study, FGFR4 downstream signaling pathways PI3K-AKT-mTOR and RAS-MEK-ERK were targeted simultaneously in RMS and showed a synergistic effect in vitro and in vivo[49]. Therapies for RMS based on FGFR4 antibodies have been investigated with promising results, either as antibody drug conjugates (ADC)[50-52], or with the antigen binding domain grafted on chimeric antigen receptors (CARs) to generate CAR T cells[53]. With our work we show here a novel promising strategy of FGFR4 targeting based on nanobodies by active drug delivery and T cell recruitment.

In summary, we have selected FGFR4-specific nanobodies with inhibitory effects on receptor signaling. Furthermore, we developed an efficient drug-delivery platform for RMS treatment via targeted liposomal VCR and could show an effective cell-mediated cytotoxicity with FGFR4-CAR T cells in vitro. The tumor targeting approaches need to be tested in an RMS in vivo model, and could be further applied to other FGFR4-expressing tumors.

REFERENCES

1. Skapek, S. X. et al. Rhabdomyosarcoma. *Nat. Rev. Dis. Prim.* 5, 14-16 (2019).
2. Sorensen, P. H. B. et al. PAX3-FKHR and PAX7-FKHR gene fusions are prognostic indicators in alveolar rhabdomyosarcoma: A report from the Children's Oncology Group. *J Clin. Oncol.* 20, 2672-2679 (2002).
3. Shern, J. F. et al. Comprehensive genomic analysis of rhabdomyosarcoma reveals a landscape of alterations affecting a common genetic axis in fusion-positive and fusion-negative tumors. *Cancer Discov.* 4, 216-231 (2014).
4. Van Gaal, J. C. et al. The impact of age on outcome of embryonal and alveolar rhabdomyosarcoma patients. A multicenter study. *Anticancer Res.* 32, 4485-4498 (2012).
5. Sultan, I., Qaddoumi, I., Yaser, S., Rodriguez-Galindo, C. & Ferrari, A. Comparing adult and pediatric rhabdomyosarcoma in the surveillance, epidemiology and end results program, 1973 to 2005: An analysis of 2,600 patients. *J Clin. Oncol.* 27, 3391-3397 (2009).
6. Marics, I., Padilla, F., Guillemot, J., Scaal, M. & Marcelle, C. FGFR4 signaling is a necessary step in limb muscle differentiation. *Development* 129, 4559-4569 (2002).
7. Zhao, P. et al. Fgfr4 Is Required for Effective Muscle Regeneration in Vivo DELINEATION OF A MyoD- Tead2-Fgfr4 TRANSCRIPTIONAL PATHWAY. *J. Biol. Chem.* 281, 429-438 (2006).

8. Hughes, S. E. Differential expression of the fibroblast growth factor receptor (FGFR) multigene family in normal human adult tissues. *J. Histochem. Cytochem.* 45, 1005-1019 (1997).

9. Khan, J. et al. Classification and diagnostic prediction of cancers using gene expression and artificial neural networks. *Nat. Med.* 7, 673-679 (2001).

10. Ferrari, M. Cancer nanotechnology: Opportunities and challenges. *Nat. Rev. Cancer* 5, 161-171 (2005).

11. Kumari, P., Ghosh, B. & Biswas, S. Nanocarriers for cancer-targeted drug delivery. *J. Drug Target.* 24, 179-191 (2016).

12. Li, Z., Tan, S., Li, S., Shen, Q. & Wang, K. Cancer drug delivery in the nano era: An overview and perspectives (Review). *Oncol. Rep.* 38, 611-624 (2017).

13. Matsumura, Y. & Maeda, H. A New Concept for Macromolecular Therapeutics in Cancer Chemotherapy: Mechanism of Tumoritropic Accumulation of Proteins and the Antitumor Agent Smancs. *Cancer Res.* 46, 6387-6392 (1986).

14. Jain, R. K. Transport of Molecules, Particles, and Cells in Solid Tumors. *Annu. Rev. Biomed. Eng.* 1, 241-263 (1999).

15. Torchilin, V. Tumor delivery of macromolecular drugs based on the EPR effect. *Adv. Drug Deliv. Rev.* 63, 131-135 (2011).

16. Bulbake, U., Doppalapudi, S., Kommineni, N. & Khan, W. Liposomal formulations in clinical use: An updated review. *Pharmaceutics* 9, 1-33 (2017).

17. O'Brien, M. E. R. et al. Reduced cardiotoxicity and comparable efficacy in a phase III trial of pegylated liposomal doxorubicin HCl (CAELYX™/Doxil®) versus conventional doxorubicin for first-line treatment of metastatic breast cancer. *Ann. Oncol.* 15, 440-449 (2004).

18. Gill, P. S. et al. Randomized phase III trial of liposomal daunorubicin versus doxorubicin, bleomycin, and vincristine in AIDS-related Kaposi's sarcoma. *J Clin. Oncol.* 14, 2353-2364 (1996).

19. Shah, N. N. et al. Vincristine Sulfate Liposomes Injection (VSLI, Marqibo®): Results From a Phase I Study in Children, Adolescents, and Young Adults With Refractory Solid Tumors or Leukemias. *Pediatr. Blood Cancer* 63, 997-1005 (2016).

20. Kirpotin, D. B. et al. Antibody targeting of long-circulating lipidic nanoparticles does not increase tumor localization but does increase internalization in animal models. *Cancer Res.* 66, 6732-6740 (2006).

21. Hamer-Casterman Atarchouch, T, C. et al. Naturally occurring antibodies devoid of light chains. *Nature* 363, 446-448 (1993).

22. Oliveira, S., Heukers, R., Sornkom, J., Kok, R. J. & Van Bergen En Henegouwen, P. M. P. Targeting tumors with nanobodies for cancer imaging and therapy. *J. Control. Release* 172, 607-617 (2013).

23. Roveri, M. et al. Prolonged circulation and increased tumor accumulation of liposomal vincristine in a mouse model of rhabdomyosarcoma. *Nanomedicine* nnm-2017-0430 (2017). doi:10.2217/nnm-2017-0430

24. Moutel, S. et al. NaLi—H1: A universal synthetic library of humanized nanobodies providing highly functional antibodies and intrabodies. (2016). doi:10.7554/eLife.16228.001

25. June, C. H., O'Connor, R. S., Kawalekar, O. U., Ghassemi, S. & Milone, M. C. CAR T cell immunotherapy for human cancer. *Science* (80-.). 359, 1361-1365 (2018).

26. Kochenderfer, J. N. et al. B-cell depletion and remissions of malignancy along with cytokine-associated toxicity in a clinical trial of anti-CD19 chimeric-antigen-receptor-transduced T cells. *Blood* 119, 2709-2720 (2012).

27. Gill, S., Maus, M. V & Porter, D. L. Chimeric antigen receptor T cell therapy: 25 years in the making. *Blood Rev.* 30, 157-167 (2016).

28. Fry, T. J. et al. CD22-targeted CAR T cells induce remission in B-ALL that is naive or resistant to CD19-targeted. *Nat. Med.* 24, 20-28 (2018).

29. Ali, S. A. et al. T cells expressing an anti-B-cell maturation antigen chimeric antigen receptor cause remissions of multiple myeloma. *Blood* 128, 1688-1700 (2016).

30. Ahmed, N. et al. Human Epidermal Growth Factor Receptor 2 (HER2)—Specific Chimeric Antigen Receptor—Modified T Cells for the Immunotherapy of HER2-Positive Sarcoma. *J. Clin. Oncol.* 33, 1688-1696 (2015).

31. Majzner, R. G. et al. CAR T cells targeting B7-H3, a pan-cancer antigen, demonstrate potent preclinical activity against pediatric solid tumors and brain tumors. *Clin. Cancer Res.* 25, 2560-2574 (2019).

32. Crose, L. E. S. et al. FGFR4 blockade exerts distinct antitumorigenic effects in human embryonal versus alveolar rhabdomyosarcoma. *Clin. Cancer Res.* 18, 3780-3790 (2012).

33. Turner, N. & Grose, R. Fibroblast growth factor signalling: From development to cancer. *Nat. Rev. Cancer* 10, 116-129 (2010).

34. Sapra, P. & Allen, T. M. Internalizing antibodies are necessary for improved therapeutic efficacy of antibody-targeted liposomal drugs. *Cancer Res.* 62, 7190-7194 (2002).

35. Ying, Z. et al. A safe and potent anti-CD19 CAR T cell therapy. *Nat. Med.* 25, 947-953 (2019).

36. Li, S. Q. et al. Targeting Wild-Type and Mutationally Activated FGFR4 in Rhabdomyosarcoma with the Inhibitor Ponatinib (AP24534). *PLoS One* 8, (2013).

37. Cao, L. et al. Genome-Wide Identification of PAX3-FKHR Binding Sites in Rhabdomyosarcoma Reveals Candidate Target Genes Important for Development and Cancer. *Cancer Res.* 70, 6497-6509 (2010).

38. Sun, X. et al. Rhabdomyosarcoma: Advances in Molecular and Cellular Biology. *J. Chem. Inf. Model.* 2015, 179-200 (2015).

39. Taylor J, A, C. & Al, T. P. C. J. S. Y. et. Identification of FGFR4-activating mutations in human rhabdomyosarcomas that promote metastasis in xenotransplanted models. *J. Clin. Invest.* 119, 3395-3407 (2009).

40. Seki, M. et al. Integrated genetic and epigenetic analysis defines novel molecular subgroups in rhabdomyosarcoma. *Nat. Commun.* 6, (2015).

41. Sawey, E. T. et al. Identification of a Therapeutic Strategy Targeting Amplified FGF19 in Liver Cancer by Oncogenomic Screening. *Cancer Cell* 19, 347-358 (2011).

42. French, D. M. et al. Targeting FGFR4 inhibits hepatocellular carcinoma in preclinical mouse models. *PLoS One* 7, 1-12 (2012).

43. Gao, L. et al. FGF19 amplification reveals an oncogenic dependency upon autocrine FGF19/FGFR4 signaling in head and neck squamous cell carcinoma. *Oncogene* 38, 2394-2404 (2019).

44. Helsten, T., Schwaederle, M. & Kurzrock, R. Fibroblast growth factor receptor signaling in hereditary and neoplastic disease: biologic and clinical implications. *Cancer Metastsis Rev.* 34, 479-496 (2015).

45. Oliveira, S. et al. Downregulation of EGFR by a novel multivalent nanobody-liposome platform. *J. Control. Release* 145, 165-175 (2010).
46. Walker, A. J. et al. Tumor Antigen and Receptor Densities Regulate Efficacy of a Chimeric Antigen Receptor Targeting Anaplastic Lymphoma Kinase. *Mol. Ther.* 25, 2189-2201 (2017).
47. Caruso, H. et al. Tuning Sensitivity of CAR to EGFR Density Limits Recognition of Normal Tissue While Maintaining Potent Antitumor Activity. *Cancer Res.* 75, 3505-3518 (2015).
48. Hinson, a R. et al. Human rhabdomyosarcoma cell lines for rhabdomyosarcoma research: utility and pitfalls. *Front Oncol* 3, 183 (2013).
49. Renshaw, J. et al. Dual blockade of the PI3K/AKT/mTOR (AZD8055) and RAS/MEK/ERK (AZD6244) pathways synergistically inhibits rhabdomyosarcoma cell growth in vitro and in vivo. *Clin. Cancer Res.* 19, 5940-5951 (2013).
50. Baskar, S. et al. FGFR4 as a potential therapeutic target for monoclonal antibody based intervention in rhabdomyosarcoma. [abstract]. In: Proceedings of the 106th Annual Meeting of the American Association for Cancer Research; 2015 Apr. 18-22; Philadelphia, PA. Philadelphia. *Cancer Res.* 75, Abstract nr 2488 (2015).
51. Baskar, S. Targeting FGFR4 with monoclonal antibodies as therapeutic agents for the treatment of rhabdomyosarcoma. [abstract]. In: Proceedings of the 107th Annual Meeting of the American Association for Cancer Research; 2016 Apr. 16-20; New Orleans, LA. Phila. *Cancer Res.* 76, Abstract nr 4996 (2016).
52. Meyer, M. J. et al. In vitro and in vivo activity of a highly potent and novel FGFR2/FGFR4 dual targeting antibody-drug conjugate. [abstract]. In: Proceedings of the 106th Annual Meeting of the American Association for Cancer Research; 2015 Apr. 18-22; Philadelphia, PA. Phila. *Cancer Res.* 75, Abstract nr 1680 (2015).
53. Shivaprasad, N. et al. 649. Developing FGFR4 Chimeric Antigen Receptor CAR T Cell Therapy Against Rhabdomyosarcoma. *Mol. Ther.* 24, S257-S258 (2016).
54. Geertsma, E. R. & Dutzler, R. A versatile and efficient high-throughput cloning tool for structural biology. *Biochemistry* 50, 3272-3278 (2011).
55. Gentili, M. et al. Transmission of innate immune signaling by packaging of cGAMP in viral particles. *Science* (80-.). 349, 1232-1236 (2015).
56. Nizak, C., Moutel, S., Goud, B. & Perez, F. Selection and application of recombinant antibodies as sensors of Rab protein conformation. *Methods Enzymol.* 403, 135-153 (2005).

```
Sequence listing:

SEQ ID NO: 1    A8 CDR1           RTYSRDT

SEQ ID NO: 2    A8 CDR2           SRHSHTT

SEQ ID NO: 3    A8 CDR3           EWDVFDMHYALPPMW

SEQ ID NO: 4    B1 CDR1           YTSRSSA

SEQ ID NO: 5    B1 CDR2           DLTGYPY

SEQ ID NO: 6    B1 CDR3           AYQDDKWTYGSQHGK

SEQ ID NO: 7    B5 CDR1           RTWLTT

SEQ ID NO: 8    B5 CDR2           SFSSKQG

SEQ ID NO: 9    B5 CDR3           YASYPRHQGNGRWKDFVE

SEQ ID NO: 10   F8 CDR1           TGYALDD

SEQ ID NO: 11   F8 CDR2           DDESMAD

SEQ ID NO: 12   F8CDR3            SYKEYKYQSGHHYFA

SEQ ID NO: 13   NaLi FRW1         EVQLQASGGGFVQPGGSLRLSCAASG

SEQ ID NO: 14   NaLi FRW2         MGWFRQAPGKEREFVSAIS

SEQ ID NO: 15   NaLi FRW3         YYADSVKGRFTISRDNSKNTVYLQMNSLRAEDTATYYCA

SEQ ID NO: 16   NaLi FRW4         YWGQGTQVTVSS

SEQ ID NO: 17   Gimli FRW1        EVQLVESGGGLVQPGGSLRLSCAASG

SEQ ID NO: 18   Gimli FRW2        MGWVRQAPGKGLEWVSAIS

SEQ ID NO: 19   Gimli FRW3        YYADSVKGRFTISRDNSKNTVYLQMNSLRAEDTAVYYCA

SEQ ID NO: 20   Gimli FRW4        YRGQGTLVTVSS

SEQ ID NO: 21   A8 CDR1           CGTACATACAGTCGTGATACA
                (nucleic acid)

SEQ ID NO: 22   A8 CDR2           AGTCGTCATTCGCATACAACA
                (nucleic acid)
```

-continued

| Sequence listing: |

```
SEQ ID NO: 23   A8 CDR3        GAGTGGGACGTTTTTGACATGCACTATGCACTGCCTCCT
                (nucleic acid) ATGTGG SEQ ID NO: 24   B1 CDR1        TATACAAGTCGTTCGTCCGCA
                (nucleic acid)

SEQ ID NO: 25   B1 CDR2        GACCTGACAGGGTATCCTTAC
                (nucleic acid)

SEQ ID NO: 26   B1 CDR3        GCATATCAGGACGACAAGTGGACATATGGTTCGCAGCA
                (nucleic acid) CGGTAAG SEQ ID NO: 27   B5 CDR1        CGTACTTCATGGCTGACTACA
                (nucleic acid)

SEQ ID NO: 28   B5 CDR2        AGTTTTTCGAGTAAGCAGGGT
                (nucleic acid)

SEQ ID NO: 29   B5 CDR3        TATGCATCGTATCCTCGTCACCAGGGTAACGGTCGTTGG
                (nucleic acid) AAGGACTTTGTTGAG SEQ ID NO: 30   F8 CDR1        ACAGGATATGCCCTCGATGAT
                (nucleic acid)

SEQ ID NO: 31   F8 CDR2        GATGATGAGAGTATGGCTGAT
                (nucleic acid)

SEQ ID NO: 32   F8 CDR3        TCCTATAAGGAGTACAAGTATCAGAGCGGACACCACTA
                (nucleic acid) TTTCGCT SEQ ID NO: 33   NaLi FRW1      GAAGTGCAGCTGCAGGCTTCCGGGGGAGGATTTGTGCA
                (nucleic acid) GCCGGGGGGGTCATTGCGACTGAGCTGCGCCGCATCCG
                               GG SEQ ID NO: 34   NaLi FRW2      ATGGGCTGGTTTCGTCAGGCCCCTGGCAAGGAGAGAGA
                (nucleic acid) GTTCGTTTCCGCCATCTCg SEQ ID NO: 35   NaLi FRW3      TAcTACGCTGACAGCGTAAAGGGAAGATTTACAATTAGC
                (nucleic acid) CGGGATAACTCCAAAAACACGGTCTATCTCCAGATGAA
                               CAGCCTCAGGGCCGAGGACACAGCTACGTATTACTGTG
                               Ca SEQ ID NO: 36   NaLi FRW4      TATTGGGGACAGGGGACGCAGGTAACTGTGAGTAGC
                (nucleic acid)

SEQ ID NO: 37   Gimli FRW1     gaagtgcagctggtggagtccggggggaggactggtgcagccggggggggtcattgcgact
                (nucleic acid) gagctgcgccgcatccggg SEQ ID NO: 38   Gimli FRW2     atgggctgggttcgtcaggcccctggcaaggggctggagtgggtttccgccatctcc
                (nucleic acid)

SEQ ID NO: 39   Gimli FRW3     tattacgctgacagcgtaaagggaagatttacaattagccgggataactccaaaaacacggt
                (nucleic acid) ctatctccagatgaacagcctcagggccgaggacactgcagtgtattactgtgca SEQ ID NO: 40   Gimli FRW4     tatcgtggacaggggacgctggtaactgtgagtagc
                (nucleic acid)

SEQ ID NO: 41   A8 sdAb (full  EVQLQASGGGFVQPGGSLRLSCAASGRTYSRDTMGWFRQ
                aa seq)        APGKEREFVSAISSRHSHTTYYADSVKGRFTISRDNSKNTV
                               YLQMNSLRAEDTATYYCAEWDVFDMHYALPPMWYWGQ
                               GTQVTVSS SEQ ID NO: 42   B1 sdAb (full  EVQLQASGGGFVQPGGSLRLSCAASGYTSRSSAMGWFRQ
                aa seq)        APGKEREFVSAISDLTGYPYYYADSVKGRFTISRDNSKNTV
                               YLQMNSLRAEDTATYYCAAYQDDKWTYGSQHGKYWGQ
                               GTQVTVSS SEQ ID NO: 43   B5 sdAb (full  EVQLQASGGGFVQPGGSLRLSCAASGRTSWLTTMGWFRQ
                aa seq)        APGKEREFVSAISSFSSKQGYYADSVKGRFTISRDNSKNTV
                               YLQMNSLRAEDTATYYCAYASYPRHQGNGRWKDFVEYW
                               GQGTQVTVSS SEQ ID NO: 44   F8 sdAb (full  EVQLVESGGGLVQPGGSLRLSCAASGTGYALDDMGWVR
                aa seq)        QAPGKGLEWVSAISDDESMADYYADSVKGRFTISRDNSK
                               NTVYLQMNSLRAEDTAVYYCASYKEYKYQSGHHYFAYR
                               GQGTLVTVSS
```

-continued

---

Sequence listing:

---

| SEQ ID NO: 45 | FGFR4 (human aa seq) | MRLLLALLGVLLSVPGPPVLSLEASEEVELEPCLAP SLEQQEQELTVALGQPVRLCCGRAERGGHWYKEGSRLAP AGRVRGWRGRLEIASFLPEDAGRYLCLARGSMIVLQNLTL ITGDSLTSSNDDEDPKSHRDPSNRHSYPQQAPYWTHPQRM EKKLHAVPAGNTVKFRCPAAGNPTPTIRWLKDGQAFHGE NRIGGIRLRHQHWSLVMESVVPSDRGTYTCLVENAVGSIR YNYLLDVLERSPHRPILQAGLPANTTAVVGSDVELLCKVY SDAQPHIQWLKHIVINGSSFGADGFPYVQVLKTADINSSEV EVLYLRNVSAEDAGEYTCLAGNSIGLSYQSAWLTVLPEED PTWTAAAPEARYTDIILYASGSLALAVLLLLAGLYRGQAL HGRHPRPPATVQKLSRFPLARQFSLESGSSGKSSSSLVRGV RLSSSGPALLAGLVSLDLPLDPLWEFPRDRLVLGKPLGEGC FGQVVRAEAFGMDPARPDQASTVAVKMLKDNASDKDLA DLVSEMEVMKLIGRHKNIINLLGVCTQEGPLYVIVECAAK GNLREFLRARRPPGPDLSPDGPRSSEGPLSFPVLVSCAYQV ARGMQYLESRKCIHRDLAARNVLVTEDNVMKIADFGLAR GVHHIDYYKKTSNGRLPVKWMAPEALFDRVYTHQSDVW SFGILLWEIFTLGGSPYPGIPVEELFSLLREGHRMDRPPHCP PELYGLMRECWHAAPSQRPTFKQLVEALDKVLLAVSEEY LDLRLTFGPYSPSGGDASSTCSSSDSVFSHDPLPLGSSSFPF GSGVQT |

---

The invention claimed is:

1. A humanized anti-FGFR4 synthetic single domain antibody (anti-FGFR4 sdAb), wherein said humanized anti-FGFR4 sdAb has the following formula FRW1-CDR1-FRW2-CDR2-FRW3-CDR3-FRW4, and wherein the CDRs are selected from the group consisting of:

a CDR1 of SEQ ID NO:1; a CDR2 of SEQ ID NO:2 and a CDR3 of SEQ ID NO:3, a CDR1 of SEQ ID NO:4; a CDR2 of SEQ ID NO:5 and a CDR3 of SEQ ID NO:6, a CDR1 of SEQ ID NO:7; a CDR2 of SEQ ID NO:8 and a CDR3 of SEQ ID NO:9, and a CDR1 of SEQ ID NO:10; a CDR2 of SEQ ID NO:11 and a CDR3 of SEQ ID NO:12.

2. The humanized anti-FGFR4 sdAb according to claim 1, wherein the FRW1, FRW2, FRW3 AND FRW4 consist of:

a FRW1 selected from SEQ ID NO:13 or SEQ ID NO: 17,
a FRW2 selected from SEQ ID NO:14 or SEQ ID NO: 18,
a FRW3 selected from SEQ ID NO:15 or SEQ ID NO: 19,
a FRW4 selected from SEQ ID NO:16 or SEQ ID NO: 20,
or functional variants thereof, wherein the functional variants comprise no more than 0, 1, 2 or 3 conservative amino acid substitutions relative to SEQ ID NOs: 13-20.

3. The humanized anti-FGFR4 sdAb according to claim 2, comprising a sequence selected from the group consisting of: SEQ ID NO:41, SEQ ID NO:42, SEQ ID NO:43, and SEQ ID NO:44.

4. The humanized anti-FGFR4 sdAb according to claim 1, which is linked directly or indirectly, or covalently or non-covalently, to a compound of interest selected from the group consisting of: a nucleic acid, a polypeptide, a virus, a toxin and a chemical entity.

5. The humanized anti-FGFR4 sdAb according to claim 4, wherein the polypeptide or the chemical entity is a diagnostic compound selected from the group consisting of: an enzyme, a fluorophore, a NMR or MRI contrast agent, a radioisotope and a nanoparticle.

6. The humanized anti-FGFR4 sdAb according to claim 4, wherein the nucleic acid, the polypeptide, the virus, the toxin, or the chemical entity is a therapeutic compound selected from the group consisting of: cytotoxic agents, chemotherapeutic agents, radioisotopes, targeted anti-cancer agents, immunotherapeutic agents, and lytic peptides.

7. The humanized anti-FGFR4 sdAb according to claim 1, which is linked directly or indirectly, or covalently or non-covalently, to a drug nanocarrier, optionally wherein the drug nanocarrier comprises an organic nanocarrier.

8. The humanized anti-FGFR4 sdAb according to claim 7, wherein the organic nanocarrier is selected from the group consisting of: polymeric nanoparticles, liposomes, micelles and protein-based nanocarriers.

9. The humanized ant-FGFR4 sdAb according to claim 7, wherein the drug nanocarrier includes a therapeutic compound or a diagnostic compound, optionally wherein the therapeutic compound is a cytotoxic compound.

10. The humanized anti-FGFR4 sdAb according to claim 1, which is fused to an immunoglobulin domain, optionally, wherein the immunoglobulin domain is an Fc domain.

11. A multispecific binding compound comprising at least a first synthetic single domain antibody (sdAb) comprising the humanized anti-FGFR4 sdAb as defined in claim 1, and further comprising a second sdAb binding to a second antigen, optionally wherein the first sdAb is located at the N-terminus of the second sdAb or wherein the first sdAb is located at the C-terminus of the second sdAb.

12. A chimeric antigen receptor (CAR) comprising (a) an antigen binding domain comprising at least a first sdAb comprising the humanized anti-FGFR4 sdAb as defined in claim 1, and optionally a second sdAb binding to a second antigen; (b) a transmembrane domain; and (c) an intracellular domain.

13. The CAR according to claim 12, wherein the transmembrane domain is selected from the group consisting of the transmembrane domains of CD3zeta, CD28, CD8 alpha, DAP10, and DAP12.

14. The CAR according to claim 12, wherein the intracellular domain is selected from the group consisting of the intracellular domains of CD28, OX40, CD3zeta, 4-1BB, DAP10 and/or DAP1 intracellular domains, optionally wherein the intracellular domain comprises the CD3zeta and 4-1BB intracellular domains.

15. The CAR according to claim 12, comprising a CD8 alpha transmembrane domain and CD3zeta and 4-1BB intracellular domains.

16. The CAR according to claim 12, which further comprises a spacer and/or a hinge domain located between the C-terminus of the antigen binding domain and the N-terminus of the transmembrane domain, optionally wherein the hinge is the hinge of CD8 alpha.

17. The CAR according to claim 12, which further comprises a signal peptide located at the N-terminus of the CAR.

18. An isolated nucleic acid encoding the humanized anti-FGFR4 sdAb according to claim 1 or encoding the CAR according to claim 12.

19. The isolated nucleic acid according to claim 18, wherein the isolated nucleic acid encoding the humanized anti-FGFR4 sdAb or encoding the CAR is linked to a heterologous regulatory control sequence.

20. A vector comprising the isolated nucleic acid of claim 18.

21. A host cell comprising the isolated nucleic acid according to claim 18.

22. An isolated cell or population of cells expressing the humanized anti-FGFR4 sdAb according to claim 1, or the CAR according to claim 12.

23. The isolated cell or population of cells according to claim 22, wherein said isolated cell or population of cells is or are an allogenic or autologous cell or cells selected from the group consisting of macrophages, NK cells, CD4+/CD8+ T cells, TILs/tumor derived CD8+ T cells, central memory CD8+ T cells, Treg cells, MAIT cells, and Yδ T cells.

24. An in vitro or ex vivo method for diagnosing or monitoring an FGFR4 mediated cancer in a subject comprising the steps of:

a) contacting in vitro a sample from said subject with a diagnostic agent comprising the humanized anti-FGFR4 sdAb according to claim 5, and b) determining the expression of FGFR4 in said sample.

* * * * *